United States Patent
Guan et al.

(10) Patent No.: US 11,097,012 B2
(45) Date of Patent: *Aug. 24, 2021

(54) BIODEGRADABLE VECTORS FOR EFFICIENT RNA DELIVERY

(71) Applicant: The Regents of the University of California, Oakland, CA (US)

(72) Inventors: Zhibin Guan, Irvine, CA (US); Nathan Oldenhuis, Somerville, MA (US)

(73) Assignee: The Regents of the University of California, Oakland, CA (US)

( * ) Notice: Subject to any disclaimer, the term of this patent is extended or adjusted under 35 U.S.C. 154(b) by 259 days.

This patent is subject to a terminal disclaimer.

(21) Appl. No.: 16/084,220

(22) PCT Filed: Mar. 10, 2017

(86) PCT No.: PCT/US2017/021978
§ 371 (c)(1),
(2) Date: Sep. 11, 2018

(87) PCT Pub. No.: WO2017/160662
PCT Pub. Date: Sep. 21, 2017

(65) Prior Publication Data
US 2019/0070304 A1   Mar. 7, 2019

Related U.S. Application Data

(60) Provisional application No. 62/307,480, filed on Mar. 12, 2016.

(51) Int. Cl.
*A61K 47/64* (2017.01)
*C08G 75/14* (2006.01)
*C12N 15/11* (2006.01)
*C12N 15/87* (2006.01)

(52) U.S. Cl.
CPC .......... *A61K 47/6455* (2017.08); *C08G 75/14* (2013.01); *C12N 15/111* (2013.01); *C12N 15/87* (2013.01); *C12N 2310/14* (2013.01); *C12N 2310/20* (2017.05); *C12N 2320/32* (2013.01)

(58) Field of Classification Search
CPC ..... A61K 47/6455; C08G 75/14; C12N 15/87
See application file for complete search history.

(56) References Cited

U.S. PATENT DOCUMENTS

| | | | |
|---|---|---|---|
| 9,745,421 B2 * | 8/2017 | Guan | C12N 15/111 |
| 2007/0129305 A1 | 6/2007 | Divita et al. | |
| 2009/0105115 A1 | 4/2009 | Reineke | |
| 2012/0183578 A1 | 7/2012 | Sinko et al. | |
| 2013/0302257 A1 | 11/2013 | Minko et al. | |
| 2014/0242123 A1 | 8/2014 | Guan et al. | |
| 2014/0288150 A1 | 9/2014 | Guan et al. | |
| 2014/0288190 A1 | 9/2014 | Ashley et al. | |
| 2015/0297742 A1 | 10/2015 | Strieker et al. | |
| 2016/0030590 A1 | 2/2016 | Guan et al. | |
| 2016/0340661 A1 * | 11/2016 | Cong | A61P 27/02 |
| 2017/0173128 A1 * | 6/2017 | Hoge | A61K 39/39 |
| 2018/0072849 A1 | 3/2018 | Guan et al. | |

FOREIGN PATENT DOCUMENTS

| | | |
|---|---|---|
| WO | 2006/060182 | 6/2006 |
| WO | 2007014363 A2 | 2/2007 |
| WO | 2007015168 A2 | 2/2007 |

OTHER PUBLICATIONS

Lee et al., "Hydrogels for tissue engineering." J. Chem ReV 101:1869-1879 (2001).
Lee et al., "Three-dimensional micropatterning of bioactive hydrogels via two-photon laser scanning photolithography for guided 3D cell migration." Biomaterials 29:2962-2968 (2008).
Lee et al., "Growth factor delivery-based tissue engineering: general approaches and a review of recent developments." J R Soc Interface 8:153e70 (2011).
Liao et al., "De novo design of saccharide-peptide hydrogels as synthetic scaffolds for tailored cell responses." J Am Chem Soc 131:17638e46 (2009).
Liao et al., "Maintaining functional islets through encapsulation in an injectable saccharide-peptide hydrogel." Biomaterials 34(16):3984-91 (Mar. 7, 2013).
Liao et al., "The effect of cell-matrix interaction on encapsulated human islets. presented at the Congress of the International Pancreas and Islet Transplantation," (Jun. 2013).
Liao et al., "The Effect of Cell-Matrix Interaction on Encapsulated Human Islets," Transplantation 96(65):S97 (Sep. 27, 2013).
Lieb, Jannette. Non-final Office Action for U.S. Appl. No. 14/814,475 (dated Jul. 22, 2016).
Lieb, Jannette. Final Office Action for U.S. Appl. No. 14/814,475 (dated Apr. 11, 2017).
Lieb, Jannette. Advisory Action for U.S. Appl. No. 14/814,475 (dated Jul. 12, 2017).
Lieb, Jannette. Notice of Allowance for U.S. Appl. No. 14/814,475 (dated Sep. 19, 2017).
Lin et al., "PEG Hydrogels for the Controlled Release of Biomolecules in Regenerative Medicine." Pharmacol. Res. 26:631-643 (2009).
Lin et al., "Glucagon-like peptide-1 functionalized PEG hydrogels promote survival and function of encapsulated pancreatic beta-cells." Biomacromolecules 10:2460e7 (2009).
Liu et al., "Interfacial Assembly of a Series of Cinnamoyl-Containing Bolaamphiphiles: Spacer-Controlled Packing, Photochemistry, and Odd-Even Effect", Langmuir 28:3474-3482 (2012).
Liu et al., "SiRNA Delivery Systems Based on Neutral Cross-Linked Dendrimers," Bioconjug Chem 23:174-183 (Jan. 2012).
Liu et al., "Efficient Delivery of Sticky siRNA and Potent Gene Silencing in aProstate Cancer Model Using a Generation 5 Triethanolamine-Core PAMAM Dendrimer," Mol Pharmaceutics 9:470-481 (Mar. 2012).

(Continued)

*Primary Examiner* — Richard A Schnizer
(74) *Attorney, Agent, or Firm* — Gavrilovich, Dodd & Lindsey LLP

(57) ABSTRACT

The disclosure provides for vectors, and methods of using the vectors to efficiently deliver mRNA and/or ssRNA into cells.

18 Claims, 30 Drawing Sheets

(56) References Cited

OTHER PUBLICATIONS

Love et al., "Lipid-like materials for low-dose, in vivo gene silencing", PNAS 107(5):1864-1869 (2010).
Lu et al., "Making Insoluble Polymer Networks Malleable via Olefin Metathesis." J. Am. Chem. Soc. 134:8424-8427 (2012).
Lu et al., "Olefin Metathesis for Effective Polymer Healing via Dynamic Exchange of Strong Carbon-Carbon Double Bonds." J. Am. Chem. Soc. 134:14226-14231 (2012).
Lutolf et al., "Synthesis and physicochemical characterization of end-linked poly(ethylene glycol)-co-peptide hydrogels formed by Michael-type addition." Biomacromolecules 4:713-722 (2003).
Malone et al., "Cationic liposome-mediated RNA transfection", PNAS 86:6077-6081 (1989).
Martens et al., Tailoring the degradation of hydrogels formed from multivinyl poly(ethylene glycol) and poly(vinyl alcohol) macromers for cartilage tissue engineering. Biomacromolecules 4:283-292 (2003).
Martin et al., Human embryonic stem cells express an immunogenic nonhuman sialic acid. Nat Med 11:228e32 (2005).
McCall et al., Update on islet transplantation. Cold Spring Harb Perspect Med 2:a007823 (2012).
Merkel et al., "Molecular modeling and in vivo imaging can identify successful flexible triazine dendrimer-based siRNA delivery systems," J Control Release 153(1):23-33 (2011).
Metters et al., Network formation and degradation behavior of hydrogels formed by Michael-type addition reactions Biomacromolecules 6:290-301 (2005).
Metzke et al. A novel carbohydrate-derived side-chain polyether with excellent protein resistance. J. Am. Chem. Soc. 125:7760-7761 (2003).
Metzke et al., Structure-property studies on carbohydrate-derived polymers for use as protein-resistant biomaterials. Biomacromolecules 9:208-215 (2008).
Mitragotri et al., "Overcoming the challenges in administering biopharmaceuticals:formulation and delivery strategies", Nat. Rev. Drug Discovery 13:655-672 (2014).
Moassesfar et al., "Slide on Transplantation Medical Cost, Islets vs. Pancreas," presented before the International Pancreas & Islet Transplant Association (IPITA) Congress on Sep. 25, 2013.
Montarnal et al., "Silica-like Malleable Materials from Permanent Organic Networks." Science 334(6058):965-968 (2011).
Negishi et al., "Luminescence technology in preservation and transplantation for rat islet." Islets 2011;3:111e7 (2011).
Nguyen et al., "Polymeric Materials for Gene Delivery and DNA Vaccination," Adv Mater 21:847-867 (2009).
Nguyen et al., "Nucleic acid delivery: the missing pieces of the puzzle?," Acc Chem Res 45:1153-1162 (Jul. 2012).
Nicolay et al., "Responsive Gels Based on a Dynamic Covalent Trithiocarbonate Cross-Linker." Macromolecules 43:4355-4361 (2010).
Nie et al., "Production of heparin-containing hydrogels for modulating cell responses." Acta Biomater. 5:865-875 (2009).
Nikolova et al., "The vascular basement membrane: a niche for insulin gene expression and beta cell proliferation." Dev Cell 10:397e405 (2006).
Nishimura et al., "Silyl Ether as a Robust and Thermally Stable Dynamic Covalent Motif for Malleable Polymer Design." J. Am. Chem. Soc. 139:14881-14884 (2017).
Nuttelman et al., "Macromolecular monomers for the synthesis of hydrogel niches and their application in cell encapsulation and tissue engineering." Prog. Polym. Sci. 33: 167-179 (2008).
Obdia et al., "Reprocessing and Recycling of Highly Cross-Linked Ion-Conducting Networks through Transalkylation Exchanges of C—N Bonds." J. Am. Chem. Soc. 137:6078-6083 (2015).
Oldenhuis et al., "Biodegradable Dendronized Polymers for Efficient mRNA Delivery". Chemistry Select 1:4413-4417 (2016) (Sep. 16, 2016).
Omori et al., "Microassay for glucose-induced preproinsulin mRNA expression to assess islet functional potency for islet transplantation." Transplantation 89:146e54 (2010).
Osthoff et al., "Chemical Stress-Relaxation of Polydimethylsiloxane Elastomers." J. Am. Chem. Soc. 76(18):4659-4663 (1954).
Pasini et al., "Efficient Biocatalytic Cleavage and Recovery of Organic Substrates Supported on Soluble Polymers." Adv. Synth. Catal. 349:971-978 (2007).
Paszek et al., "Tensional homeostasis and the malignant phenotype." Cancer Cell 8:241-254 (2005).
Pavan et al., "Computational Insights into the Interactions between DNA and siRNA with "Rigid" and "Flexible" Triazine Dendrimers," Biomacromolecules 11: 721-730 (2010).
Pavan et al., "Dendrimers and dendrons for siRNA binding: computational insights," J Drug Deliv Sci Tec 22:83-89 (2012).
Pei et al., "Regional Shape Control of Strategically Assembled Multishape Memory Vitrimers." Adv. Mater. 28:156-160 (2016).
Pei et al., "Mouldable liquid-crystalline elastomer actuators with exchangeable covalent bonds." Nature Materials (13):36-41 (2014).
Peppas et al., Hydrogels in biology and medicine: from molecular principles to bionanotechnology AdV. Mater. 18:1345-1360 (2006).
Wang et al. Substrate flexibility regulates growth and apoptosis of normal but not transformed cells. Am. J. Physiol. Cell Physiol. 279:C1345-1350 (2000).
Weber et al., Cell-matrix interactions improve Beta-cell survival and insulin secretion in three-dimensional culture. Tissue Eng Part A 14:1959e68 (2008).
Weber et al., "Hydrogel encapsulation environments functionalized with extracellular matrix interactions increase islet insulin secretion." Matrix Biol 27(8):667-673 (2008).
Whitehead et al., "Knocking down barriers:advances in siRNA delivery", Nature Reviews 8:129-138 (2009).
Williams et al., "The Temperature Dependence of Relaxation Mechanisms in Amorphous Polymers and Other Glass-forming Liquids." J. Am. Chem. Soc. 77(14):3701-3707 (1955).
Won et al., "Oligopeptide complex for targeted non-viral gene delivery to adipocytes", Nature Materials 13:1157-1164 (Oct. 5, 2014).
Wong et al., "Co-Injection of a Targeted, Reversibly Masked Endosomolytic Polymer Dramatically Improves the Efficacy of Cholesterol-Conjugated Small Interfering RNAs In Vivo", Nucleic Acid Therapeutics 22(6):380-390 (2012).
Wu et al., "Polycationic dendrimers interact with RNA molecules: polyaminedendrimers inhibit the catalytic activity of Candida ribozymes." ChemComm 3:313-315 (2005).
Wu et al., "Dendrimers as Carriers for siRNA Delivery and Gene Silencing: A Review", The Scientific World Journal (2013).
Yamaguchi et al., "Growth Factor Mediated Assembly of Cell Receptor-Responsive Hydrogels." J. Am. Chem. Soc. 129:3040-3041 (2007).
Yang et al., "Carbon nanotube-vitrimer composite for facile and efficient photo-welding of epoxy." Chem. Scie 5:3486-3492 (2014).
Yu et al., "An Amphiphilic Dendrimer for Effective Delivery of Small Interfering RNA and Gene Silencing In Vitro and In Vivo", Angewandte Chemie 51:8478-8484 (2012).
Yu et al., "Reprocessing and Recycling of Thermosetting Polymers based on Bond Exchange Reactions." RSC Adv. 4:10108-10117 (2014).
Zeng et al. "Multifunctional Dendronized Peptide Polymer Platform for Safe and Effective siRNA Delivery", JACS 135:4962-4965 (Mar. 15, 2013).
Zhang et al., "Effect of Sterics and Degree of Cross-Linking on the Mechanical Properties of Dynamic Poly(alkylurea-urethane) Networks". Macromolecules 50:5051-5060 (2017).
Zheng et al., "A Surprise from 1954: Siloxane Equilibration Is a Simple, Robust, and Obvious Polymer Self-Healing Mechanism". J. Am Chem. Soc. 134:2024-2027 (2012).
Avci-Adali et al., "Optimized conditions for successful transfection of human endothelial cells with in vitro synthesized and modified mRNA for induction of protein expression," Journal of Biological Engineering 8(8)1-11 (2014).
Cheng et al., "Multifunctional triblock copolymers for intracellular messenger RNA delivery," Biomaterials 33(28):6868-6876 (2012).
Crowley et al., "Efficient Expression of Stabilized mRNAPEG-Peptide Polyplexes in Liver," Gene Ther. 22(12): 993-999 (Dec. 2015).

(56) References Cited

OTHER PUBLICATIONS

Eldredge et al., "Focused Library Approach to Discover Discrete Dipeptide Bolaamphiphiles for siRNA Delivery," Biomacromolecules. 17(10): 3138-3144 (Oct. 10, 2016).
Faneca et al., "Association of albumin or protamine to lipoplexes: enhancement of transfection and resistance to serum," J Gene Med 6: 681-692 (2004).
Heil et al., "Species-Specific Recognition of Single-Stranded RNA via Toll-like Receptor 7 and 8," Science 303:1526-1529 (Mar. 5, 2004).
Kariko et al., "Incorporation of Pseudouridine Into mRNA Yields Superior Nonimmunogenic Vector With Increased Translational Capacity and Biological Stability," Mol Ther. 16(11): 1833-1840 (Nov. 2008).
Kariko et al., "Increased Erythropoiesis in Mice Injected With Submicrogram Quantities of Pseudouridine-containing mRNA Encoding Erythropoietin," Molecular Therapy 20(5):948-953 (May 2012).
Kauffman et al., "Optimization of Lipid Nanoparticle Formulations for mRNA Delivery in Vivo with Fractional Factorial and Definitive Screening Designs," Nano Lett. 15:7300-7306 (2015).
Kormann et al., "Expression of therapeutic proteins after delivery of chemically modified mRNA in mice," Nature Biotechnology 29:154-157 (2011).
Mager et al., "Assessing the uptake kinetics and internalization mechanisms of cell-penetrating peptides using a quenched fluorescence assay," Biochimica et Biophysica Acta 1798:338-343 (2010).
Malone et al., "Cationic liposome-mediated RNA transfection," Proc. Natl. Acad. Sci. USA 86:6077-6081 (Aug. 1989).
Mezo et al., "Synthesis and Structural Characterization of Bioactive Peptide Conjugates using Thioether Linkage Approaches," J. Peptide Sci. 10:701-713 (2004).
Midoux et al., "Lipid-based mRNA vaccine delivery systems," Expert Rev. Vaccines 1-14 (2014).
Oh et al., "Endocytosis and exocytosis of nanoparticles in mammalian cells," International Journal of Nanomedicine 9(Suppl 1):51-63 (2014).
Phua et al., "Transfection Efficiency and Transgene Expression Kinetics of mRNA Delivered in Naked and Nanoparticle Format," J Control Release. 166(3): 227-233 (Mar. 28, 2013).
Phua et al., "Messenger RNA (mRNA) Nanoparticle Tumour Vaccination," Nanoscale. 6(14):7715-29 29 (Jul. 21, 2014).
Piao et al., "Human serum albumin-coated lipid nanoparticles for delivery of siRNA to breast cancer," Nanomedicine. 9(1): 122-129 (Jan. 2013).
Ponsaerts et al., "Cancer immunotherapy using RNA-loaded dendritic cells," Clin Exp Immunol 134:378-384 (2003).
Sahin et al., "mRNA-based therapeutics—developing a new class of drugs," Nature Reviews Drug Discovery 13:759-780 (2014).
Schlake et al., "Developing mRNA-vaccine technologies," RNA Biology 9(11):1319-1330 (Nov. 2012).
Strobel et al., "Human dendritic cells transfected with either RNA or DNA encoding influenza matrix protein M1 differ in their ability to stimulate cytotoxic T lymphocytes," Gene Therapy 7:2028-2035 (2000).
Su et al., "In vitro and in vivo mRNA delivery using lipid-enveloped pH responsive polymer nanoparticles," Mol Pharm. 8(3):774-787 (Jun. 6, 2011).
Tendeloo et al., "Highly efficient gene delivery by mRNA electroporation in human hematopoietic cells: superiority to lipofection and passive pulsing of mRNA and to electroporation of plasmid cDNA for tumor antigen loading of dendritic cells," Blood 98(1):49-56 (Jul., 2001).
Uchida et al., "In Vivo Messenger RNA Introduction into the Central Nervous System Using Polyplex Nanomicelle," PLOS ONE 8(2):e56220 (1-8) (Feb. 2013).
Wang et al., "Systemic Delivery of Modified mRNA Encoding Herpes Simplex Virus 1 Thymidine Kinase for Targeted Cancer Gene Therapy," Molecular %herapy 21(2):358-367 (Feb. 2013).
Yin et al."Non-viral vectors for gene-based therapy," Nature Reviews Genetics (15):541-555 (2014).

Youn et al., "Modified mRNA as an alternative to plasmid DNA (pDNA) for transcript replacement and vaccination therapy," Expert Opin Biol Ther. 15(9):1337-48 (2015).
Zangi et al., "Modified mRNA directs the fate of heart progenitor cells and induces vascular regeneration after myocardial infarction," Nat Biotechnol. 31(10): 898-907 (Oct. 2013).
Zeng et al., "Multifunctional Dendronized Peptide Polymer Platform for Safe and Effective siRNA Delivery," J. Am. Chem. Soc. 135:4962-4965 (2013).
Zeng et al., "Structure-Based Design of Dendritic Peptide Bolaamphiphiles for siRNA Delivery," ACS Cent. Sci. 1:303-312 (2015).
Zhang et al., "Hydroporation as the mechanism of hydrodynamic delivery," Gene Ther. 11(8):675-682 (Apr. 2004).
Di Miceli, Giuseppe, International Search Report and Written Opinion, European Patent Office, PCT/US2017/021978, dated Jun. 2, 2017.
Nickitas-Etienne, Athina, International Preliminary Report on Patentability and Written Opinion, the International Bureau of WIPO, PCT/US2017/021978, dated Sep. 27, 2018.
Perche et al., "Enhancement of dendritic cells transfection in vivo and of vaccination against B16F10 melanoma with mannosylated histidylated lipopolyplexes loaded with tumor antigen messenger RNA". Nanomedicine: Nanotechnology, Biology, and Medicine 7:445-453 (2011).
Pitarresi et al., "Photocrosslinking of dextran and polyaspartamide derivatives: A combination suitable for colon-specific drug delivery." Journal of Controlled Release 119:328-338 (2007).
Ponsaerts et al., "Highly Efficient mRNA-Based Gene Transfer in Feeder-Free Cultured H9 Human Embryonic Stem Cells". Cloning and Stem Cells 6(3):211-216 (2004).
Rackham et al., "Co-transplantation of mesenchymal stem cells maintains islet organisation and morphology in mice" Diabetologia 54:1127-1135 (2011).
Rajeswari et al., "Does Tryptophan Intercalate in DNA? A Comparative Study of Peptide Binding to Alternating and Nonalternating A*T Sequences," Biochemistry 26:6825-6831 (1987).
Reed et al., "In situ mechanical interferometry of matrigel films." Langmuir 25:36-39 (2009).
Rehfeldt et al., "Cell responses to the mechanochemical microenvironment—implications for regenerative medicine and drug delivery." Adv. Drug Delivery Rev. 59:1329-1339 (2007).
Rejman et al., "Size-dependent internalization of particles via the pathways of clathrin and caveolae-mediated endocytosis", Biochem. J. 377:159-169 (2004).
Rettig et al., "Progress Toward In Vivo Use of siRNAs-II," Mol Ther 20:483-512 (Mar. 2012).
Rizzi et al., "Recombinant protein-co-PEG networks as cell-adhesive and proteolytically degradable hydrogel matrixes. Part I: Development and physicochemical characteristics." Biomacromolecules 6:1226-1238 (2005).
Rottger et al., "High-Performance vitrimers from commodity thermoplastics through dioxaborolane metathesis." Science 356:62-65 (2017).
Rozema et al., "Dynamic PolyConjugates for targeted in vivo delivery of siRNA to hepatocytes", PNAS 104(32):12982-12987 (2007).
Sahin et al., "Preparation, characterization and in vivo distribution of terbutaline sulfate loaded albumin microspheres". Journal of Controlled Release 82:345-358 (2002).
Sahin et al., "Combinatorial RNAi for quantitative protein network analysis", PNAS 104(16):6579-6584 (2007).
Salto et al., "Enhanced Hydrophobicity of Fluorinated Lipid Bilayer: A Molecular Dynamics Study", J. Phys. Chem B 112:11305-11309 (2008).
Salvay et al., Extracellular matrix protein-coated scaffolds promote the reversal of diabetes after extrahepatic islet transplantation. Transplantation 85:1456e64 (2008).
Schafer et al., "Redox environment of the cell as viewed through the redox state of the glutathione disulfide/glutathione couple," Free Rad. Biol. Med. 30:1191-1212 (2001).
Schaffer et al., "Molecular Engineering of Viral Gene Delivery Vehicles," Annu Rev Biomed Eng 10:169-194 (2008).

(56) References Cited

OTHER PUBLICATIONS

Schense et al., Cross-linking exogenous bifunctional peptides into fibrin gels with factor XIIIa. Bioconjugate Chem. 10:75-81 (1999).
Schmolke et al., "Dynamically Cross-Linked Polydimethylsiloxane Networks with Ambient-Temperature Self-Healing." Macromolecules 48:8781-8788 (2015).
Schnizer, Richard A. Non-Final Office Action for U.S. Appl. No. 14/221,249 (dated Nov. 25, 2015).
Schnizer, Richard A. Final Office Action for U.S. Appl. No. 14/221,249 (dated May 2, 2016).
Schnizer, Richard A. Advisory Action for U.S. Appl. No. 14/221,249 (dated Jul. 22, 2016).
Schnizer, Richard A. Non-Final Office Action for U.S. Appl. No. 14/221,249 (dated Sep. 20, 2016).
Schnizer, Richard A. Notice of Allowance for U.S. Appl. No. 14/221,249 (dated May 4, 2017).
Schnizer, Richard A. Non-Final Office Action for U.S. Appl. No. 15/688,718 (dated Dec. 26, 2017).
Schnizer, Richard A. Final Office Action for U.S. Appl. No. 15/688,718 (dated Jun. 26, 2018).
Schnizer, Richard A. Notice of Allowance for U.S. Appl. No. 15/688,718 (dated Sep. 5, 2018).
Scott et al., "Photoinduced Plasticity in Cross-Linked Polymers." Science 308:1615-1617 (2005).
Seliktar D. "Designing cell-compatible hydrogels for biomedical applications." Science 336:1124e8 (Jun. 15, 2012).
Sengupta et al., "Alternate glucocorticoid receptor ligand binding structures influence outcomes in an in vivo tissue regeneration model." Comp Biochem Physiol C Toxicol Pharmacol. 156(2):121-129 (2012).
Silva et al., "Selective differentiation of neural progenitor cells by high-epitope density nanofibers." Science 303:1352-1355 (2004).
Smith et al., "Diblock Glycopolymers Promote Colloidal Stability of Polyplexes and Effective pDNA and siRNA Delivery under Physiological Salt and Serum Conditions," Biomacromolecules 12:3015-3022 (2011).
Solari et al., "Marginal mass islet transplantation with autologous mesenchymal stem cells promotes long-term islet allograft survival and sustained normoglycemia." Journal of Autoimmunity 32:116-124 (2009).
Solon et al. Fibroblast adaptation and stiffness matching to soft elastic substrates. Biophys. J. 93:4453-4461 (2007).
Son et al., "Bioreducible Polymers for Gene Silencing and Delivery", Accounts of Chemical Research 45(7):1100-1112 (2012).
Sonawane et al., "Chloride Accumulation and Swelling in Endosomes Enhances DNA Transfer by Polyamine-DNA Polyplexes," J Biol Chem 278:44826-44831 (2003).
Soofi et al., "The elastic modulus of Matrigel as determined by atomic force microscopy." J. Struct. Biol. 167:216-219 (2009).
Stendahl et al., Extracellular matrix in pancreatic islets: relevance to scaffold design and transplantation. Cell Transplant 18:1e12 (2009).
Su et al., Anti-inflammatory peptide-functionalized hydrogels for insulin-secreting cell encapsulation. Biomaterials 31:308e14 (2010).
Tabernero et al., "First-in-Humans Trial of an RNA Interference Therapeutic Targeting VEGF and KSP in Cancer Patients with Liver Involvement," Cancer Discovery 3:406-417 (2013).
Tan et al., Thermosensitive injectable hyaluronic acid hydrogel for adipose tissue engineering. Biomaterials 30(36):6844-6853 (2009).
Tang et al., "In Vitro Gene Delivery by Degraded Polyamidoamine Dendrimers," Bioconjugate Chem 7:703-714 (1996).
Tibbet et al., Hydrogels as Extracellular Matrix Mimics for 3D Cell Culture. Biotechnol Bioeng. 103(4):655-663 (2009).
Toyofuku et al., Natural killer T-cells participate in rejection of islet allografts in the liver of mice. Diabetes 55:34e9 (2006).
Urakami et al., "Living Ring-Opening Polymerization of a Carbohydrate-Derived Lactone for the Synthesis of Protein-Resistant Biomaterials." Biomacromolecules, Jan. 26, 2008, 9, 592-597.
Uzgun et al., "PEGylation Improves Nanoparticle Formation and Transfection Efficiency of Messenger RNA". Pharmaceutical Research 28:2223-2232 (May 19, 2011).

Vercruysse et al. Synthesis and in vitro degradation of new polyvalent hydrazide cross-linked hydrogels of hyaluronic acid. Bioconjugate Chem. 8:686-694 (1997).
Wagner, E., "Polymers for siRNA Delivery: Inspired by Viruses to be Targeted, Dynamic, and Precise," Acc Chem Res 45:1005-1013 (2011).
Wakefield et al., "Membrane Activity and Transfection Ability of Amphipathic Polycations as a Function of Alkyl Group Size," Bioconjug Chem 16:1204-1208 (2005).
Akinc et al., "A combinatorial library of lipid-like materials for delivery of RNAi therapeutics," Nat Biotechnol 26:561-569 (2008).
Amamoto e et al., "Self-Healing of Covalently Cross-Linked Polymers by Reshuffling Thiuram Disulfide Moieties in Air under Visible Light," Adv. Mater. 24:3975-398—(2012).
Amamoto et al., "Repeatable Photoinduced Self-Healing of Covalently Cross-Linked Polymers through Reshuffling of Trithiocarbonate Units," Angew. Chem. Int. Ed. 50:1660-1663 (2011).
Andrianaivo et al., "Hydrodynamics-based transfection of the liver: entrance into hepatocytes of DNA that causes expression takes place very early after injection". The Journal of Gene Medicine 6:877-883 (2004).
Ashcroft et al., "Glucose metabolism in mouse pancreatic islets." Biochem J 118:143e54 (1970).
Banerjee et al. "The influence of hydrogel modulus on the proliferation and differentiation of encapsulated neural stem cells." Biomaterials 30:4695-4699 (2009).
Banwell et al., "Rational design and application of responsive alpha-helical peptide hydrogels." Nat. Mater. 8:596-600 (2009).
Barnard et al., Degradable Self-Assembling Dendrons for Gene Delivery: Experimental and Theoretical Insights Into the Barriers to Cellular Uptake J Am Chem Soc 133:20288-20300 (2011).
Behr, J. P., "Synthetic Gene Transfer Vectors II: Back to the Future," Acc Chem Res 45:980-984 (Feb. 2012).
Bennet et al., "Incompatibility between human blood and isolated islets of Langerhans: a finding with implications for clinical intraportal islet transplantation?," Diabetes 48:1907e14 (1999).
Berkefeld et al., "Silicon a-Effect: A Systematic Experimental and Computational Study of the Hydrolysis of Ca and Cg-Functionalized Alkoxytriorganylsilanes of the Formula Type ROSiMes2(CH2)nX (R=me, ET; n=1, 3; X=Functional group)." Organometallics 33:2721-2737 (2014).
Blomeier et al. Polymer scaffolds as synthetic microenvironments for extrahepatic islet transplantation. Transplantation 82:452e9 (2006).
Borg et al., The use of biomaterials in islet transplantation. Curr Diab Rep 11:434e44 (2011).
Bowman et al., "Covalent Adaptable Networks: Reversible Bond Structures Incorporated in Polymer Networks." Angew. Chem. Int. Ed. 51:4272-4274 (2012).
Brown et al. Importance of hepatic portal circulation for insulin action in streptozotocin-diabetic rats transplanted with fetal pancreases. J Clin Invest 64:1688e94 (1979).
Brunelle et al., "A structureeactivity investigation of hemifluorinated bi-functional bolaamphiphiles designed for gene delivery," C. R. Chimie 12:88-208 (2009).
Brutman et al. "Polylactide Vitrimers." ACS Macro Lett. 3:607-610 (2014)).
Bryant et al., Hydrogel properties influence ECM production by chondrocytes photoencapsulated in poly(ethylene glycol) hydrogels. J. Biomed. Mater. Res. 59:63-72 (2002).
Bryant et al., Incorporation of tissue-specific molecules alters chondrocyte metabolism and gene expression in photocrosslinked hydrogels. Acta Biomater. 1:243-252 (2005).
Burdick et al. Photoencapsulation of osteoblasts in injectable RGD-modified PEG hydrogels for bone tissue engineering Biomaterials 23:4315-4323 (2002).
Burdick et al. Controlled degradation and mechanical behavior of photopolymerized hyaluronic acid networks. Biomacromolecules 6:386-391 (2005).
Burnett et al., "RNA-based Therapeutics—Current Progress and Future Prospects," J. Chem Biol 19:60-71 (Jan. 2012).
Capelot et al., "Catalytic Control of the Vitrimer Glass Transition." ACS Macro Lett. 1:789-792 (2012).

(56) References Cited

OTHER PUBLICATIONS

Carlsson et al., Markedly decreased oxygen tension in transplanted rat pancreatic islets irrespective of the implantation site. Diabetes 50:489e95 (2001).
Castanotto et al., "The promises and pitfalls of RNA interference-based therapeutics", Nature 457:426-433 (2009).
Chabert et al., "Multiple welding of long fiber epoxy vitrimer composites." Soft Matter 12:4838-4845 (2016).
Chang et al., "Surface-Engineered Dendrimers with a Diaminododecane Core Achieve Efficient Gene Transfection and Low Cytotoxicity," Bioconjugate Chemistry 25(2):342-50. Jan. 21, 2014).
Chawla et al., Biodegradable and biocompatible synthetic saccharide-Peptide hydrogels for three-dimensional stem cell culture. Biomacromolecules 12:560e7 (2011).
Chawla et al., Modulation of chondrocyte behavior through tailoring functional synthetic saccharide-peptide hydrogels. Biomaterials 33:6052e60 (Sep. 1, 2012).
Chen et al., "Bioreducible Hyperbranched Poly(amido amine)s for Gene Delivery," Biomacromolecules 10:2921-2927 (2009).
Chen et al., "An RNA interference screen uncovers a new molecule in stemcell self-renewal and long-term regeneration", Nature 485(7396): 104-108 (2012).
Cordero Garcia, Marcela M. Non-final Office Action for U.S. Appl. No. 14/186,973 (dated Mar. 24, 2015).
Cordero Garcia, Marcela M. Final Office Action for U.S. Appl. No. 14/186,973 (dated Aug. 21, 2015).
Cordero Garcia, Marcela M. Notice of Allowance for U.S. Appl. No. 14/186,973 (dated Nov. 12, 2016).
Creusat et al., "Self-Assembling Polyethylenimine Derivatives Mediate Efficient siRNA Delivery in Mammalian Cells," Chembiochem 9:2787-2789 (2008).
Crombez et al., "A New Potent Secondary Amphipathic Cell-penetrating Peptide for siRNA Delivery Into Mammalian Cells," Molecular Therapy 17(1):95-103 (2009).
Crombez et al., "Targeting cyclin B1 through peptide-based delivery of siRNA prevents tumour growth," Nucleic Acids Res 37(14):4559-4569 (2009).
Cromwell et al., "Malleable and Self-Healing Covalent Polymer Networks through Tunable Dynamic Boronic Ester Bonds." J. Am. Chem. Soc. 137:6492-6495 (2015).
Cui et al., "Conjugation Chemistry through Acetals toward a Dextran-Based Delivery System for Controlled Release of siRNA," J Am Chem Soc 134:15840 (Sep. 2012).
Dafik et al., "Fluorinated Lipid Constructs Permit Facile Passage of Molecular Cargo into Living Cells," JACS 131:12091-12093 (2009).
Davis et al., "Evidence of RNAi in humans from systemically administered siRNA via targeted nanoparticles," Nature 464:1067-1071 (2010).
Debus et al., "Delivery of messenger RNA using poly(ethylene imine)-poly(ethylene glycol)-copolymer blends for polyplex formation: Biophysical characterization and in vitro transfection properties". 148:334-343 (2010).
Deering et al., "Nucleic acid vaccines: prospects for non-viral delivery of mRNA vaccines". Expert Opinion on Drug Delivery 11(6):885-899 (2014).
Deforest et al., "Sequential click reactions for synthesizing and patterning three-dimensional cell microenvironments." Nat. Mater. 8:659-664 (2009).
Degoricija et al., "Hydrogels for osteochondral repair based on photocrosslinkable carbamate dendrimers. Biomacromolecules." 9:2863-2872 (2008).
Denissen et al., "Vinylogous Urethane Vitrimers." Adv. Funct. Mater. 25(16):2451-2457 (2015).
Denissen et al., "Vitrimers: permanent organic networks with glass-like fluidity." Chem. Sci. 7:30-38 (2016).
Denoyelle et al., "Synthesis and preliminary biological studies of hemifluorinated bifunctional bolaamphiphiles designed for gene delivery," New Journal of Chemistry 30:629-646 (2006).
Dietzl et al., "A genome-wide transgenic RNAi library for conditional gene inactivation in *Drosophila*", Nature 448:151-156 (2007).
Discher et al., Tissue cells feel and respond to the stiffness of their substrate. Science 310:1139-1143 (2005).
Dong et al., "Lipopeptide nanoparticles for potent and selective siRNA delivery in rodents and nonhuman primates", PNAS 111(11):3955-3960 (Mar. 18, 2014).
Drury et al., Hydrogels for tissue engineering: scaffold design variables and applications. J. Biomaterials 24:4337-4351 (2003).
Dunn et al., "Reductively-responsive siRNA-conjugated hydrogel nanoparticles for gene silencing," J Am Chem Soc 134:7423-7430 (May 2012).
Eguchi et al., "siRNA delivery using peptide transduction domains." Cell 30(7):341-345 (2009).
Elbert et al., Conjugate addition reactions combined with free-radical cross-linking for the design of materials for tissue engineering. Biomacromolecules 2:430-441 (2001).
Engler et al., Matrix elasticity directs stem cell lineage specification. Cell 126:677-689 (2006).
Fabio et al., "Novel Galactosylated Polyamine Bolaamphiphiles for Gene Delivery," Bioconjugate Chemistry 14:358-367 (2003)v.
Fischer et al., "Dendritic Polyglycerols with Oligoamine Shells Show Low Toxicity and High siRNA Transfection Efficiency in Vitro," Bioconjug Chem 21:1744-1752 (2010).
Flanagan et al., Neurite branching on deformable substrates. NeuroReport 13: 2411-2415 (2002).
Fortman et al., "Mechanically Activated, Catalyst-Free Polyhydroxyurethane Vitrimers." J. Am. Chem. Soc. 137:14019-14022 (2015).
Fougerolles et al., "Interfering with disease: a progress report on siRNA-based therapeutics", Nat. Rev. Drug Discovery 6:443-410 (2007).
Frisch et al., Anoikis mechanisms. Curr Opin Cell Biol 13:555e62 (2001).
Gaucheron et al., "In Vitro Gene Transfer with a Novel Galactosylated Spermine Bolaamphiphile," Bioconjugate Chem. 12:569-575 (2001).
Gelain et al., Designer self-assembling peptide nanofiber scaffolds for adult mouse neural stem cell 3-dimensional cultures. S. PLoS One 1:e119 (2006).
Giljohann et al., "Gene Regulation with Polyvalent siRNA-Nanoparticle Conjugates," JACS 131(6):2072-2073 (2009).
Gilleron et al., "Image-based analysis of lipid nanoparticle-mediated siRNA delivery, intracellular trafficking and endosomal escape" Nature Biotechnology 31:638-646 (2013).
Gossl et al., "Molecular Structure of Single DNA Complexes with Positively Charged Dendronized Polymers." J. Am. Chem. Soc. 124:6860-6865 (2002).
Grieshaber et al., Synthesis and Characterization of Elastin-Mimetic Hybrid Polymers with Multiblock, Alternating Molecular Architecture and Elastomeric Properties. Macromolecules 42:2532-2541(2009).
Guignard et al., "Cost Analysis of Human Islet Transplantation for the Treatment of Type 1 Diabetes in the Swiss-French Consortium GRAGIL." Diabetes Care ,27(4):895-900 (2004).
Guilak et al., Control of stem cell fate by physical interactions with the extracellular matrix. Cell Stem Cell 5, 17-26 (2009).v.
Hafez et al., "On the mechanism whereby cationic lipids promote intracellular delivery of polynucleic acids" Nature 8:1188-1196 (2001).
Haines-Butterick et al., "Controlling hydrogelation kinetics by peptide design for three-dimensional encapsulation and injectable delivery of cells." Proc. Natl. Acad. Sci. U.S.A. 104:7791-7796 (2007).
Hamley, Ian. "PEG-Peptide Conjugates." Biomacromolecules 15:1543-1559 (2014).
Hartgerink et al., "Self-Assembly and Mineralization of Peptide-Amphiphile Nanofibers", Science 294:1684-1688 (2010).
Hiemstra et al., Rapidly in situ forming biodegradable robust hydrogels by combining stereocomplexation and photopolymerization. J. Am. Chem. Soc. 129:9918-9926 (2007).
Hodges et al., "Hydrodynamic delivery of DNA". Expert Opinion on Biological Therapy 3(6):911-918 (2003).
Hu et al., Rational design of transglutaminase substrate peptides for rapid enzymatic formation of hydrogels. J. Am. Chem. Soc. 125, 14298-14299 (2003).

(56) References Cited

OTHER PUBLICATIONS

Hu et al., Hydrogels cross-linked by native chemical ligation. Biomacromolecules 2194-2200 (2009).

Hunter, "Molecular hurdles in polyfectin design and mechanistic background to polycation induced cytotoxicity", Adv. Drug Delivery Rev 58:1523-1531 (2006).

Hwang et al., Cartilage tissue engineering: Directed differentiation of embryonic stem cells in three-dimensional hydrogel culture. J. Methods Mol. Biol. 407:351-373 (2007).

Ingber et al., Cell structure and hierarchical systems biology. J. Cell Sci. 116:1157-1173 (2003).

Inukai et al., Preparation and characterization of hyaluronate-hydroxyethyl acrylate blend hydrogel for controlled release device. Chem. Pharm. Bull. 48:850-854 (2000).

Ito et al., "Mesechymal Stem Cell and Islet Co-Transplantation Promotes Graft Revascularization and Function", Transplantation, 89(12):1438-1445 (Jun. 28, 2010).

Jain et al., "Lactose-ornithine bolaamphiphiles for efficient gene delivery in vitro", International Journal of Pharmaceutics 423:392-400 3 (2012).

Jun et al., Biomimetic self-assembled nanofibers Soft Matter 2:177-181 (2006).

Kersey et al., A hybrid polymer gel with controlled rates of cross-link rupture and self-repair J. R. Soc. Interface 4:373-380 (2007).

Khalil et al., "Uptake Pathways and Subsequent Intracellular Trafficking in Nonviral Gene Delivery," Pharmacological Reviews 58(1):32-45 (2006).

Khan et al., "Diaminododecane-based cationic bolaamphiphile as a non-viral gene delivery", Biomaterials 33 , 4673-4680 (2012).

Kim et al., "Polyoxalate Nanoparticles as a Biodegradable and Biocompatible Drug Delivery Vehicle," Biomacromolecules 11: 555-560 (2010).

Kim et al., "Dendronized gold nanoparticles for siRNA delivery" Small 8(21):3253-3256 (2012).

Kim et al., "In Silico, In Vitro, and In Vivo Studies Indicate the Potential Use of Bolaamphiphiles for Therapeutic siRNAs Delivery", Molecular Therapy—Nucleic Acids 2:e80 (2013).

Klein et al., "Nucleic acid transfer with hemifluorinated polycationic lipids" Biomaterials 31:4781-4788 (2010).

Kleinman et al., "Isolation and characterization of type IV procollagen, laminin, and heparan sulfate proteoglycan from the EHS sarcoma." Biochemistry 21:6188-6193 (1982).

Kloxin et al., "Covalent Adaptable Networks (CANs): A Unique Paradigm in Crosslinked Polymers." Macromolecules 43(6):2643-2653 (2010).

Kloxin et al., "Mechanophotopatterning on a Photoresponsive Elastomer." Adv. Mater 23:1977-1981 (2011).

Knudsen et al., "In vivo toxicity of cationic micelles and liposomes" Nanomedicine 11(2):467-477 (Aug. 26, 2014).

Kopecek, Hydrogel Biomaterials: A Smart Future? J. Biomaterials 28:5185-5192 (2007).

Kulkarni et al., "Pendant Polymer:Amino-β-Cyclodextrin:siRNA Guest:Host Nanoparticles as Efficient Vectors for Gene Silencing," J Am Chem Soc 134:7596-7599 (Apr. 30, 2012).

Kumar et al., "Transvascular delivery of small interfering RNA to the central nervous system", Nature 448:39-43 (2007).

Lee et al., "Controlling Mechanical and Swelling Properties of Alginate Hydrogels Independently by Cross-Linker Type and Cross-Linking Density." Macromolecules 33, 4291-4294 (2000).

\* cited by examiner

A

| Denpol | d (nm) | PDI | ZP (mV) |
|---|---|---|---|
| G2 3:1 | 140 | 0.31 | -8.3 |
| G2 2:1 | 163 | 0.30 | -6.3 |
| G2 3.0 PEG2k 2:1 | 106 | 0.22 | -2.1 |
| G2 1.5 PEG2k 2:1 | 136 | 0.21 | -7.8 |
| G2 1.0 PEG2k 2:1 | 155 | 0.29 | -8.0 |
| G2 25 TEG 3:1 | 126 | 0.35 | -10.1 |
| G2 25 TEG 2:1 | 160 | 0.28 | -7.5 |
| G2 50 TEG 3:1 | 153 | 0.23 | -8.6 |
| G2 50 TEG 2:1 | 131 | 0.19 | -9.2 |
| G2 75 TEG 3:1 | 180 | 0.24 | -10.1 |
| G2 75 TEG 2:1 | 191 | 0.32 | -13.4 |

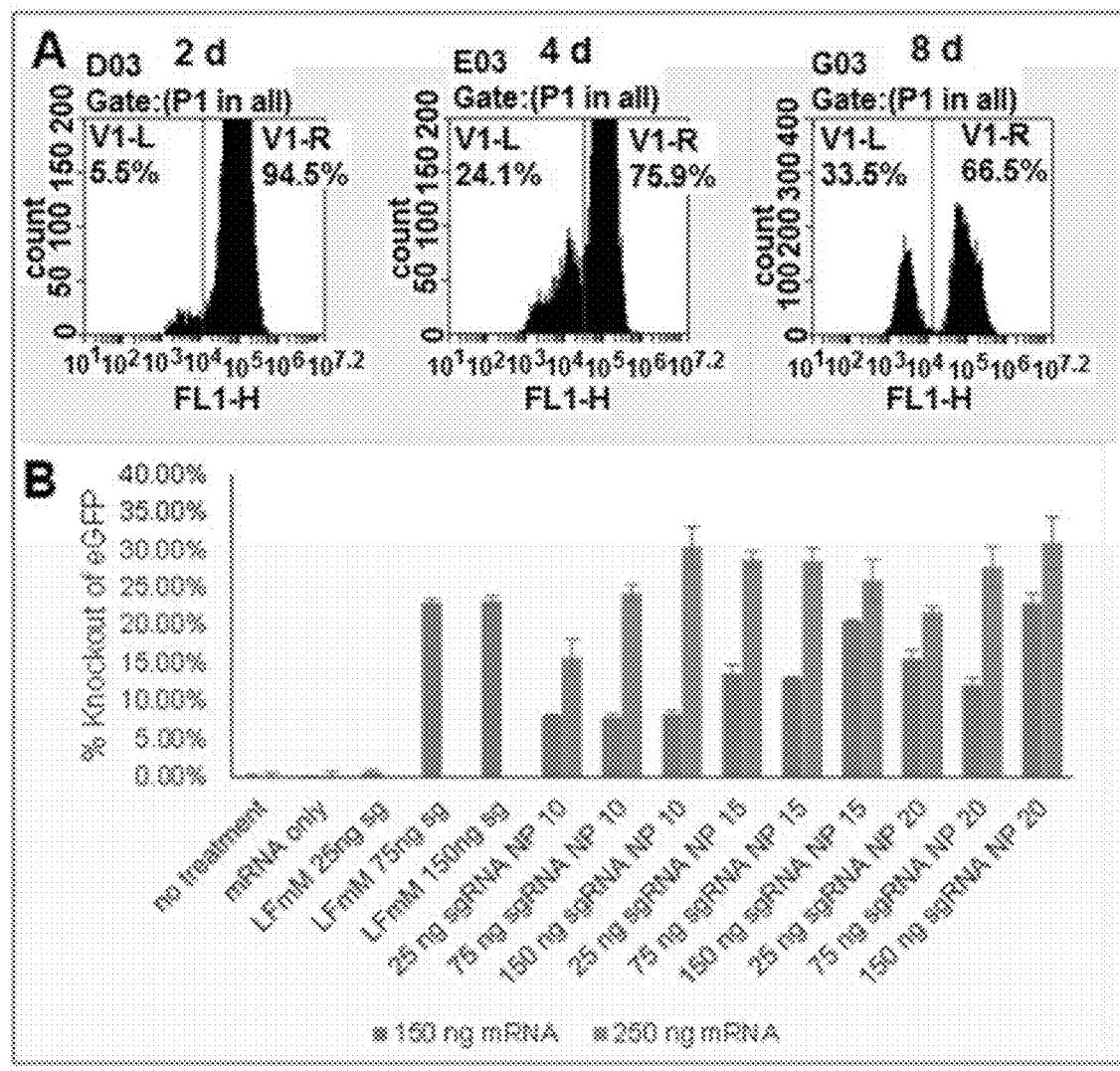
FIG. 54A-B

BIODEGRADABLE VECTORS FOR EFFICIENT RNA DELIVERY

CROSS REFERENCE TO RELATED APPLICATIONS

This application claims priority under 35 U.S.C. § 119 from Provisional Application Ser. No. 62/307,480 filed Mar. 12, 2016, the disclosure of which is incorporated herein by reference.

STATEMENT OF GOVERNMENT SUPPORT

This application is a U.S. National Stage Application filed under 35 U.S.C. § 371 and claims priority to International Application No. PCT/US2017/021978, filed Mar. 10, 2017, which application claims priority under 35 U.S.C. § 119 from Provisional Application Ser. No. 62/307,480 filed Mar. 12, 2016, the disclosures of which are incorporated herein by reference in their entirety.

TECHNICAL FIELD

The disclosure provides for biodegradable vectors, and methods of using the vectors for efficiently delivering messenger RNA and/or ssRNA into cells.

BACKGROUND

Originally thought to be too instable and immunogenic for the treatment of diseases, messenger RNA (mRNA) has reemerged as a promising therapeutic for cancers, infections, and stem-cell therapy. In accordance, the demand and applicability for synthetic vectors tailored to mRNA delivery has also increased greatly. Much like other nucleic acids, mRNA is a large anionic polymer and does not readily pass through the cell membrane unassisted. However, since mRNA only requires delivery to the cellular cytoplasm, it avoids the drawbacks of protein expression via plasmid DNA (pDNA) or viral vector delivery (e.g. insertive mutagenesis, delivery to nucleus.) Recently, synthetic nucleic acid delivery vectors (liposomes, cationic polymers) as well as physical delivery methods have been shown to effectively deliver mRNA to the cytoplasm, but are understudied compared to siRNA and pDNA delivery methods.

SUMMARY

The disclosure provides for biodegradable vectors that have been specifically designed to deliver mRNA and/or ssRNA into cells. The vectors disclosed herein are capable of forming stable and favorable complexes with mRNA and/or ssRNA without forming aggregates. Moreover, the vectors allow for effective delivery of mRNA and/or ssRNA into cells.

In a particular embodiment, the disclosure provides for a complex that comprises: (a) one or more mRNAs and/or ssRNAs and (b) a vector comprising a structure of Formula I:

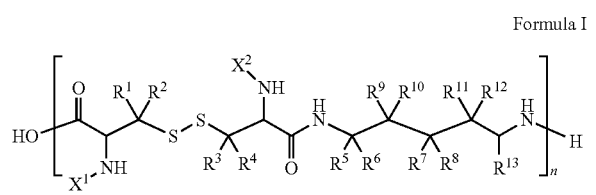

Formula I wherein, n is an integer greater than 5; $R^1$-$R^{12}$ are independently selected from the group comprising H, optionally substituted ($C_1$-$C_6$)-alkyl, optionally substituted ($C_1$-$C_6$)-heteroalkyl, optionally substituted ($C_1$-$C_6$)-alkenyl, optionally substituted ($C_1$-$C_6$)-heteroalkenyl, optionally substituted ($C_1$-$C_6$)-alkynyl, optionally substituted ($C_1$-$C_6$)-heteroalkynyl, optionally substituted ($C_3$-$C_{12}$)cycloalkyl, optionally substituted ($C_4$-$C_{12}$)cycloalkenyl, optionally substituted aryl, optionally substituted heterocycle, halide, hydroxyl, carbonyl, aldehyde, carboxyl, ester, alkoxy, carboxyamide, amine, imine, azide, cyano, nitro, nitroso, thiol, sulfide, sulfoxide, sulfone, and phosphate; $R^{13}$ is an ester; $X^1$-$X^2$ are independently selected from a polyoxyalkylene polymer and an optionally substituted L-lysine based dendron that is functionalized on the outer layer by comprising histidine and tryptophan moieties; and wherein at least one of $X^1$-$X^2$ is an optionally substituted L-lysine based dendron and wherein at least one of $X^1$-$X^2$ is a polyoxyalkylene polymer, and wherein the ratio of histidine to tryptophan moieties is 2.5:1 to 1:1. In the further embodiment, the disclosure provides for a complex that comprises a structure of Formula I(a):

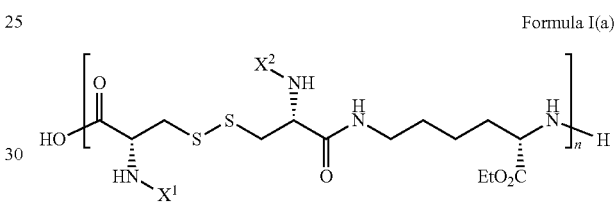

Formula I(a)

wherein, n is an integer greater than 50; $X^1$-$X^2$ are independently selected from the group consisting of: (i) a structure of Formula II:

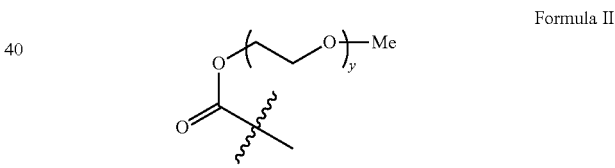

Formula II wherein y is an integer of 3 or greater, and (ii) a structure of Formula III:

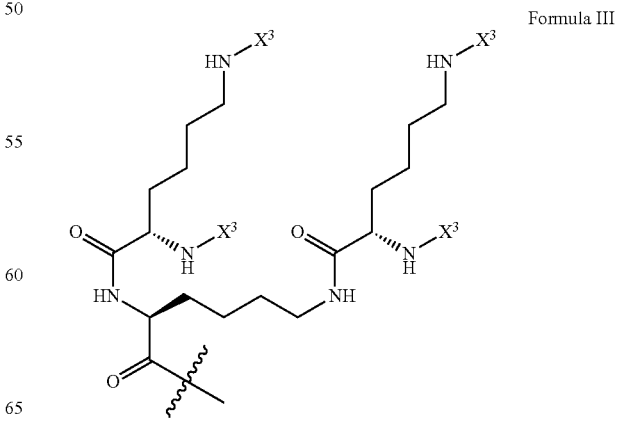

Formula III where $X^3$ is a histidine moiety or a tryptophan moiety; and wherein at least one of $X^1$-$X^2$ has the structure of Formula II and wherein at least one of $X^1$-$X^2$ has the structure of Formula III, and wherein the ratio of histidine to tryptophan moieties is 2.5:1 to 1:1. In another embodiment, y is 3. In an alternate embodiment, y is >3. In a further embodiment and in any embodiment described above, the ratio of histidine to tryptophan moieties is 2:1. In yet a further embodiment and in any embodiment described above, the molar ratio of protonated amines of the dendronized polymer:phosphates of the mRNAs and/or ssRNAs (N:P) is from 5 to 20. In a certain embodiment and in any embodiment described above, the N:P ratio is from 10 to 15. In another embodiment and in any embodiment described above, the N:P ratio is about 10. In yet another embodiment and in any embodiment described above, the one or more mRNAs and/or ssRNAs comprise at least 100 ribonucleotides. In a further embodiment and in any embodiment described above, the one or more mRNAs and/or ssRNAs comprise from 100 to 20,000 ribonucleotides. In yet a further embodiment and in any embodiment described above, the dendronized polymer further comprises a targeting ligand. Examples of targeting ligand include but are not limited to (a) antibodies, (b) aptamers, (c) cholesterol and its derivatives, (d) folate compounds or folate conjugates, (e) transferrin, (f) saccharides and (g) cell-penetrating peptides. In another embodiment and in any embodiment described above, the one or more mRNAs and/or ssRNAs encode a peptide or protein antigen isolated from a tumor. In yet another embodiment and in any embodiment described above, at least a portion of the one or more mRNAs and/or ssRNAs comprises modified ribonucleotides in the place of naturally occurring ribonucleotides, wherein the modified ribonucleotides have a nucleobase selected from the group consisting of pseudouridine, 5-methyluridine, 2-thiouridine, 5-methylcytidine (m5C), and N6-methyladenosine.

In a particular embodiment, the disclosure provides a method of delivering one or more mRNA and/or ssRNAs into a cell comprising: contacting a cell with a complex described herein and above. In a further embodiment, the cell is contacted in vitro. In an alternate embodiment, the cell is contacted in vivo. In a certain embodiment and in any embodiment described above, the cell is a cancer cell. In another embodiment and in any embodiment described above, the cell is a human cell.

In a certain embodiment, the disclosure also provides a method of promoting prophylactic or therapeutic antitumor immunity in a subject comprising administering a complex herein to a subject, wherein the complex is delivered ex vivo or in vivo. In a further embodiment, the subject is a human subject.

In a particular embodiment, the disclosure provides a method of editing a genome of a cell comprising contacting the cell with the complex disclosed herein, wherein the one or more mRNAs and/or ssRNAs comprise cas9 mRNA and an sgRNA.

The details of one or more embodiments of the disclosure are set forth in the accompanying drawings and the description below. Other features, objects, and advantages will be apparent from the description and drawings, and from the claims.

$^1$H NMR (600 MHz, CD$_3$OD) δ 4.64-4.50 (m, 0.65H), 4.50-4.32 (m, 1.54H), 4.32-4.10 (m, 4.12H), 4.10-3.96 (m, 0.54H), 3.87-3.49 (m, 16.84H), 3.28-3.10 (m, 3.46H), 3.10-2.83 (m, 2.25H), 2.04-1.82 (m, 1.78H), 1.84-1.66 (m, 1.77H), 1.66-1.34 (m, 4.66H), 1.34-1.10 (m, 3H).

Figure 17:
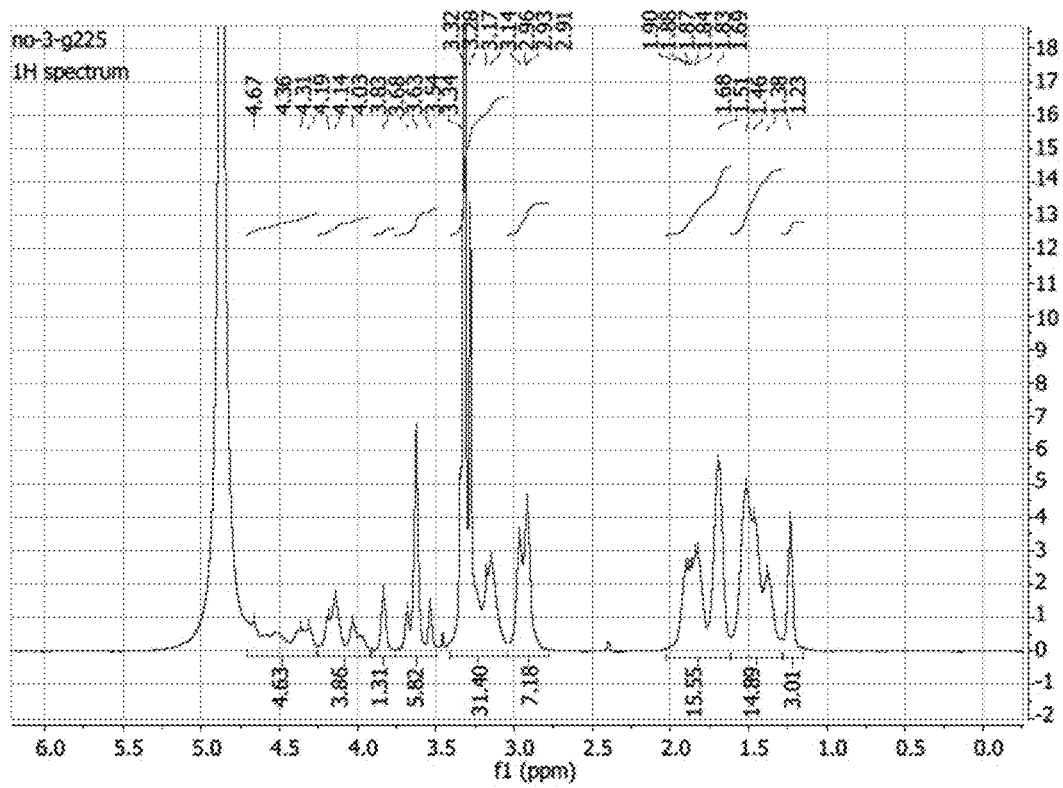

FIG. 17 provides a $^1$HNMR spectra of a denpol comprising a G2 TEG 25. $^1$H NMR (500 MHz, CD$_3$OD) δ 4.69-4.26 (m, 4H), 4.25-4.08 (m, 3H), 4.08-3.90 (m, 1H), 3.90-3.76 (m, 1H), 3.76-3.49 (m, 6H), 3.44-3.03 (m, 32H), 3.04-2.77 (m, 7H), 2.06-1.76 (m, 8H), 1.76-1.60 (m, 8H), 1.60-1.28 (m, 15H), 1.28-1.15 (m, 3H).

Figure 18:
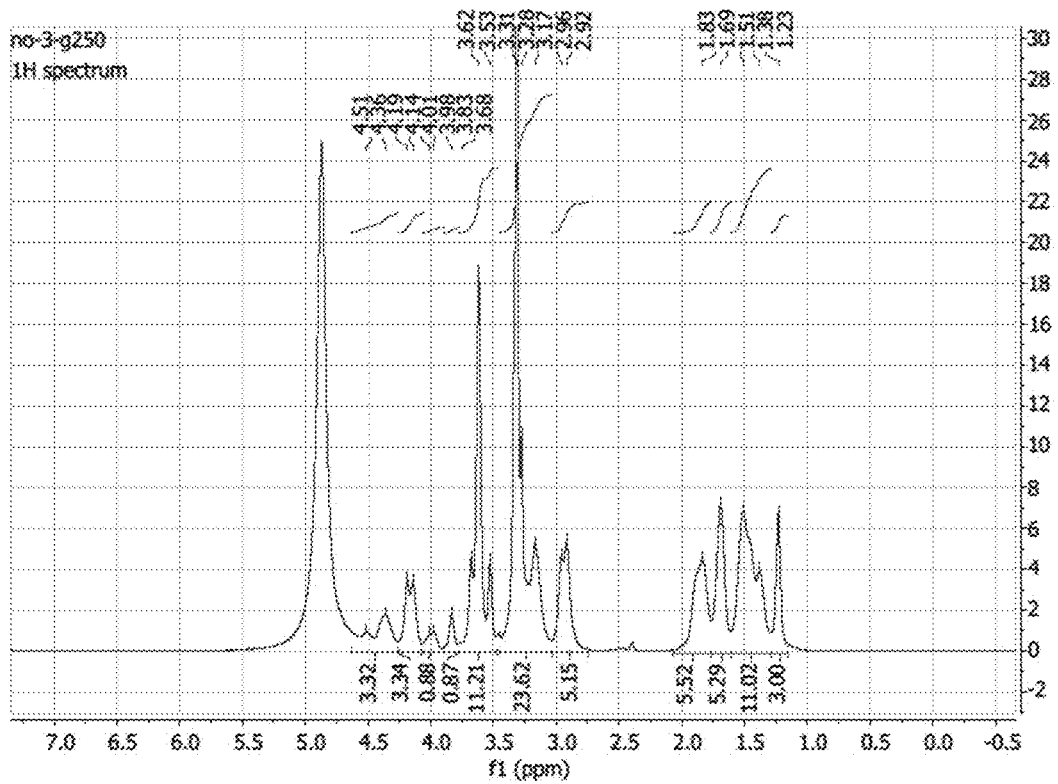

FIG. 18 provides a $^1$HNMR spectra of a denpol comprising a G2 TEG 50. $^1$H NMR (500 MHz, CD$_3$OD) δ 4.63-4.46 (m, 1H), 4.46-4.27 (m, 2H), 4.27-4.07 (m, 3H), 4.07-3.90 (m, 1H), 3.90-3.78 (m, 1H), 3.75-3.47 (m, 11H), 3.45-3.04 (m, 24H), 3.03-2.75 (m, 5H), 2.07-1.76 (m, 5H), 1.76-1.61 (m, 5H), 1.61-1.29 (m, 11H), 1.29-1.15 (m, 3H).

Figure 19:
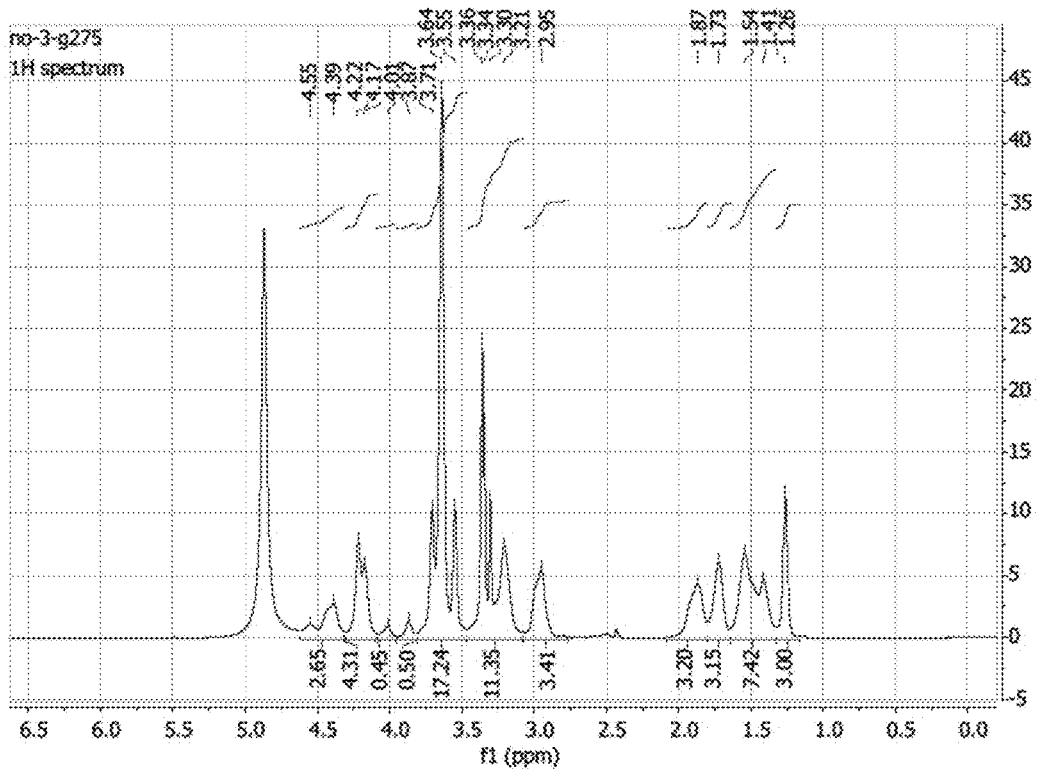

FIG. 19 provides a $^1$HNMR spectra of a denpol comprising a G2 TEG 75. $^1$H NMR (500 MHz, CDCl$_3$) δ 4.62-4.49 (m, 1H), 4.49-4.30 (m, 2H), 4.30-4.09 (m, 4H), 4.09-3.94 (m, 1H), 3.94-3.80 (m, 1H), 3.83-3.48 (m, 17H), 3.48-3.09 (m, 11H), 3.09-2.83 (m, 3H), 2.06-1.81 (m, 3H), 1.80-1.65 (m, 3H), 1.65-1.33 (m, 7H), 1.33-1.18 (m, 3H).

Figure 20:
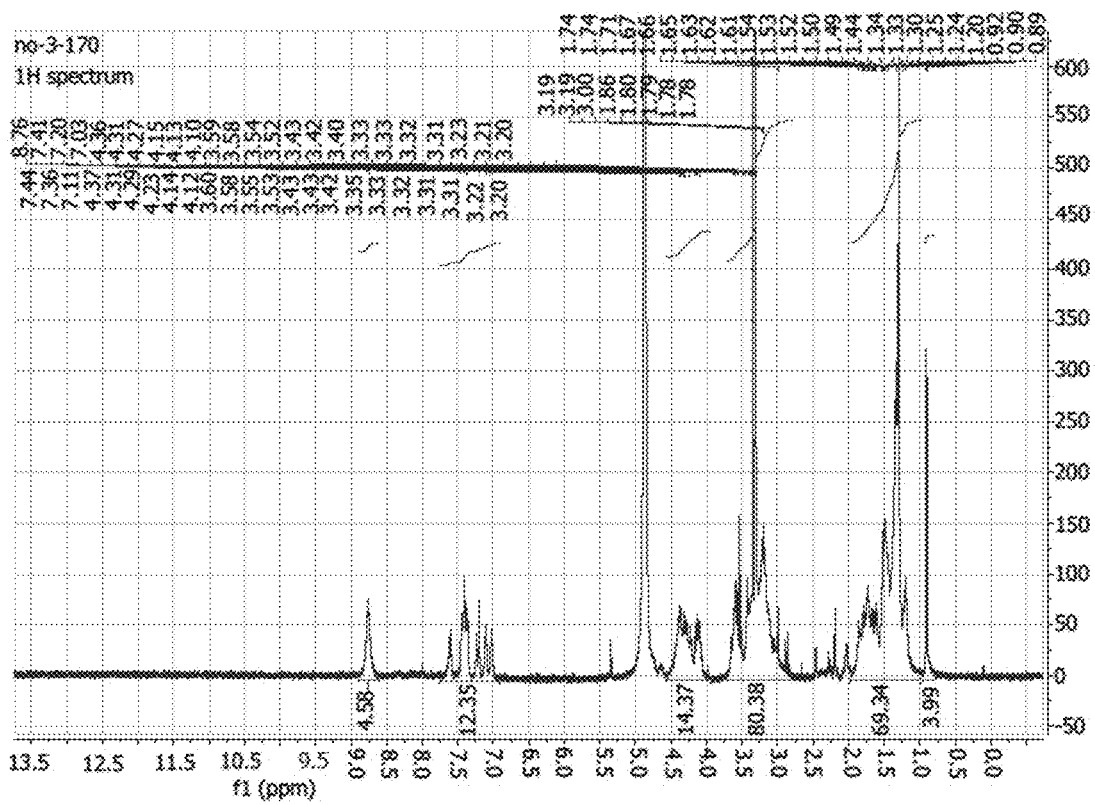

FIG. 20 provides a $^1$HNMR spectra of a denpol comprising a G2 25 TEG 3:1 (74 H 26 W). $^1$H NMR (600 MHz, CD$_3$OD) δ 8.91-8.57 (m, 5H), 7.74-6.93 (m, 12H), 4.59-3.95 (m, 14H), 3.78-2.72 (m, 80H), 1.93-1.00 (m, 69H).

Figure 21:
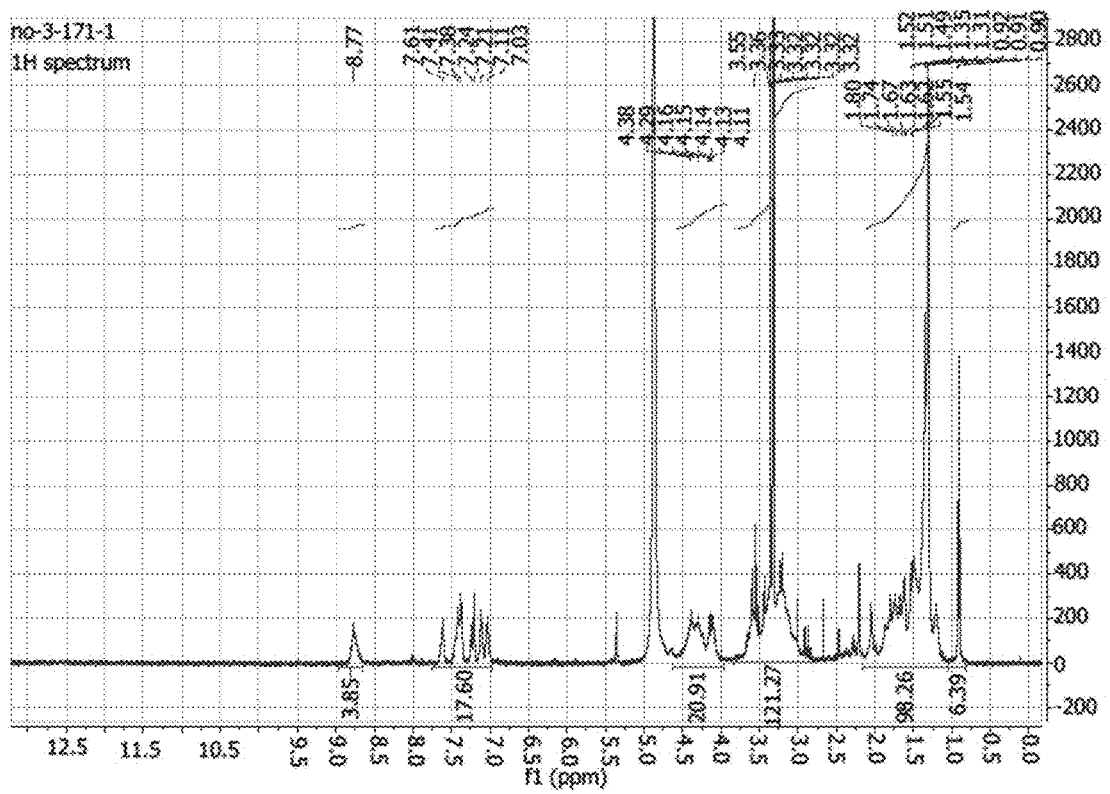

FIG. 21 provides a $^1$HNMR spectra of a denpol comprising a G2 25 TEG 2:1 (63 H 32 W). $^1$H NMR (600 MHz, CD$_3$OD) δ 8.94-8.58 (m, 4H), 7.73-6.92 (m, 18H), 4.59-3.95 (m, 21H), 3.80-2.74 (m, 120H), 2.16-1.02 (m, 98H).

Figure 22:
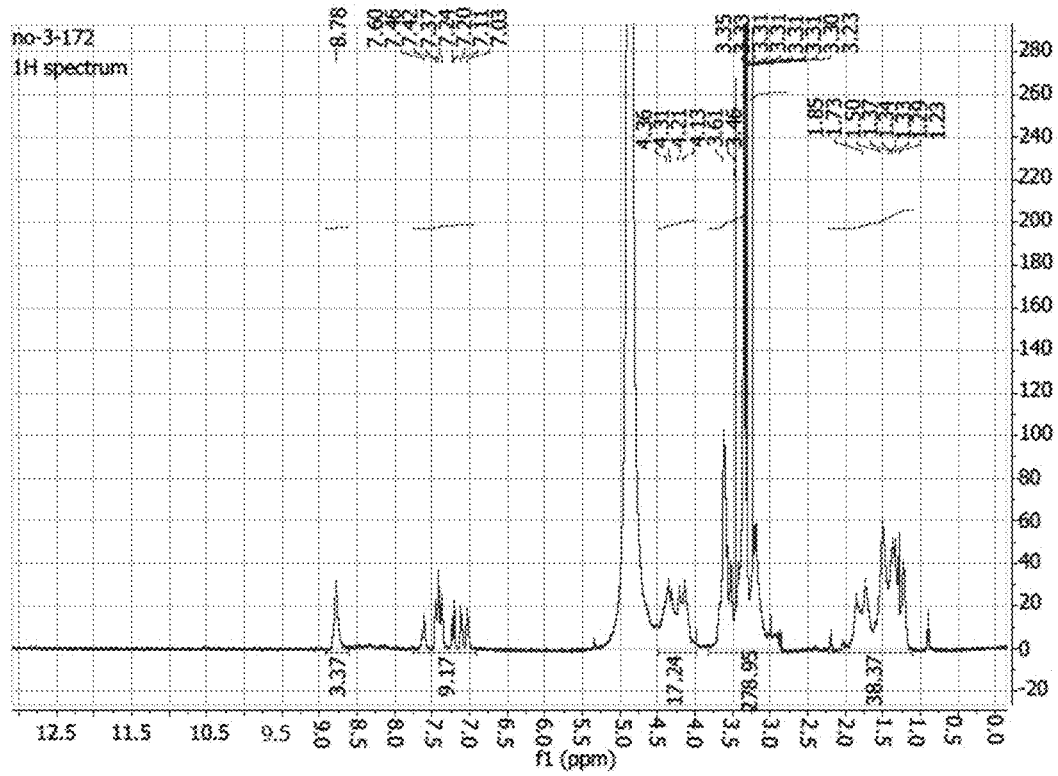

FIG. 22 provides a $^1$HNMR spectra of a denpol comprising a G2 50 TEG 3:1 (73 H 27 W). $^1$H NMR (600 MHz, CD$_3$OD) δ 8.89-8.62 (m, 3H), 7.72-6.94 (m, 9H), 4.52-3.96 (m, 18H), 3.80-2.79 (m, 278H), 2.09-1.10 (m, 38H).

Figure 23:
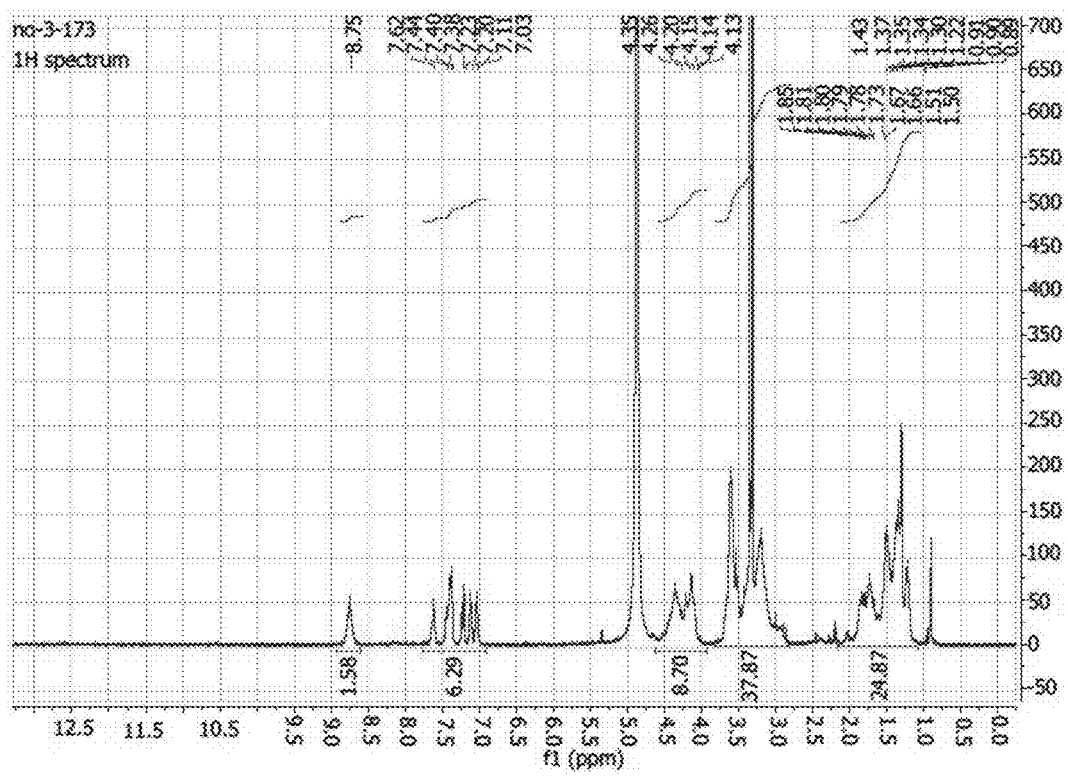

FIG. 23 provides a $^1$HNMR spectra of a denpol comprising a G2 50 TEG 2:1 (64 H 36 W). $^1$H NMR (600 MHz, CD$_3$OD) δ 8.91-8.60 (m, 3H), 7.72-6.94 (m, 12H), 4.60-3.92 (m, 16H), 3.85-2.73 (m, 71H), 2.15-1.04 (m, 47H).

Figure 24:
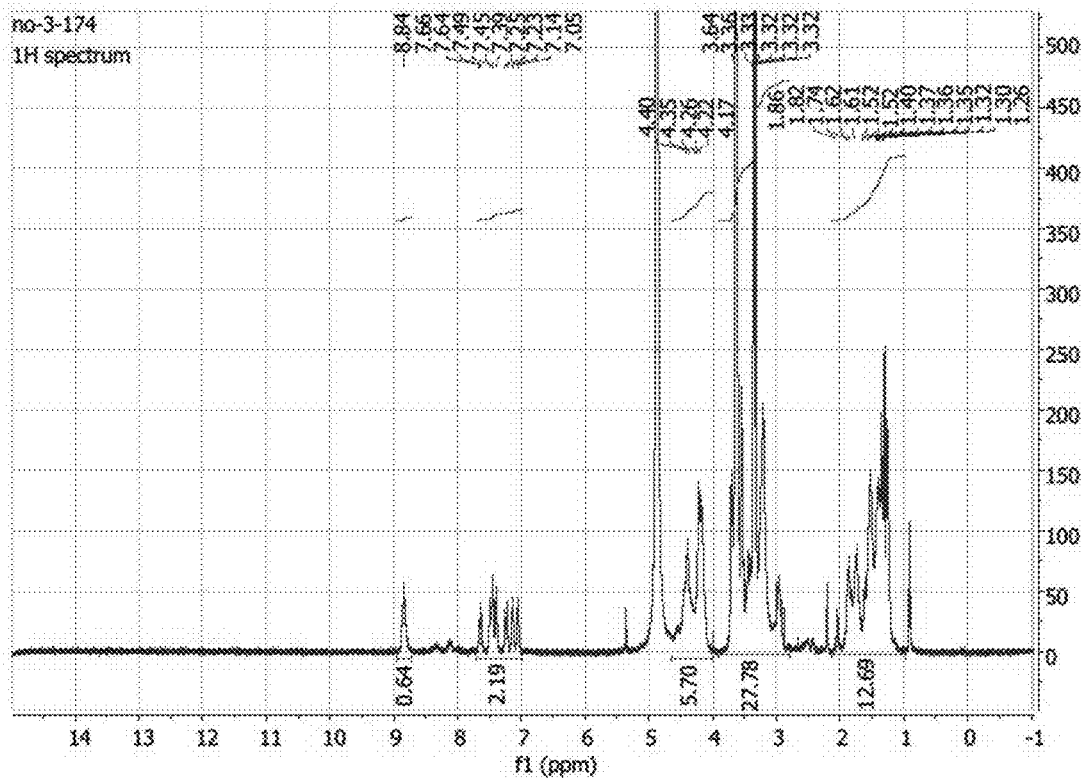

FIG. 24 provides a $^1$HNMR spectra of a denpol comprising a G2 75 TEG 3:1 (71 H 29 W). $^1$H NMR (600 MHz, CD$_3$OD) δ 8.93-8.69 (m, 2H), 7.75-7.00 (m, 7H), 4.63-4.02 (m, 18H), 3.86-2.78 (m, 91H), 2.11-1.07 (m, 41H).

Figure 25:
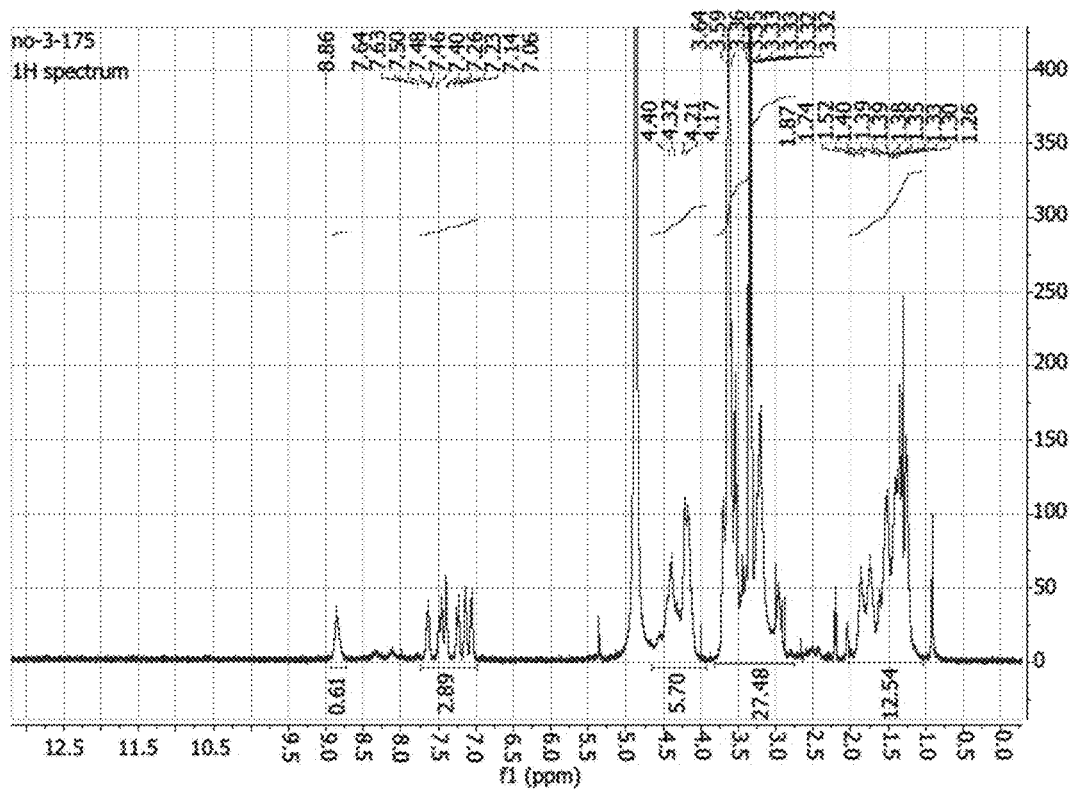

FIG. 25 provides a $^1$HNMR spectra of a denpol comprising a G2 75 TEG 2:1 (61 H 39 W). $^1$H NMR (600 MHz, CD$_3$OD) δ 9.01-8.71 (m, 2H), 7.76-6.97 (m, 8H), 4.69-3.96 (m, 16H), 3.83-2.77 (m, 75H), 2.10-1.01 (m, 35H).

Figure 26:
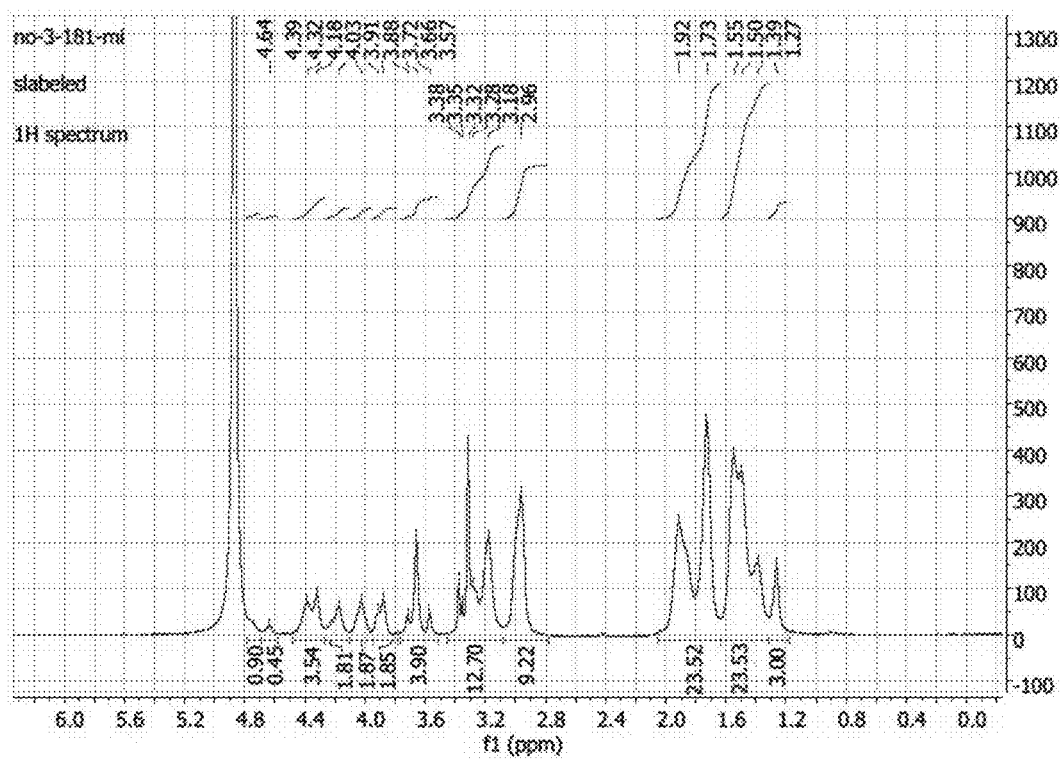

FIG. 26 provides a $^1$HNMR spectra of a denpol comprising a G3 25 TEG Backbone. $^1$H NMR (600 MHz, CD$_3$OD) δ 4.78-4.69 (m, 1H), 4.69-4.59 (m, 1H), 4.48-4.27 (m, 3H), 4.27-4.11 (m, 2H), 4.10-3.96 (m, 2H), 3.96-3.82 (m, 2H), 3.76-3.52 (m, 4H), 3.44-3.08 (m, 12H), 3.08-2.80 (m, 9H), 2.06-1.63 (m, 23H), 1.63-1.32 (m, 23H), 1.32-1.15 (m, 3H).

Figure 27:
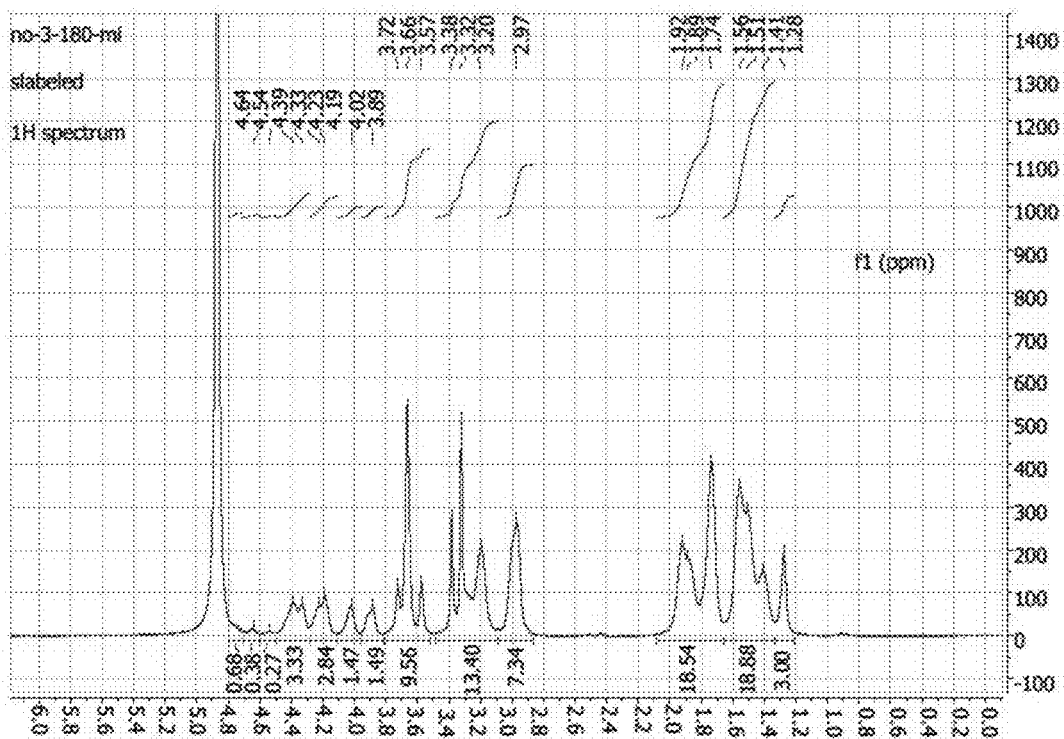

FIG. 27 provides a $^1$HNMR spectra of a denpol comprising a G3 50 TEG Backbone. $^1$H NMR (600 MHz, CD$_3$OD) δ 4.79-4.70 (m, 1H), 4.69-4.49 (m, 1H), 4.52-4.28 (m, 3H), 4.28-4.11 (m, 3H), 4.11-3.97 (m, 1H), 3.97-3.81 (m, 2H), 3.81-3.53 (m, 9H), 3.48-3.09 (m, 13H), 3.09-2.87 (m, 7H), 2.07-1.65 (m, 19H), 1.65-1.33 (m, 19H), 1.33-1.22 (m, 3H).

Figure 28:
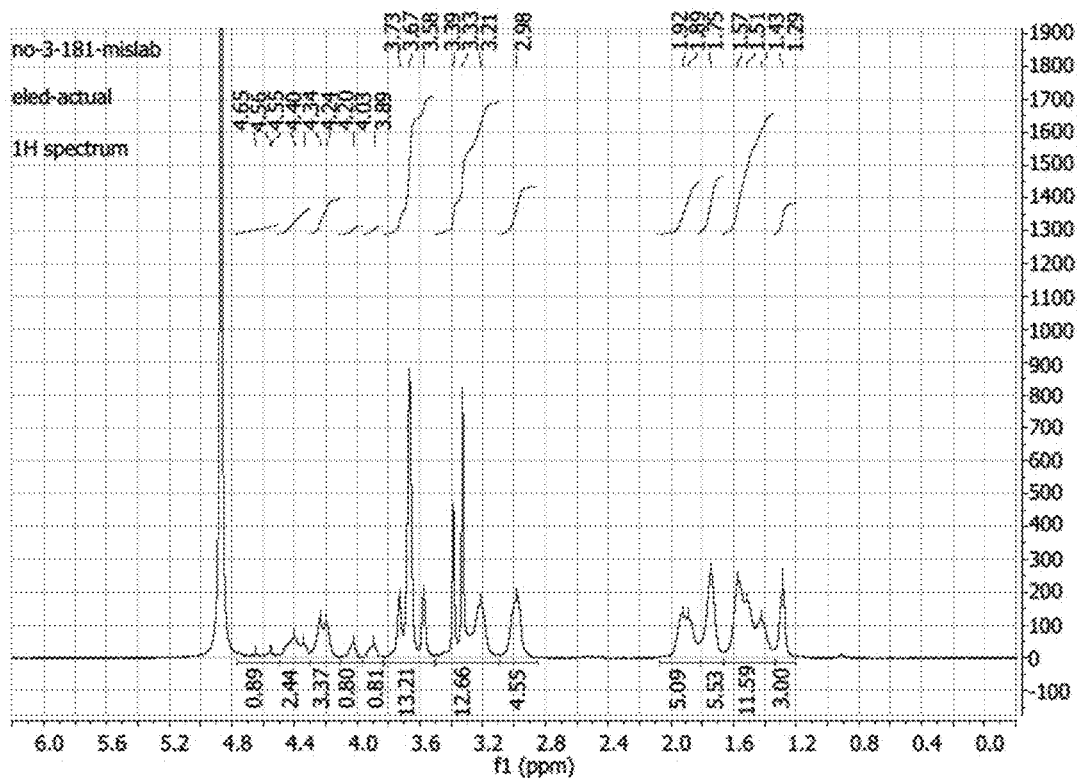

FIG. 28 provides a $^1$HNMR spectra of a denpol comprising a G3 75 TEG Backbone. $^1$H NMR (600 MHz, CD$_3$OD) δ 4.72-4.51 (m, 1H), 4.51-4.30 (m, 2H), 4.30-4.12 (m, 3H), 4.12-3.97 (m, 1H), 3.97-3.84 (m, 1H), 3.83-3.52 (m, 13H), 3.47-3.11 (m, 12H), 3.09-2.85 (m, 4H), 2.05-1.82 (m, 5H), 1.81-1.67 (m, 5H), 1.68-1.34 (m, 11H), 1.35-1.21 (m, 3H).

Figure 29:
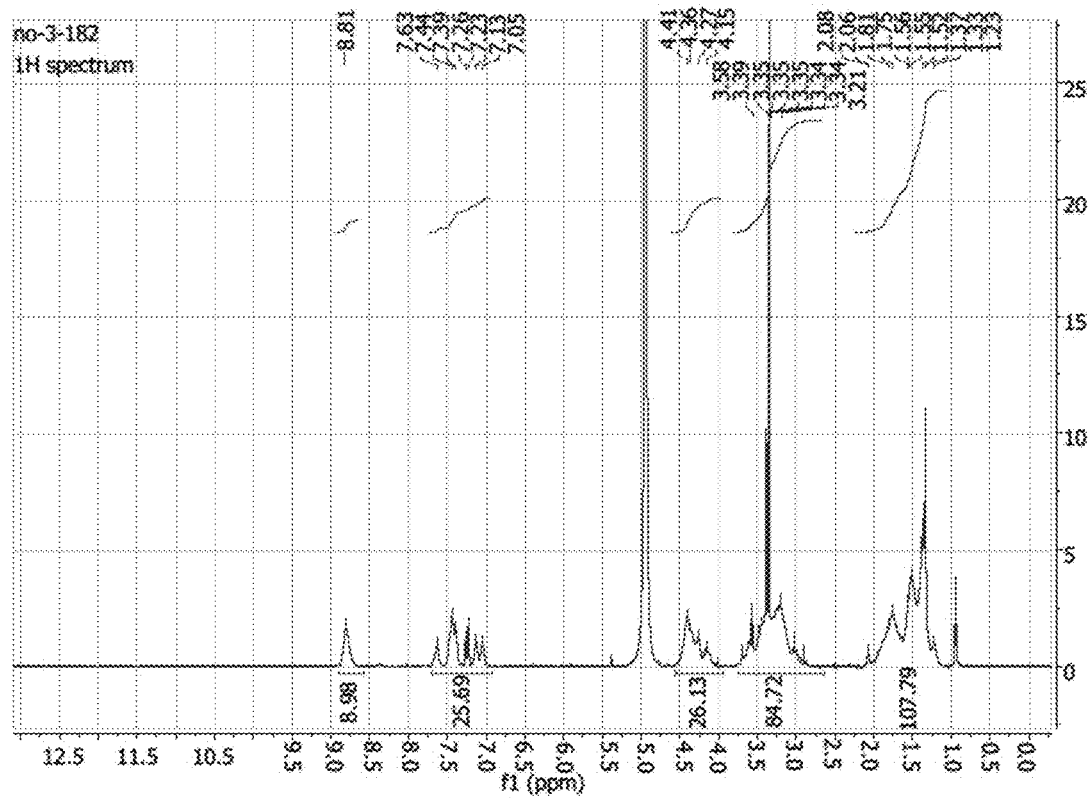

FIG. 29 provides a $^1$HNMR spectra of a denpol comprising a G3 25 TEG 3:1 (73 H 27 W). $^1$H NMR (600 MHz, CD$_3$OD) δ 8.90-8.65 (m, 7H), 7.66-7.51 (m, 3H), 7.51-7.29 (m, 9H), 7.29-7.16 (m, 3H), 7.16-6.95 (m, 4H), 4.66-4.55 (m, 1H), 4.52-3.96 (m, 24H), 3.75-2.80 (m, 81H), 1.94-1.07 (m, 88H).

Figure 30:
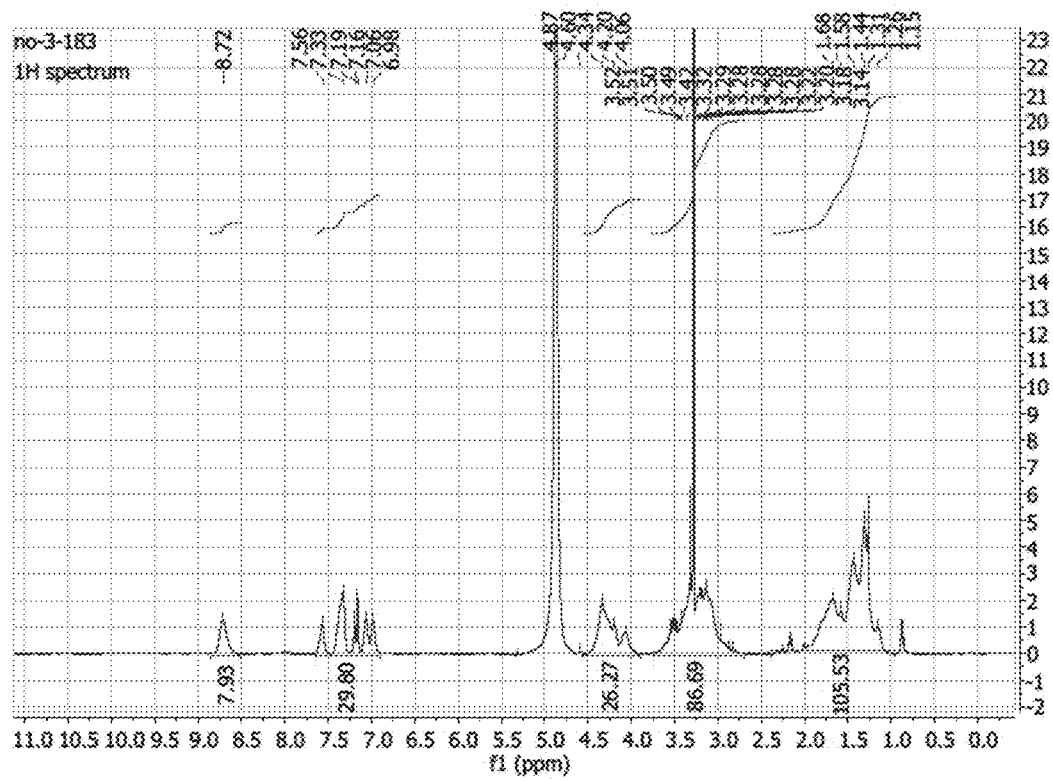

FIG. 30 provides a $^1$HNMR spectra of a denpol comprising a G3 25 TEG 2:1 (64 H 36 W). $^1$H NMR (500 MHz, CD$_3$OD) δ 8.89-8.51 (m, 8H), 7.67-7.48 (m, 4H), 7.48-7.24 (m, 12H), 7.24-7.11 (m, 5H), 7.14-6.87 (m, 9H), 4.65-4.51 (m, 1H), 4.53-3.89 (m, 26H), 3.75-2.76 (m, 87H), 2.05-1.02 (m, 103H).

Figure 31:
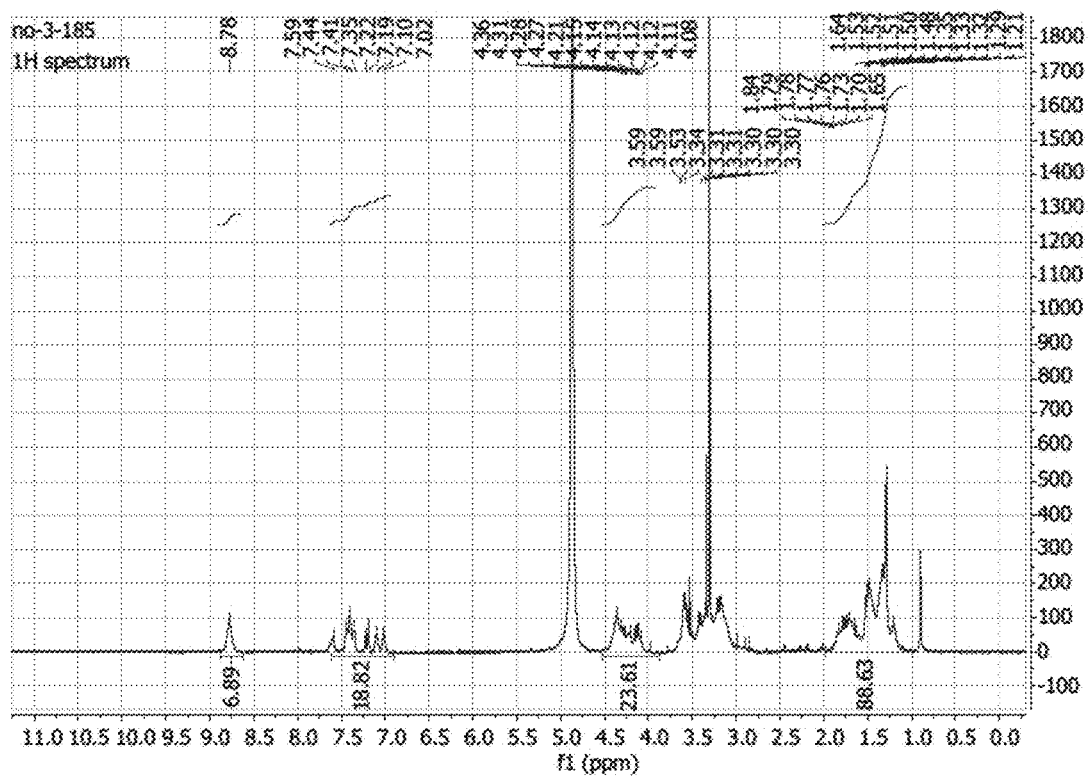

FIG. 31 provides a $^1$HNMR spectra of a denpol comprising a G3 50 TEG 3:1 (74 H 26 W). $^1$H NMR (600 MHz, CD$_3$OD) δ 8.91-8.66 (m, 4H), 7.72-7.54 (m, 2H), 7.54-7.29 (m, 6H), 7.28-7.17 (m, 2H), 7.17-6.95 (m, 3H), 4.68-4.54 (m, 1H), 4.54-3.97 (m, 22H), 3.77-2.76 (m, 76H), 2.01-1.00 (m, 63H).

Figure 32:
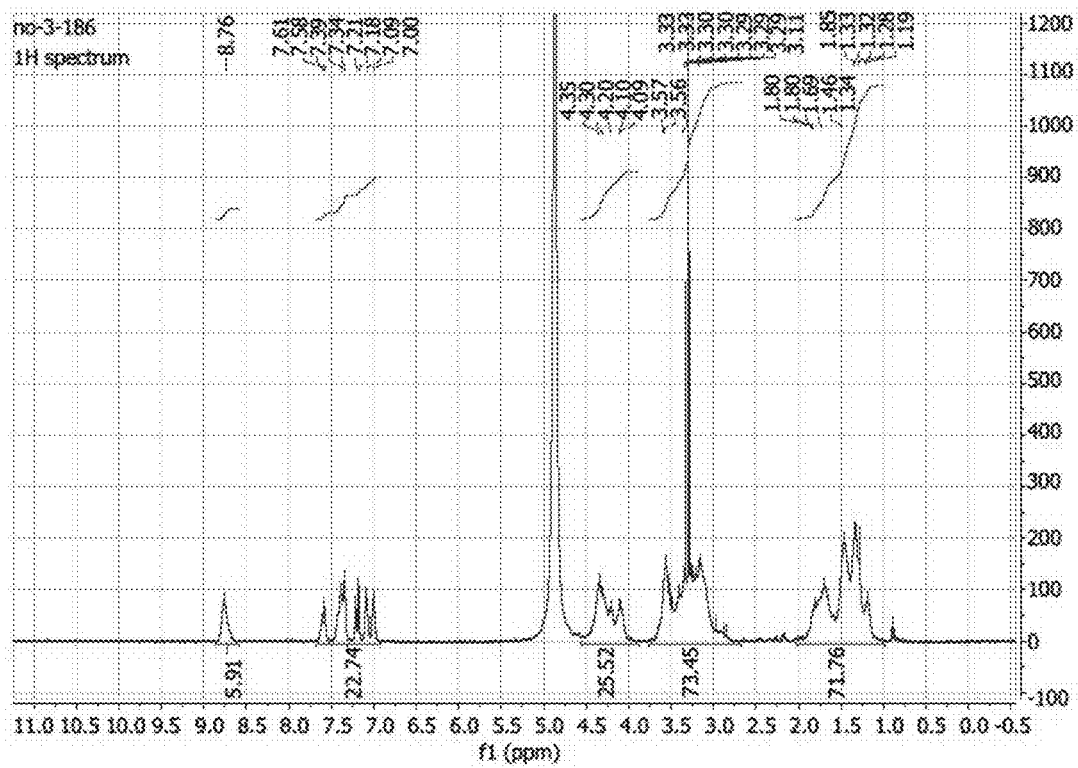

FIG. 32 provides a $^1$HNMR spectra of a denpol comprising a G3 50 TEG 2:1 (64 H 36 W). $^1$H NMR (600 MHz, CD$_3$OD) δ 8.91-8.57 (m, 6H), 7.67-7.51 (m, 3H), 7.50-7.26 (m, 9H), 7.26-7.14 (m, 3H), 7.14-6.93 (m, 7H), 4.50-3.93 (m, 25H), 3.74-2.77 (m, 74H), 2.00-1.00 (m, 72H).

Figure 33:
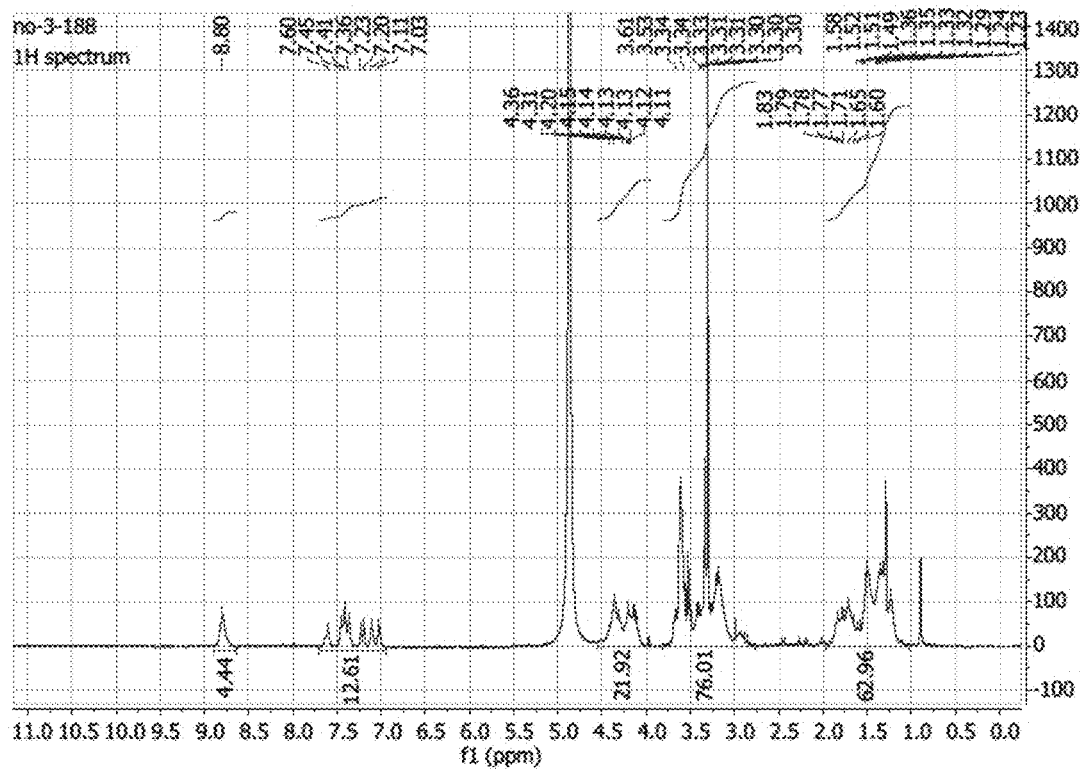

FIG. 33 provides a $^1$HNMR spectra of a denpol comprising a G3 75 TEG 3:1 (73 H 27 W). $^1$H NMR (500 MHz, CD$_3$OD) δ 8.93-8.63 (m, 9H), 7.72-7.53 (m, 3H), 7.56-7.31 (m, 12H), 7.31-7.18 (m, 4H), 7.18-6.95 (m, 6H), 4.82-4.61 (m, 1H), 4.61-3.99 (m, 26H), 3.82-2.69 (m, 85H), 2.18-1.09 (m, 108H).

Figure 34:
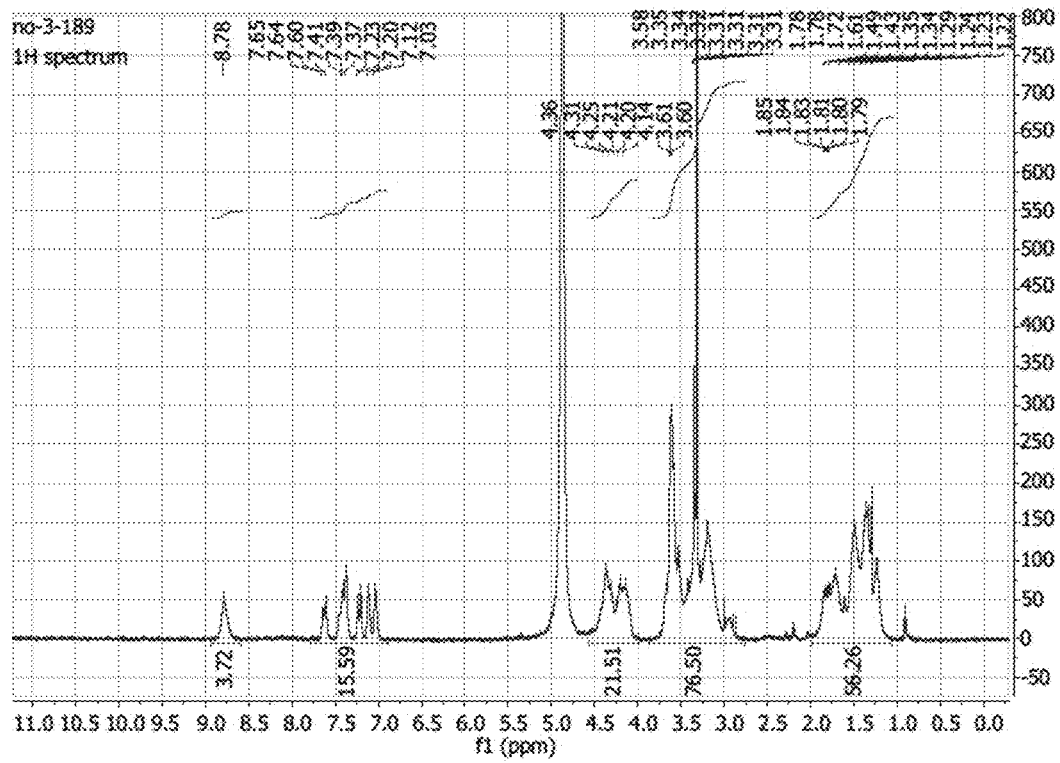

FIG. 34 provides a $^1$HNMR spectra of a denpol comprising a G3 75 TEG 2:1 (62 H 38 W). $^1$H NMR (600 MHz, CD$_3$OD) δ 8.90-8.63 (m, 4H), 7.71-7.52 (m, 2H), 7.54-7.29 (m, 6H), 7.28-7.17 (m, 2H), 7.17-6.95 (m, 5H), 4.66-4.52 (m, 1H), 4.50-3.97 (m, 21H), 3.81-2.81 (m, 76H), 2.01-1.04 (m, 56H).

Figure 35:
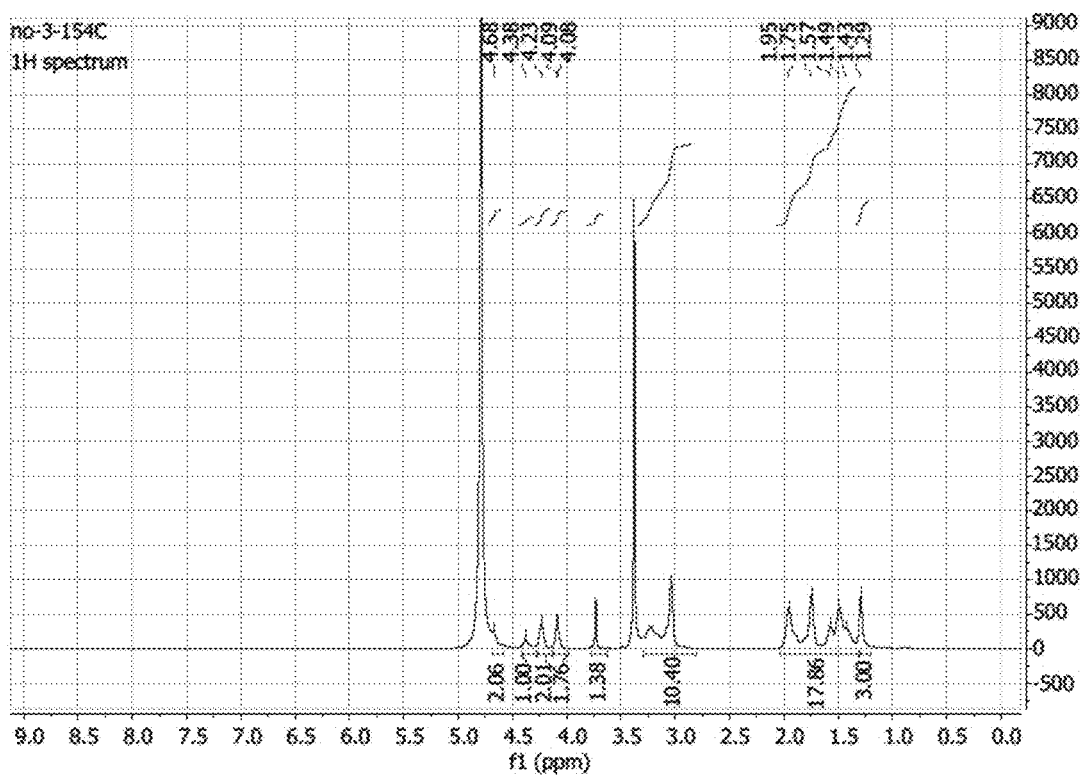

FIG. 35 provides a $^1$HNMR spectra of a denpol comprising a G1 1.0 PEG2k Backbone. $^1$H NMR (600 MHz, D$_2$O) δ 4.72-4.62 (m, 2H), 4.43-4.31 (m, 1H), 4.30-4.16 (m, 2H), 4.16-4.01 (m, 2H), 3.80-3.68 (m, 1H), 3.49-2.91 (m, 19H), 2.05-1.85 (m, 4H), 1.85-1.66 (m, 4H), 1.67-1.34 (m, 7H), 1.34-1.17 (m, 3H).

Figure 36:
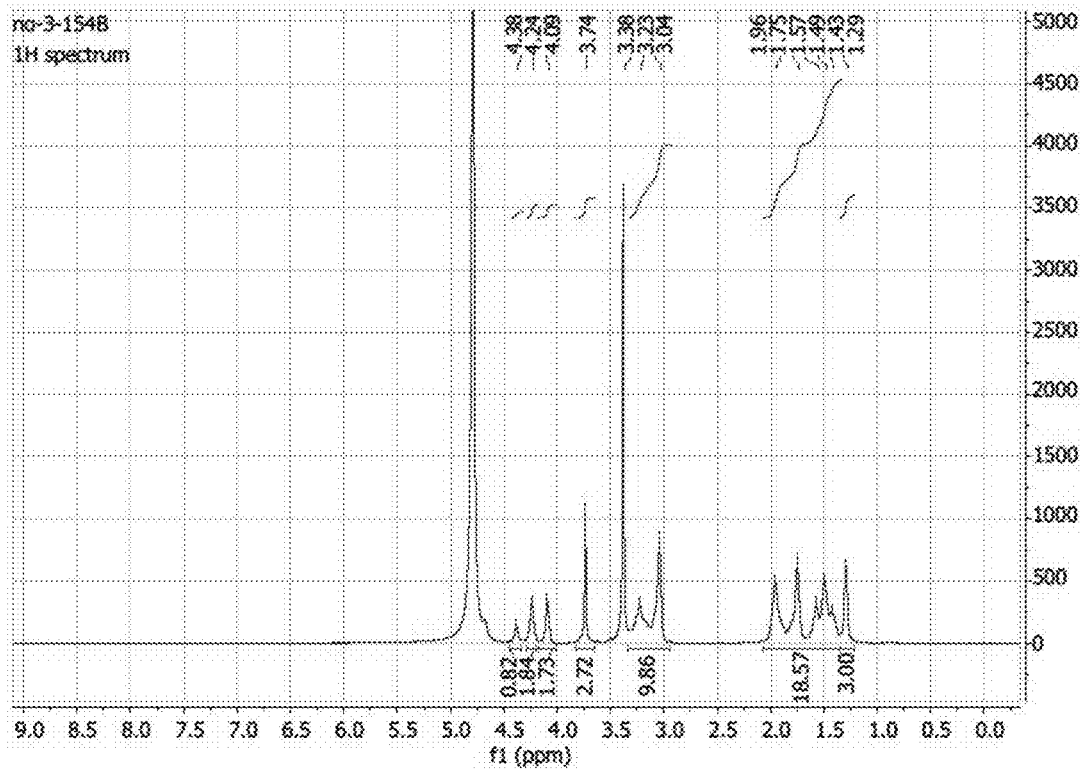

FIG. 36 provides a $^1$HNMR spectra of a denpol comprising a G1 1.5 PEG2k Backbone. $^1$H NMR (600 MHz, D$_2$O) δ 4.71-4.58 (m, 1H), 4.44-4.32 (m, 1H), 4.30-4.16 (m, 1H), 4.15-4.01 (m, 1H), 3.81-3.66 (m, 1H), 3.47-2.93 (m, 9H), 2.08-1.67 (m, 5H), 1.67-1.35 (m, 4H), 1.35-1.21 (m, 1H).

Figure 37:
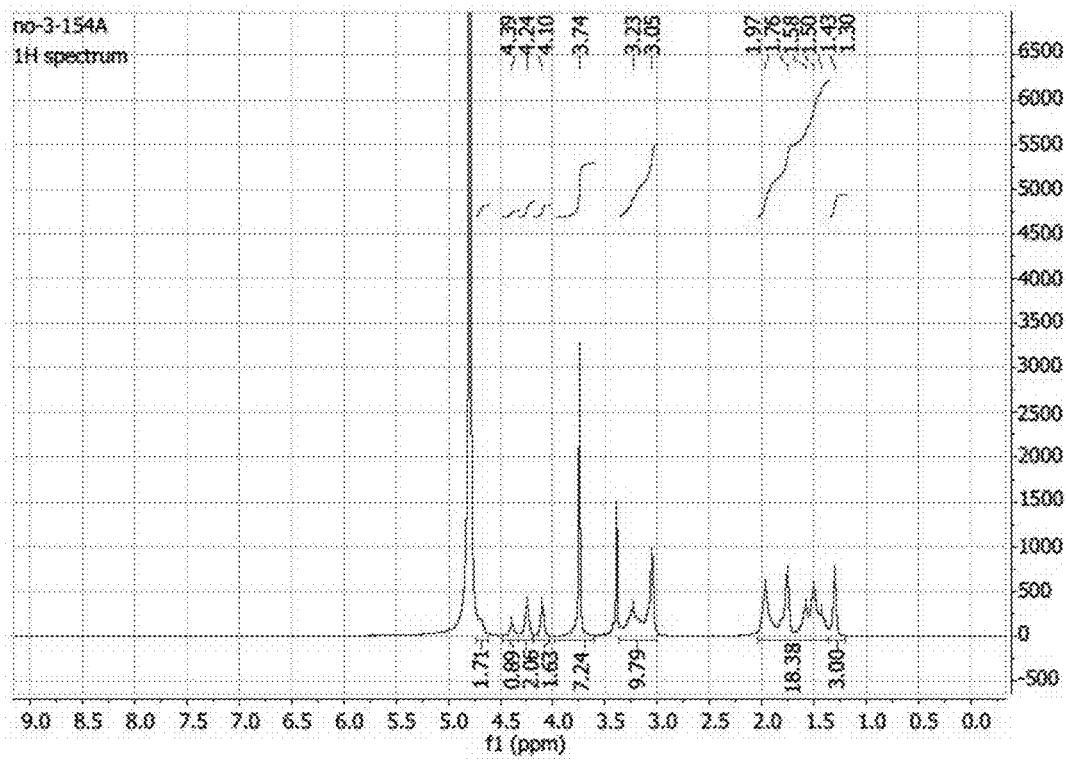

FIG. 37 provides a $^1$HNMR spectra of a denpol comprising a G1 3.0 PEG2k Backbone. $^1$H NMR (600 MHz, D$_2$O) δ 4.71-4.61 (m, 2H), 4.45-4.32 (m, 1H), 4.32-4.18 (m, 2H), 4.18-4.00 (m, 1H), 3.83-3.65 (m, 6H), 3.34-2.93 (m, 9H), 2.05-1.85 (m, 4H), 1.85-1.67 (m, 4H), 1.66-1.35 (m, 7H), 1.35-1.20 (m, 3H).

Figure 38:
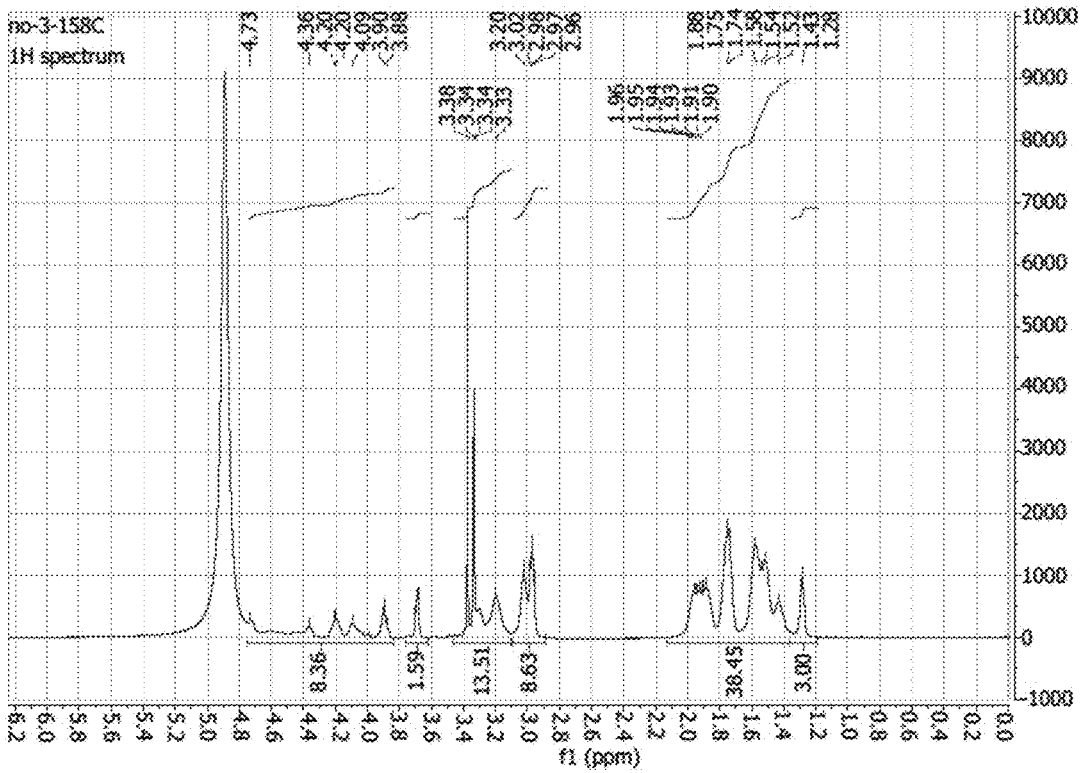

FIG. 38 provides a $^1$HNMR spectra of a denpol comprising a G2 1.0 PEG2k Backbone. $^1$H NMR (600 MHz, CD$_3$OD) δ 4.77-3.95 (m, 8H), 3.97-3.83 (m, 2H), 3.76-3.62 (m, 2H), 3.44-3.10 (m, 14H), 3.10-2.85 (m, 9H), 2.12-1.82 (m, 11H), 1.81-1.67 (m, 10H), 1.67-1.33 (m, 20H), 1.33-1.19 (m, 3H).

Figure 39:
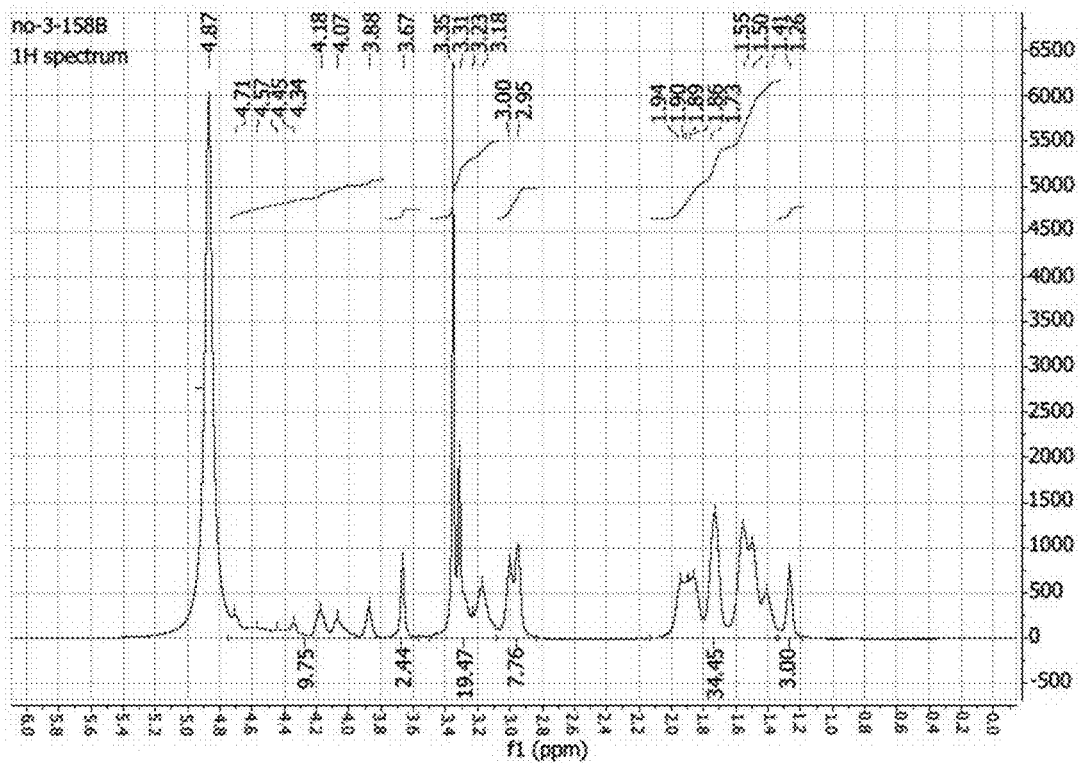

FIG. 39 provides a $^1$HNMR spectra of a denpol comprising a G2 1.5 PEG2k Backbone. $^1$H NMR (600 MHz, CD$_3$OD) δ 4.75-4.26 (m, 5H), 4.26-3.96 (m, 3H), 3.96-3.79 (m, 1H), 3.76-3.59 (m, 2H), 3.47-3.08 (m, 20H), 3.08-2.86 (m, 8H), 2.13-1.81 (m, 9H), 1.81-1.66 (m, 9H), 1.66-1.33 (m, 17H), 1.33-1.16 (m, 3H).

Figure 40:
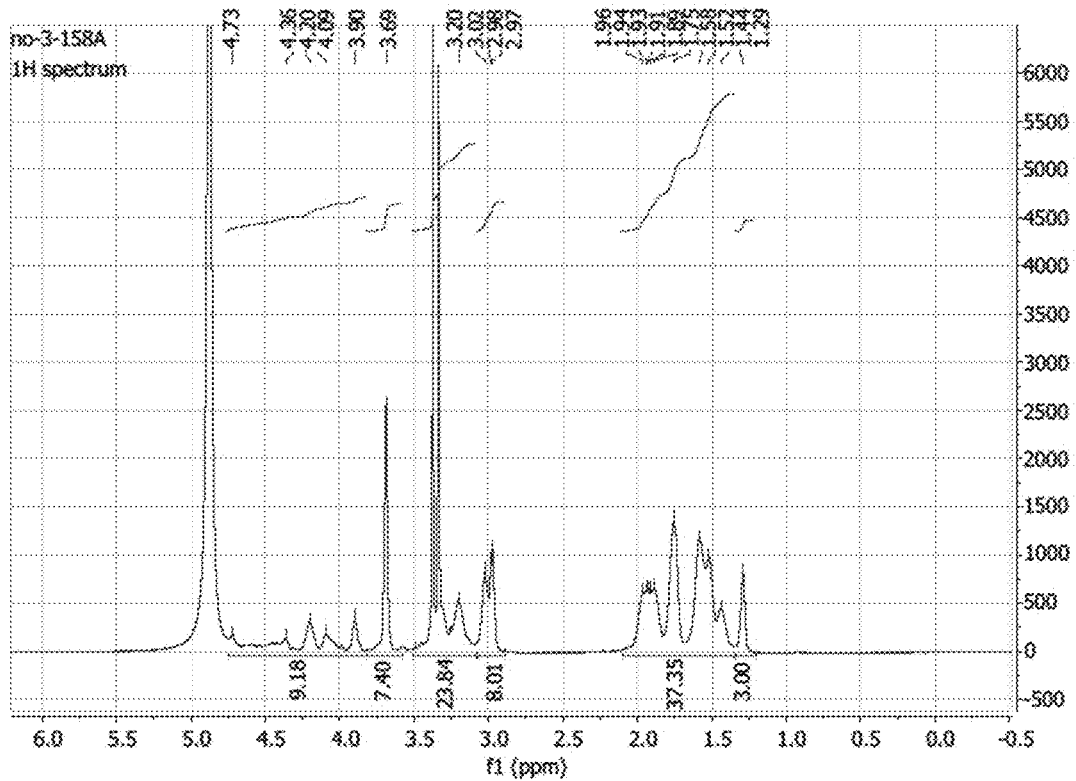

FIG. 40 provides a ¹HNMR spectra of a denpol comprising a G2 3.0 PEG2k Backbone. ¹H NMR (600 MHz, CD₃OD) δ 4.76-4.29 (m, 4H), 4.27-4.13 (m, 2H), 4.15-3.95 (m, 2H), 3.95-3.83 (m, 2H), 3.78-3.61 (m, 7H), 3.50-3.09 (m, 24H), 3.09-2.89 (m, 8H), 2.14-1.82 (m, 10H), 1.82-1.67 (m, 10H), 1.67-1.34 (m, 18H), 1.34-1.21 (m, 3H).

Figure 41:
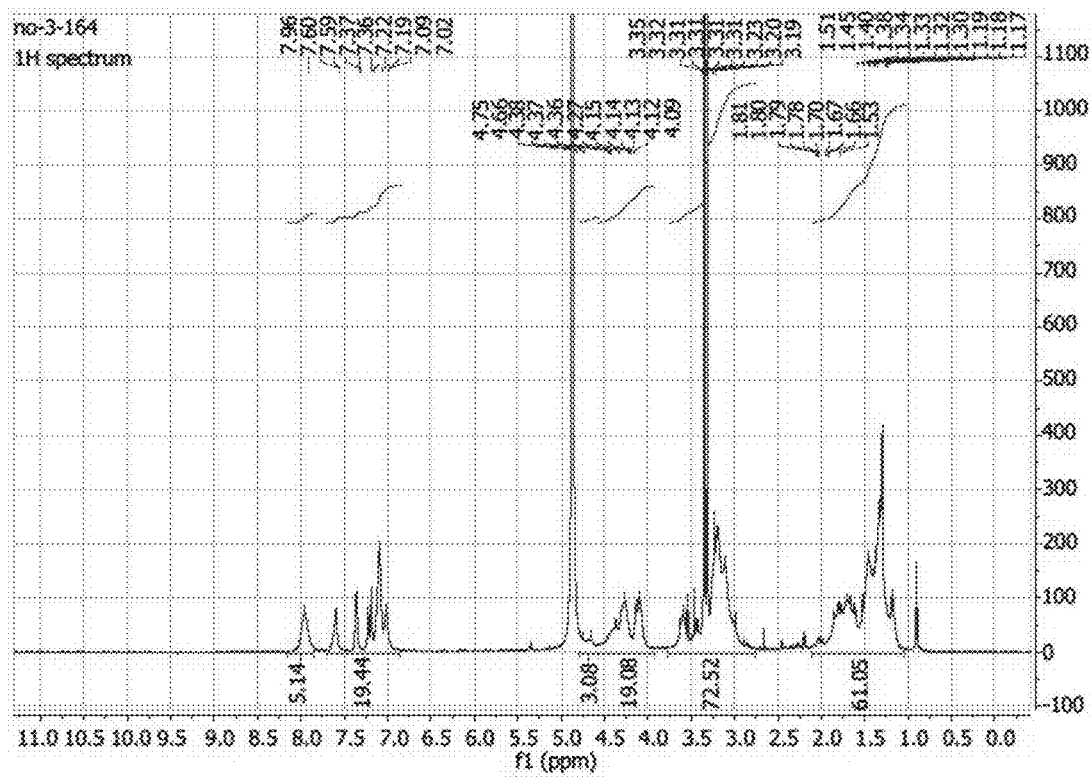

FIG. 41 provides a ¹HNMR spectra of a denpol comprising a G1 1.0 PEG2k 2:1 (64 H 36 W). ¹H NMR (600 MHz, CD₃OD) δ 8.14-7.81 (m, 5H), 7.68-7.50 (m, 3H), 7.43-7.29 (m, J=6.4 Hz, 3H), 7.29-6.82 (m, 14H), 4.76-4.61 (m, 2H), 4.58-3.94 (m, 19H), 3.71-2.77 (m, 71H), 2.05-1.05 (m, 60H).

Figure 42:
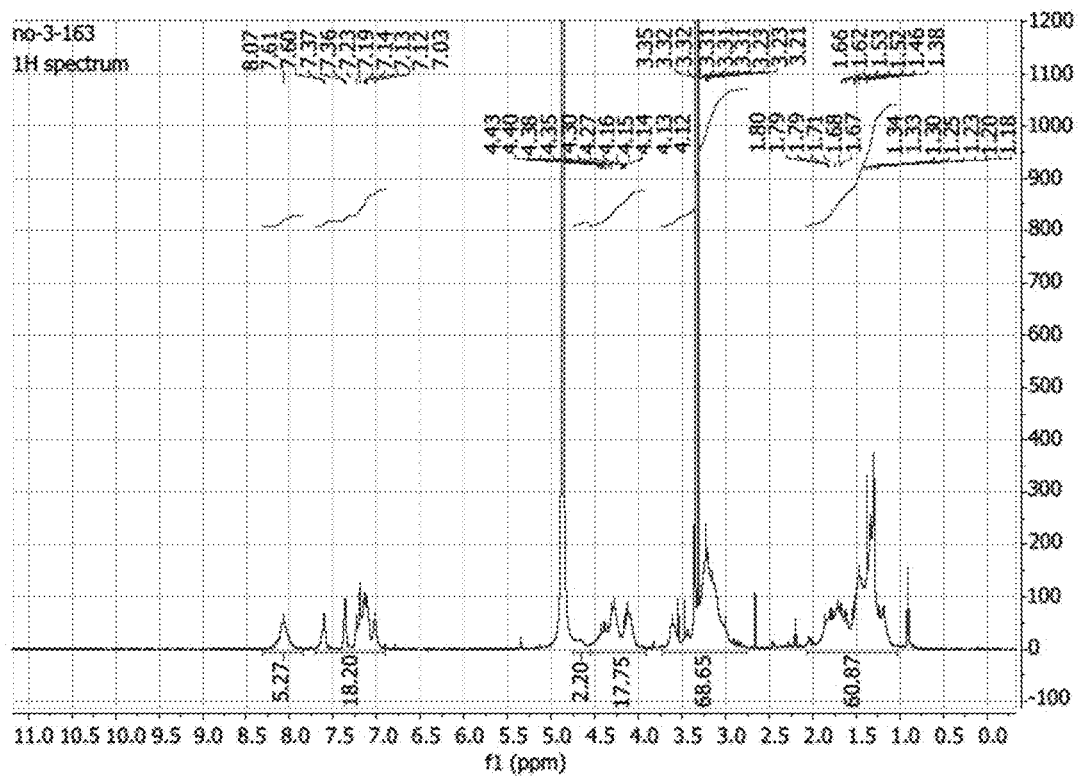

FIG. 42 provides a ¹HNMR spectra of a denpol comprising a G1 1.5 PEG2k 2:1 (67 H 33 W). ¹H NMR (600 MHz, CD₃OD) δ 8.28-7.87 (m, 5H), 7.71-7.52 (m, 2H), 7.44-7.29 (m, 3H), 7.29-6.89 (m, 13H), 4.72-4.59 (m, 2H), 4.57-3.95 (m, 18H), 3.75-2.78 (m, 69H), 2.01-1.03 (m, 61H).

Figure 43:
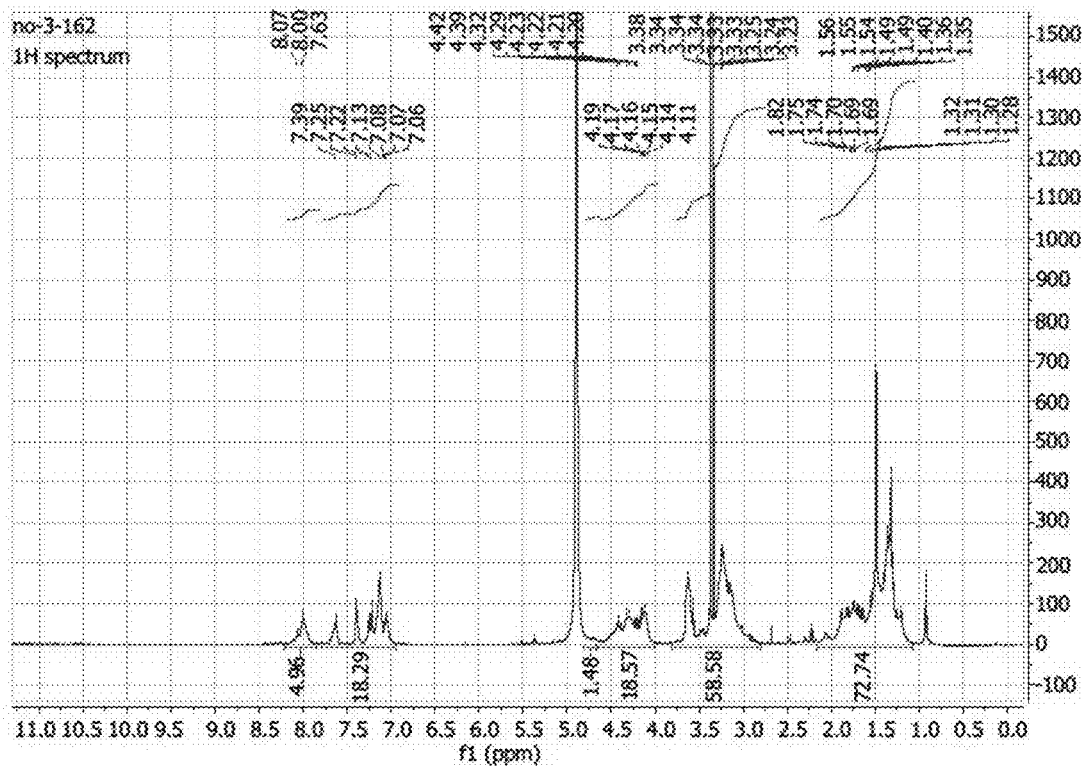

FIG. 43 provides a ¹HNMR spectra of a denpol comprising a G1 3.0 PEG2k 2:1 (65 H 35 W). ¹H NMR (600 MHz, CD₃OD) δ 8.19-7.82 (m, 5H), 7.75-7.55 (m, 3H), 7.44-7.31 (m, 3H), 7.32-6.93 (m, 13H), 4.77-4.63 (m, 1H), 4.57-4.00 (m, 18H), 3.75-2.83 (m, 58H), 2.13-1.05 (m, 73H).

Figure 44:
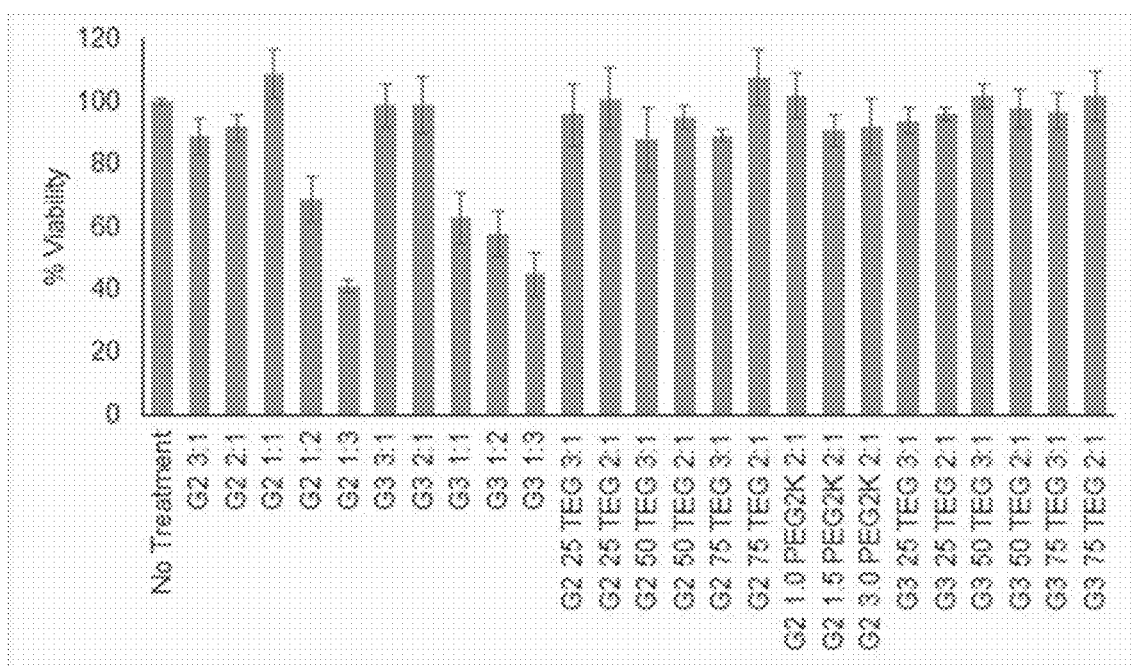

FIG. 44 demonstrates the cytotoxicity of the denpol vectors against 3T3 cells assayed using a LDH assay.

Figure 45A:
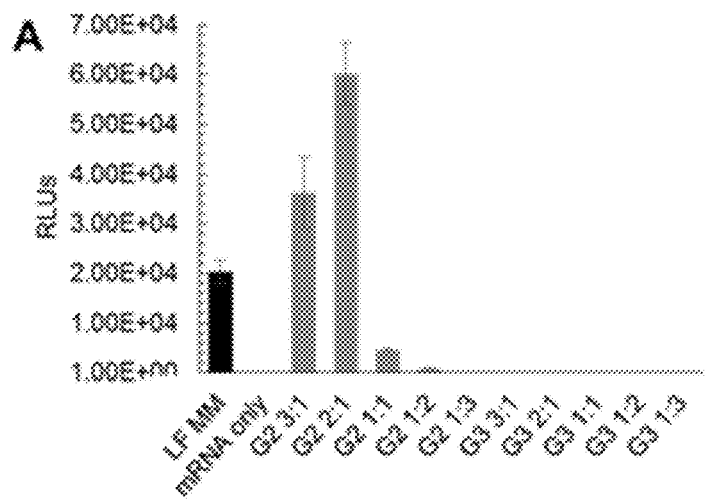
Figure 45B:
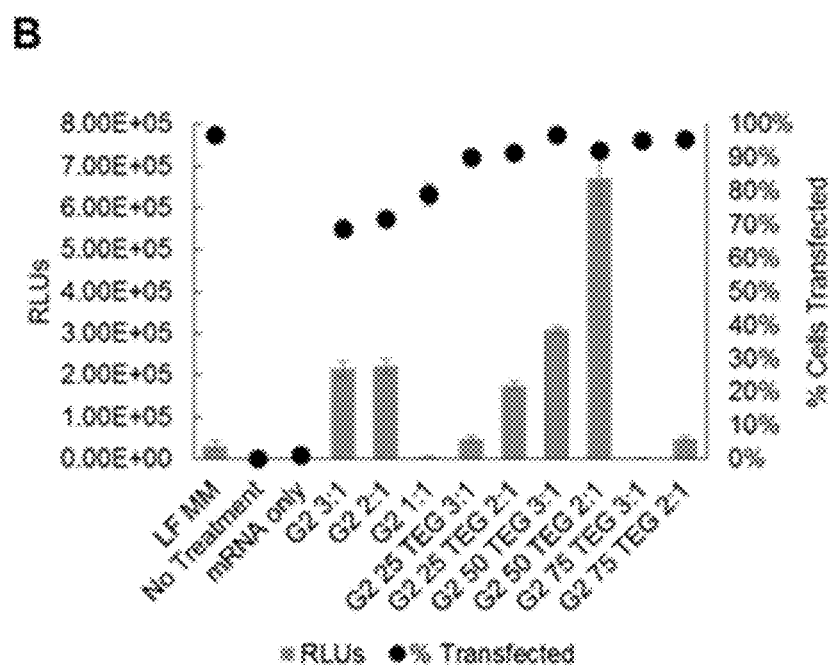

FIG. 45A-B displays the results of transfecting 3t3 cells with denpols. 70% confluence. 24 h exposure to transfection media. 200 ng Fluc mRNA per well, (A) Screen of His:Trp ratio. N:P=45; (B) Screen of the denpol library created for study, N:P=10.

Figure 46:
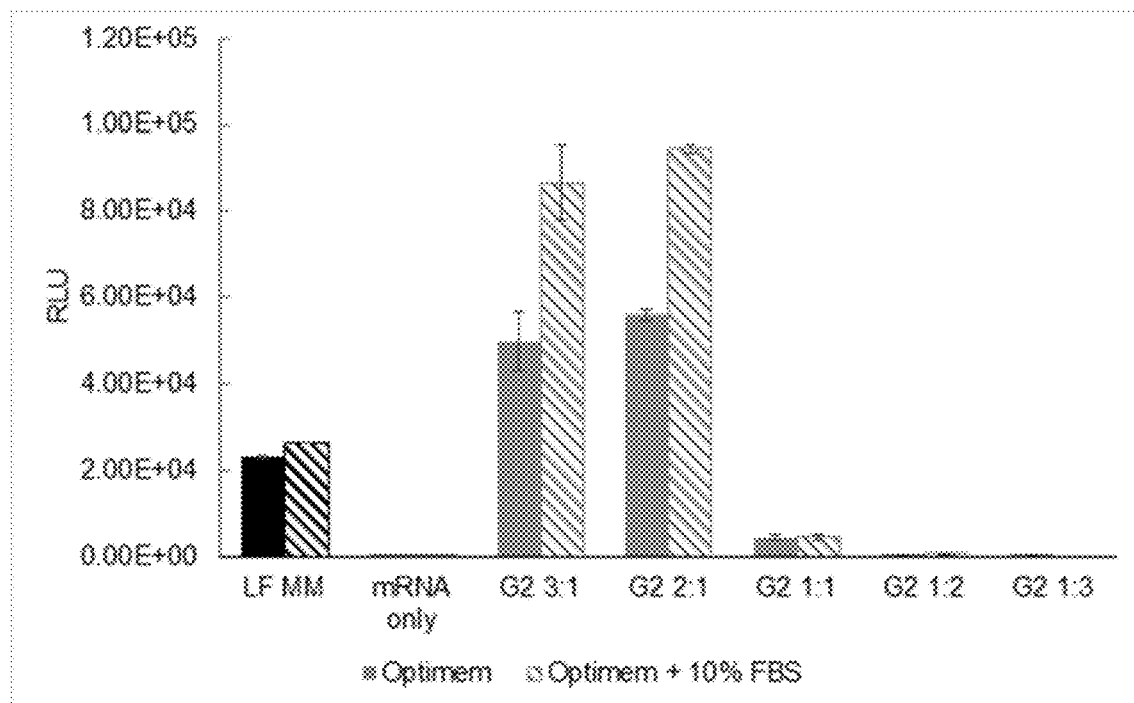

FIG. 46 shows the effect of 10% FBS on denpol transfections.

Figure 47:
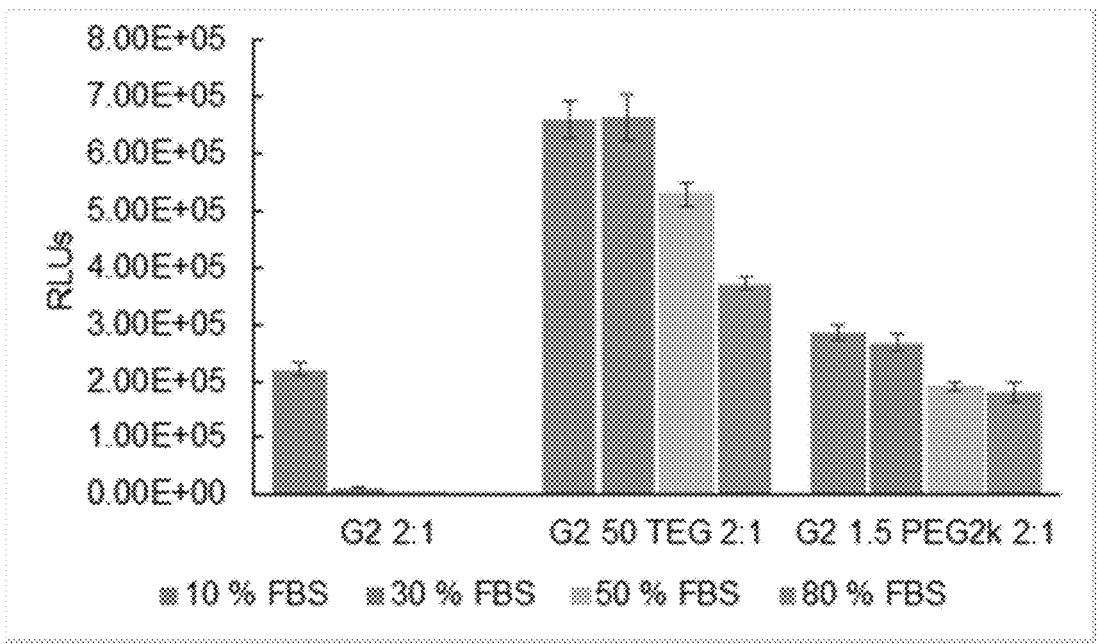

FIG. 47 shows the effects of increasing FBS concentration in transfection efficiency. N:P=10, 200 ng FLuc mRNA, 24 hours exposure to transfection media.

Figure 48:
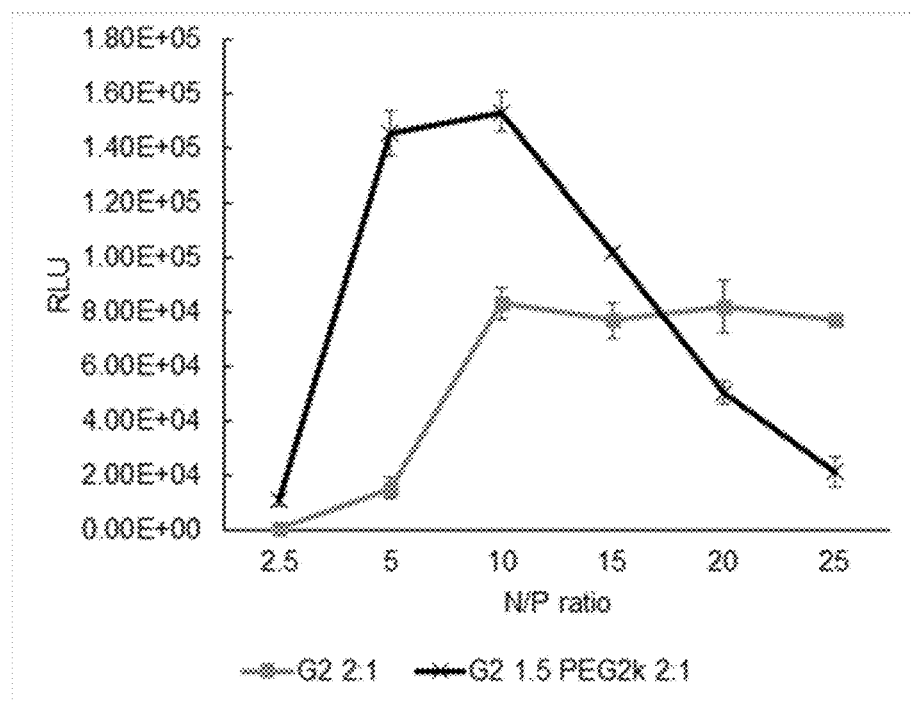

FIG. 48 displays a representative N:P screen of a non-PEGylated and PEGylated vector. Non-PEGylated vectors tended to plateau after N:P 10 and had slightly diminished luminescence after N:P 30. PEGylated vectors Peaked between N:P 5-15 and had a maximum at N:P 10.

Figure 49:
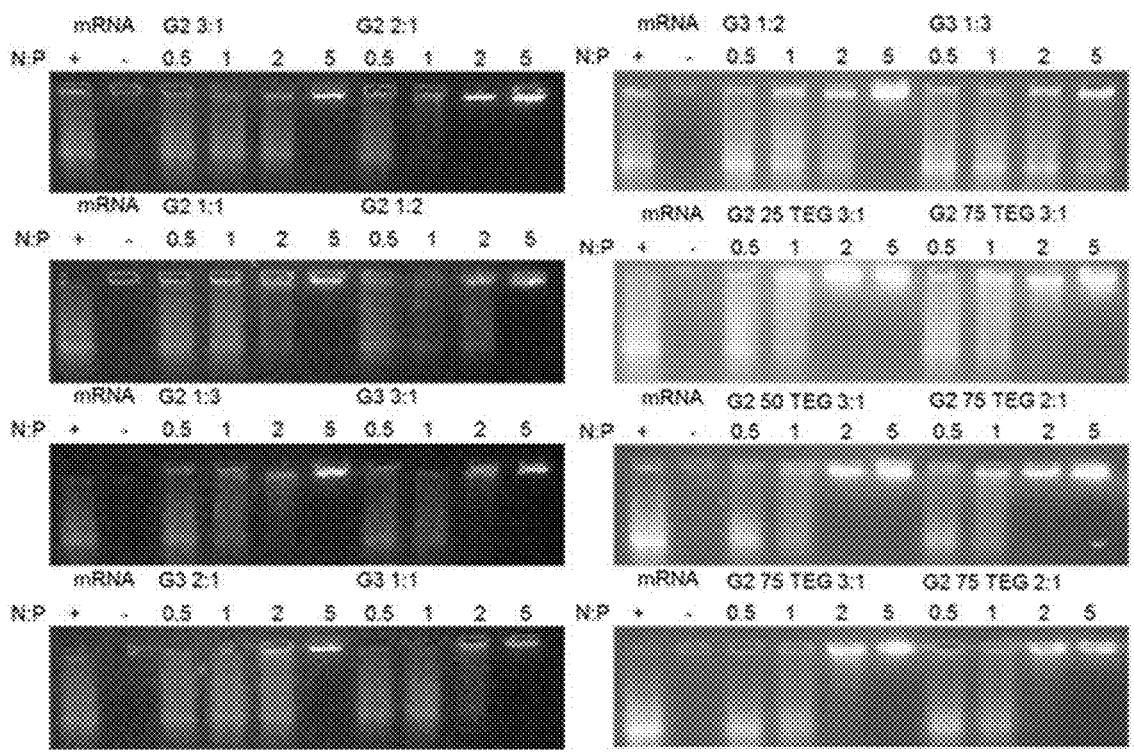

FIG. 49 provides representative gel shift binding assays in 1% agarose. All vectors surveyed bound mRNA by N:P 5.

Figures 50A, 50B:
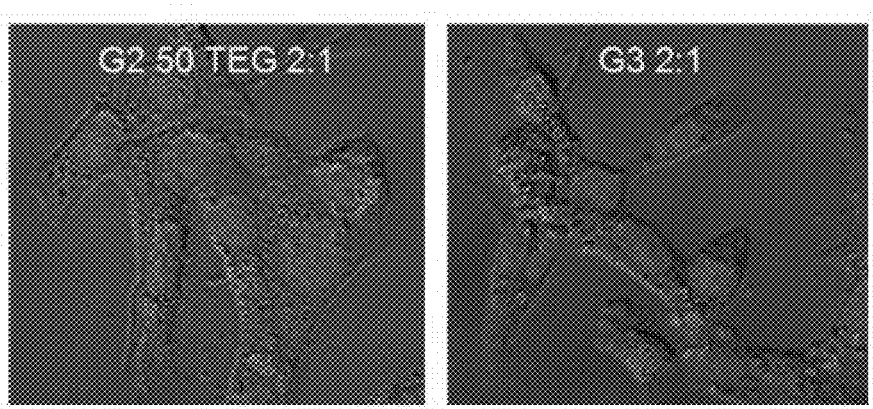

FIG. 50A-B provides for denpol nanoparticle characterization. N:P=10 (A)Diameter is based on Z-avg in transfection media (10% fbs in optimem). Zeta potential measurements are made in optimem alone; (B) Confocal microscopy image highlighting a colloidally stable (G2 50 TEG 2:1) denpol versus a denpol that aggregates (G3 3:1)

Figure 51:
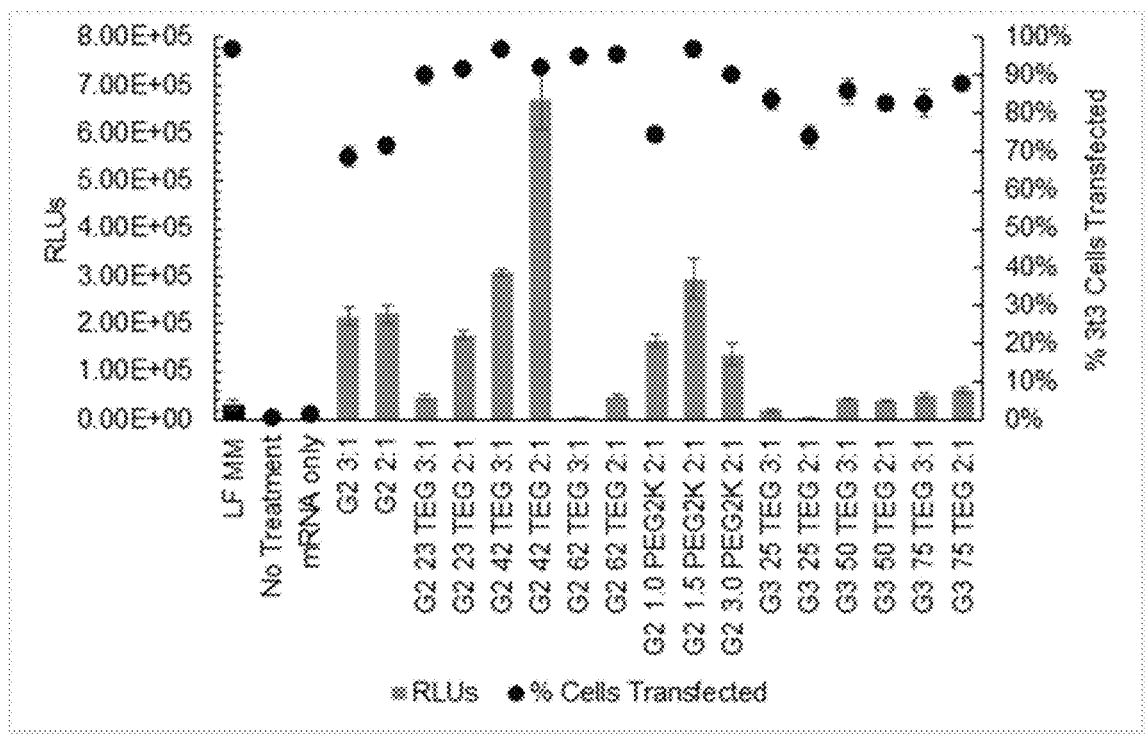

FIG. 51 provides for a screen of the synthesized denpols.

Figure 52:
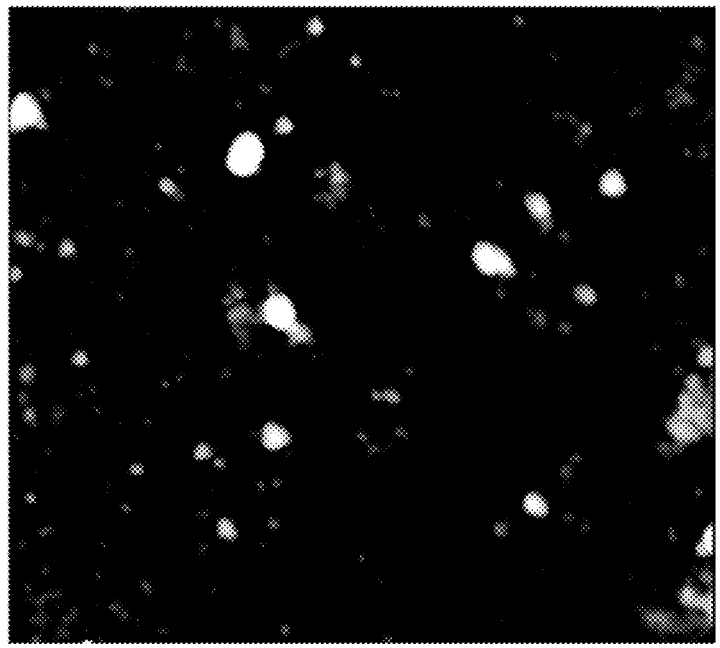

FIG. 52 shows dry AFM of mRNA denpol nanoparticles on mica. Each side represents 5 µm.

Figure 53A:
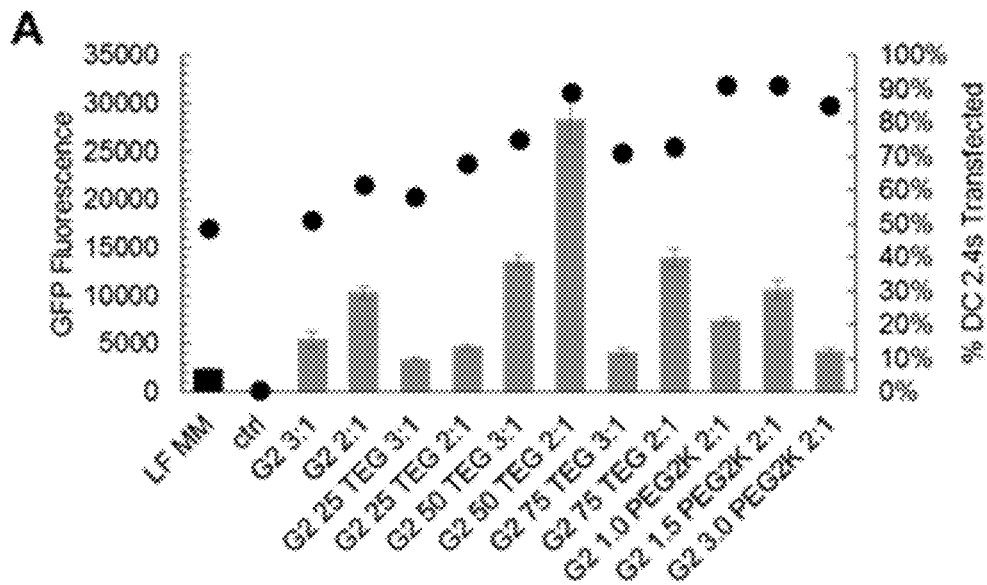
Figure 53B:
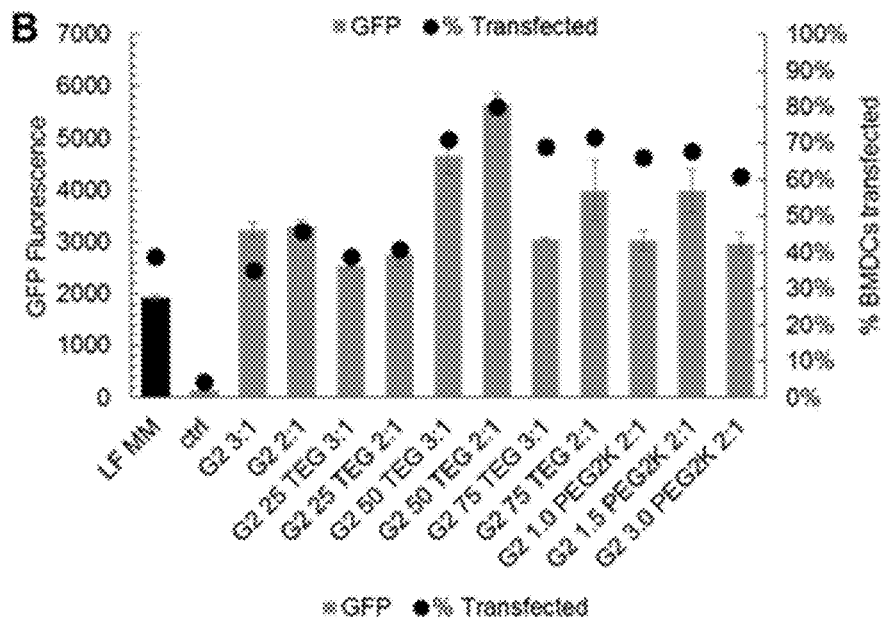

FIG. 53A-B presents the results of transfections with dendritic cells. N:P=15, 200 ng Cy-5 labeled eGFP mRNA per well. (A) DC 2.4 cells, 70% confluent, 24 h exposure; and (B) primary BMDCs, 60 k per well, 12 h exposure.

FIG. 54A-B demonstrates cas9 mediated knockout of eGFP in DB-7 cells. (A) Flow cytometry data showing knockout over 8 days. (B) DB-7 cells, 70% confluent, 48-hour exposure.

DETAILED DESCRIPTION

As used herein and in the appended claims, the singular forms "a," "an," and "the" include plural referents unless the context clearly dictates otherwise. Thus, for example, reference to "a vector" includes a plurality of such vectors and reference to "the amino acid" includes reference to one or more amino acids and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

The term "alkenyl", refers to an organic group that is comprised of carbon and hydrogen atoms that contains at least one double covalent bond between two carbons. Typically, an "alkenyl" as used in this disclosure, refers to organic group that contains 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. While a $C_2$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 2 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkyl", refers to an organic group that is comprised of carbon and hydrogen atoms that contains single covalent bonds between carbons. Typically, an "alkyl" as used in this disclosure, refers to an organic group that contains 1, 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. While a $C_2$-alkynyl can form a triple bond to a carbon of a parent chain, an alkynyl group of three or more carbons can contain more than one triple bond. Where if there is more than 3 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "aryl", as used in this disclosure, refers to a conjugated planar ring system with delocalized pi electron clouds that contain only carbon as ring atoms. An "aryl" for the purposes of this disclosure encompass from 1 to 4 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term generally represented by the notation "$C_x$-$C_y$" (where x and y are whole integers and y>x) prior to a functional group, e.g., "$C_1$-$C_{12}$ alkyl" refers to a number range of carbon atoms. For the purposes of this disclosure any range specified by "$C_x$-$C_y$" (where x and y are whole integers and y>x) is not exclusive to the expressed range, but is inclusive of all possible ranges that include and fall within the range specified by "$C_x$-$C_y$" (where x and y are whole integers and y>x). For example, the term "$C_1$-$C_4$" provides express support for a range of 1 to 4 carbon atoms, but further provides implicit support for ranges encompassed by 1 to 4 carbon atoms, such as 1 to 2 carbon atoms, 1 to 3 carbon atoms, 2 to 3 carbon atoms, 2 to 4 carbon atoms, and 3 to 4 carbon atoms.

The term "cylcloalkenyl", as used in this disclosure, refers to an alkene that contains at least 4 carbon atoms but no more than 12 carbon atoms connected so that it forms a ring. A "cycloalkenyl" for the purposes of this disclosure encompasses from 1 to 4 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "cylcloalkyl", as used in this disclosure, refers to an alkyl that contains at least 3 carbon atoms but no more than 12 carbon atoms connected so that it forms a ring. A "cycloalkyl" for the purposes of this disclosure encompasses from 1 to 4 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O. In a particular embodiment, a "hetero"-hydrocarbon (e.g., alkyl, alkenyl, alkynyl) refers to a hydrocarbon that has from 1 to 3 C, N and/or S atoms as part of the parent chain.

The term "disorder" as used herein is intended to be generally synonymous, and is used interchangeably with, the terms "disease," "syndrome," and "condition" (as in medical condition), in that all reflect an abnormal condition of the human or animal body or of one of its parts that impairs normal functioning, is typically manifested by distinguishing signs and symptoms.

The term "heterocycle," as used herein, refers to ring structures that contain at least 1 noncarbon ring atom. A "heterocycle" for the purposes of this disclosure encompass from 1 to 4 heterocycle rings, wherein when the heterocycle is greater than 1 ring the heterocycle rings are joined so that they are linked, fused, or a combination thereof. A heterocycle may be aromatic or nonaromatic, or in the case of more than one heterocycle ring, one or more rings may be nonaromatic, one or more rings may be aromatic, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In the case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

The term "mRNA", as used herein, includes modifications of the mRNA termini, including tagging the ends of mRNA with moieties such as cholesterol, folate, various peptides, and aptamers; fluorescent molecules; and 3'-biotin. Moreover, "mRNA", as used herein refers to a strand of ribobonucleotides that can be of any length disclosed herein, and can further comprise modified riboribonucleotides in addition to the naturally occurring riboribonucleotides. Specific examples of modified riboribonucleotides include riboribonucleotides which comprise pseudouridine, 5-methyluridine, 2-thiouridine, 5-mnethylcytidine (m5C), and N6-methyladenosine bases.

The term "non-release controlling excipient" as used herein, refers to an excipient whose primary function do not include modifying the duration or place of release of the active substance from a dosage form as compared with a conventional immediate release dosage form.

The term "optionally substituted" refers to a functional group, typically a hydrocarbon or heterocycle, where one or more hydrogen atoms may be replaced with a substituent. Accordingly, "optionally substituted" refers to a functional group that is substituted, in that one or more hydrogen atoms are replaced with a substituent, or unsubstituted, in that the hydrogen atoms are not replaced with a substituent. For example, an optionally substituted hydrocarbon group refers to an unsubstituted hydrocarbon group or a substituted hydrocarbon group.

The term "pharmaceutically acceptable carrier," "pharmaceutically acceptable excipient," "physiologically acceptable carrier," or "physiologically acceptable excipient" as used herein, refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. Examples of "pharmaceutically acceptable carriers" and "pharmaceutically acceptable excipients" can be found in the following, Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, Fla., 2004.

The term "release controlling excipient" as used herein, refers to an excipient whose primary function is to modify the duration or place of release of the active substance from a dosage form as compared with a conventional immediate release dosage form.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenicity, are commensurate with a reasonable benefit/risk ratio, and are effective for their intended use.

The terms "treat", "treating" and "treatment", as used herein, refers to ameliorating symptoms associated with a disease or disorder (e.g., multiple sclerosis), including preventing or delaying the onset of the disease or disorder symptoms, and/or lessening the severity or frequency of symptoms of the disease or disorder.

The term "ssRNA", as used herein, refers to a single strand of ribonucleotides that can be of any length disclosed herein, and can further comprise modified ribonucleotides in addition to the naturally occurring ribonucleotides. Specific examples of modified ribonucleotides include ribonucleotides which comprise pseudouridine, 5-methyluridine, 2-thiouridine, 5-methylcytidine (m5C), and N6-methyladenosine bases. The ends of the ssRNA may also be modified, including tagging the ends of the ssRNA with moieties such as cholesterol, folate, various peptides, and aptamers; fluorescent molecules; and 3'-biotin. For purposes of this disclosure, "ssRNA" includes single guide RNA (sgRNA), sgRNA, crRNA, and tracrRNA.

The term "subject" as used herein, refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein. For example, a mammalian subject can refer to a human patient.

The term "substituent" refers to an atom or group of atoms substituted in place of a hydrogen atom. For purposes of this invention, a substituent would include deuterium atoms.

The term "substituted" with respect to hydrocarbons, heterocycles, and the like, refers to structures wherein the parent chain contains one or more substituents.

The term "unsubstituted" with respect to hydrocarbons, heterocycles, and the like, refers to structures wherein the parent chain contains no substituents.

Originally thought to be too instable and immunogenic for the treatment of diseases, messenger RNA (mRNA) has reemerged as a promising therapeutic. There are several conceptual advantages of mRNA-based therapy compared to other nucleic acid-based approaches. Unlike DNA-based therapy, mRNA does not have the risk of integration into the chromosomes, which can lead to insertional mutagenesis with potentially disastrous results. mRNA delivered therapeutically only results in transient translation that can be controlled by both changes in the UTRs or coding sequence and is completely degraded through physiologic pathways. This is considered both an advantage and a disadvantage depending on therapeutic needs. In principle, mRNA-based therapies appear to be much safer than DNA or viral and are applicable to a broad spectrum of disorders both acute and chronic.

The use of mRNA in the field of cancer vaccination has experienced the greatest amount of preclinical investigation and has achieved multiple stages of clinical testing. With the advent of new discoveries that have both increased the amount of protein produced per delivered mRNA, through improvements in mRNA structure and delivery, and the reduction of intrinsic immunogenicity of mRNA, new approaches to replace proteins in cardiology, oncology, endocrinology and the treatment of genetic disorders, such as cystic fibrosis or hemophilia are being studied.

As a notable application, mRNA based prophylactic and therapeutic antitumor immunity has vitalized the field of immuno-oncology. Peptide or protein antigens isolated from tumors are coded into mRNA and delivered ex vivo or in vivo to dendritic cells. Upon translation of the mRNA, major histocompatibility complexes (MHC) present the coded antigen and activate T-cells against the tumor. Liposomes and cationic polymers are currently used for this application, but inefficient delivery to immune cells is cited as hindering the clinical applications. On closer inspection, some of the synthetic mRNA delivery vectors were found to be reformulated or reconstructed siRNA or pDNA delivery vectors. While repurposing materials has been effective, there was little discussion about what specific variables or changes enabled effective mRNA delivery.

Synthetic vector systems have been developed an optimized for delivering siRNA into cells. However, siRNA is structurally different from mRNA. While siRNA, mRNA, and ssRNA all comprise ribonucleotides, siRNA is duplexed, rigid, and universally only 20-25 base pairs in length, while mRNA and ssRNA are single stranded, can vary greatly in length, and can form aggregates by forming stem loop structures or by base pairing. For example, unlike siRNA, the average size of eukaryotic mRNAs is around 1500 to 2000 ribonucleotides in length. Moreover, mRNA and ssRNA are far more susceptible to enzymatic degradation by RNAses than siRNA. Accordingly, the considerations for delivering mRNA and/or ssRNA versus siRNA would have to take into account the notable structural and chemical differences between the two types of molecules. For example, a dendronized polymer system optimized for siRNA delivery indicated that dendrons that were terminally functionalized with histidine and tryptophan in a 3:1 ratio was optimal for siRNA delivery. In direct contrast, it was found herein that vectors that have a higher percentage of tryptophan on the dendron surface was important for increasing transfection efficiency, presumably due to the increased binding to the less ordered structure of mRNA and ssRNA. Moreover, it was further found herein that the inclusion of a glycol (e.g., PEG or TEG) increased transfection ability, serum resistance, and colloidal stability of the vector/mRNA nanoparticles by reducing the high propensity of mRNA and ssRNA to aggregate. Finally, the vectors of the disclosure demonstrated the ability to transfect both DC2.4 and BMDCs with mRNAs, indicating great promise for the use of the vectors with mRNA as vaccines. Accordingly, the disclosure provides for vectors that are superior to other similar vectors known in the art for delivering mRNA and/or ssRNA into cells.

The vectors of the disclosure comprise a highly branched and flexible architecture that is fully composed of natural amino acids so as to ensure biodegradability and low toxicity (i.e., biocompatible) that is further capable of forming stable colloidal non-aggregating polyplexes with mRNA and/or ssRNA, and which can effectively release the mRNA and/or ssRNA within a cell. The vectors disclosed herein are not limited to the exemplified structures presented herein, but include any structure characterized by the following structural and functional characteristics, including a non-toxic and non-immunogenic polymer that (1) has a highly branched architecture; (2) has chain flexibility, and which is further capable of forming polyplexes with mRNA and/or ssRNA and is then able to release mRNA and/or ssRNA within a cell; (3) prevents aggregation during nanoparticle assembly with mRNA and/or ssRNA; and (4) comprise agents or moieties that can intercalate between mRNA and/or ssRNA base pairs. Accordingly, it should be understood, that the disclosure does not simply provide for dendronized polymers based only on the following presented structural Formulas, but also includes vectors that are comprised of different polymer backbones and which can contain non-peptide dendrons.

In a particular embodiment, the disclosure provides for a vector comprising the structure of Formula I:

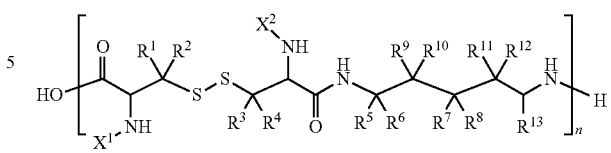

Formula I wherein, n is an integer greater than 1, 2, 3, 4, 5, 6, 7, 8, 9, 10, 15, 20, 25, 50, 100, 200, 300, 400, 500, 1000, 500, 10000, 20000, or 50000;

$R^1$-$R^{12}$ are independently selected from the group comprising H, D, optionally substituted ($C_1$-$C_{12}$)-alkyl, optionally substituted ($C_1$-$C_{12}$)-heteroalkyl, optionally substituted ($C_2$-$C_{12}$)-alkenyl, optionally substituted ($C_{2\text{-}12}$)-heteroalkenyl, optionally substituted ($C_{2\text{-}12}$)-alkynyl, optionally substituted ($C_2$-$C_{12}$)-heteroalkynyl, optionally substituted ($C_3$-$C_{12}$)-cycloalkyl, optionally substituted ($C_4$-$C_{12}$)-cycloalkenyl, halo (e.g., F, Cl, Br or I), optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), optionally substituted boron containing functional group (e.g., boronic acid, boronic ester, borinic acid, and borinic ester), optionally substituted aryl, optionally substituted heterocycle; alternatively, $R^1$-$R^{12}$ are independently selected from the group consisting of optionally substituted ($C_1$-$C_6$)-alkyl, optionally substituted ($C_1$-$C_6$)-heteroalkyl, optionally substituted ($C_2$-$C_6$)-alkenyl, optionally substituted ($C_2$-$C_6$)-heteroalkenyl, optionally substituted ($C_2$-$C_6$)-alkynyl, optionally substituted ($C_2$-$C_6$)-heteroalkynyl, optionally substituted ($C_3$-$C_{12}$)-cycloalkyl, optionally substituted ($C_4$-$C_{12}$)-cycloalkenyl, halo, hydroxyl, carboxyl, ester, alkoxy, amino, cyano, azido, cyanato, nitro, amide, carboxyimido, nitroso, thiol, sulfinyl, sulfonyl, thial, phosphate, phosphono, boronic acid, optionally substituted aryl, and optionally substituted heterocycle; alternatively, $R^1$-$R^{12}$ are independently selected from the group consisting of optionally substituted ($C_1$-$C_3$)-alkyl, optionally substituted ($C_1$-$C_3$)-heteroalkyl, optionally substituted halo, hydroxyl, carboxyl, ester, alkoxy, amino, cyano, azido, nitro, and amide;

$R^{13}$ is an H, D, optionally substituted ($C_1$-$C_6$)-alkyl, alkoxy, cyano, hydroxyl, halo, or ester; alternatively, $R^{13}$ is an H, alkoxy, cyano, hydroxyl, halo, or ester; alternatively, $R^{13}$ is an H, hydroxyl or an ester; alternatively, $R^{13}$ is an ester;

$X^1$-$X^2$ are independently selected from a polyoxyalkylene polymer and an optionally substituted L-lysine, L-asparagine, and/or L-glutamine-based dendron that is functionalized on the outer layer by comprising histidine moieties, and aromatic amino acid moieties (e.g., phenylalanine, tryptophan, or tyrosine) and/or non-natural aromatic amino acids (e.g., napthlene and quinoline-based amino acids) moieties; alternatively, $X^1$-$X^2$ are independently selected from a polyoxyalkylene polymer and an optionally substituted L-lysine-based dendron that is functionalized on the outer layer by comprising histidine, and aromatic amino acid and/or non-natural aromatic amino acid moieties; alternatively, $X^1$-$X^2$ are independently selected from a polyoxyalkylene polymer and an optionally substituted L-lysine, L-asparagine, and/or L-glutamine-based dendron that is functionalized on the outer layer by comprising histidine and tryptophan moieties; alternatively, $X^1$-$X^2$ are independently selected from a polyoxyalkylene polymer and an optionally substituted L-lysine-based dendron that is functionalized on the outer layer by comprising histidine and tryptophan moieties; wherein at least one of $X$-$X^2$ is an optionally substituted L-lysine, L-asparagine, and/or L-glutamine-based dendron and wherein at least one of $X^1$-$X^2$ is a polyoxyalkylene polymer; alternatively, wherein at least one of $X^1$-$X^2$ is an optionally substituted L-lysine based dendron and wherein at least one of $X^1$-$X^2$ is a polyoxyalkylene polymer; wherein the ratio of histidine to aromatic amino acid (e.g., tryptophan) moieties is 2.5:1 to 1:1.

Examples of polyoxyalkylene polymers, include but are not limited to: triethylene glycol (TEG); polyethylene glycol (PEG); PEG which has been functionalized with various functional groups or organic molecules, including: halides, acetylenes, amines, azides, hydroxyls, thiols, methacrylates, acrylates, carboxylic acids, maleimides, mesylates, NHS esters, RAFT groups, tosylates, biotin or any combination of the foregoing; PEG diblock copolymers, including PEG-PLA, PEG-PLGA, PEG-PCL, PEG-PE, and PEG-PS; PEG triblock copolymers, including PEG-PPG-PEG, PPG-PEG-PPG, PLA-PEG-PLA, PLGA-PEG-PLGA, and PLCL-PEG-PLCL; poly(ethylene glycol-ran-propylene glycol); and poly(ethylene glycol-ran-propylene glycol) monobutyl ether. Most if not all of these polyoxyalkylene polymers are commercially available from various vendors, such as Sigma-Aldrich (St. Louis, Mo.). Furthermore, a person of ordinary skill in the art would recognize that these polymers can readily be incorporated into synthesis methods presented herein (e.g., Schemes 1-4) to produce a vector of the disclosure (e.g., a vector comprising TEG). Additionally, these polyoxyalkylene polymers come in various molecular weights and it is fully contemplated by this disclosure that any molecular size polyoxyalkylene polymer can be used to make a dendronized polymer of the disclosure. For example, PEG having an average molecular weight of about 200, about 300, about 400, about 600, about 1000, about 1450, about 1500, about 2000, about 3000, about 3350, about 4000, about 4600, about 5000, about 6000, about 8000, about 10000, about 12,000, about 20,000, about 35,000, or any range of molecular weights between or including any two of the foregoing values, can be used in the synthesis of a vector of the disclosure.

In a further embodiment, the disclosure provides for a vector comprising the structure of Formula I(a):

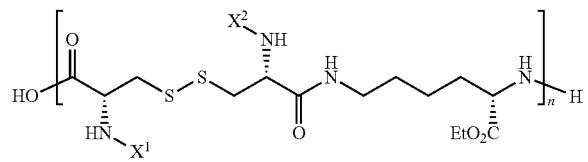

Formula I(a)

wherein, n is an integer greater than 50, 100, 200, 300, 400, 500, 1000, 500, 10000, 20000, or 50000;

$X^1$-$X^2$ are independently selected from the group consisting of (a) a structure of Formula II:

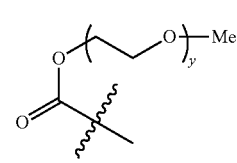

Formula II where y is an integer of 3, 6, 9, 10, 15, 20, 50, 100 or greater, and (b) a structure of Formula III:

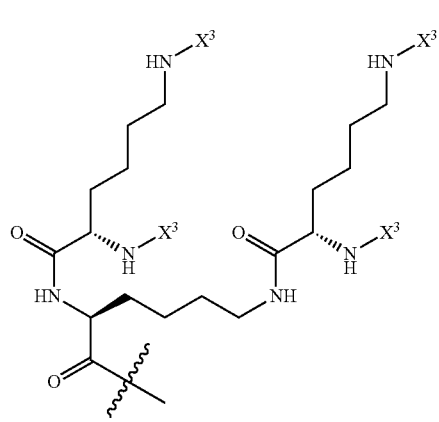

Formula III wherein, $X^3$ is a histidine moiety or an aromatic amino acid (e.g., tryptophan, phenylalanine, or tyrosine) moiety;

wherein at least one of $X^1$-$X^2$ is has the structure of Formula II and where at least one of $X^1$-$X^2$ has the structure of Formula III, and wherein the ratio of histidine to aromatic amino acid (e.g., tryptophan, phenylalanine, or tyrosine) moieties is 2.5:1 to 1:1.

In a particular embodiment, a vector disclosed herein has an N:P ratio between 5 to 45 (wherein the N:P ratio refers to the molar ratio of protonated amines of the vector:phosphates of the mRNA). In further embodiment, the N:P ratio is 5, 6, 7, 8, 9, 10, 11, 12, 13, 14, 15, 16, 17, 18, 19, 20, 25, 30, 35, 40, 45, or any range of N:P ratios between or including any two of the foregoing values. In a particular embodiment, the N:P ratio is 10.

The disclosure further provides that a "graft-from" approach can be used to produce the dendronized polymers of the disclosure. For example, dendronized polymers comprising the structure of Formula I can be made by following the generalized "graft from" method of Scheme 1:

Scheme 1
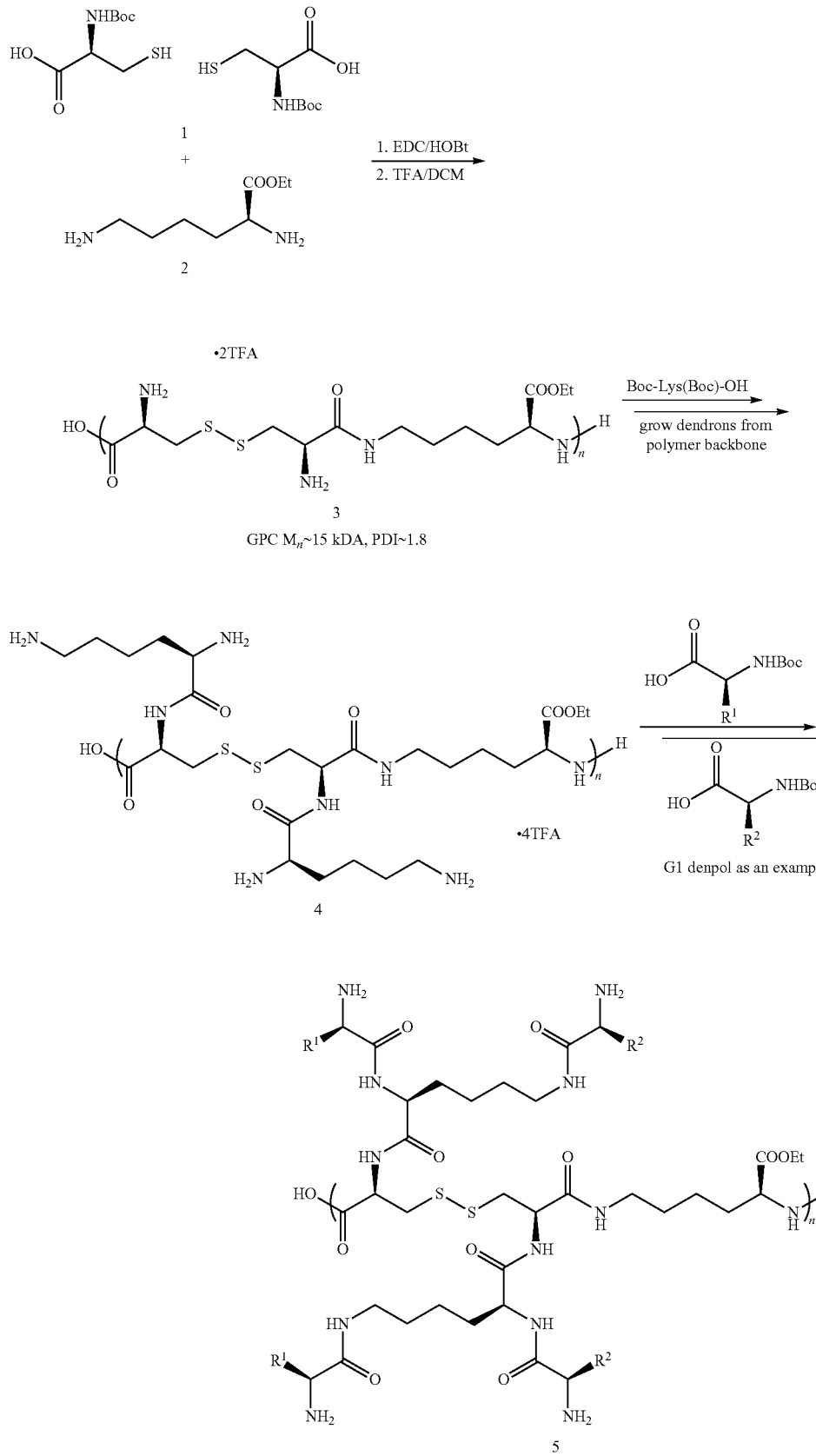

-continued

R¹:R²
2.5:1
2:1
1:1

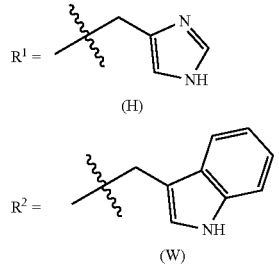

R¹ = (H)

R² = (W)

The backbone of vector is prepared by simple in situ peptide coupling polymerization between a dicysteine monomer 1 and a lysine monomer 2 (polymer Mn~15KD, PDI~1.8 by GPC). The disulfide linkages on the polymer backbone are introduced to be biodegradable under a reducing environment in the cytoplasm so as to facilitate nucleic acid decomplexation. After Boc deprotection, lysine-based dendrons were grown from the polymer backbone 4 generation by generation through solution phase peptide coupling. Finally, histidine and tryptophan amino acids at different molar ratios were coupled to the outer layer of the scaffold to introduce different functionalities 5. The chemical structures of the final denpols can then be characterized by 1H NMR analysis. Following this "graft-from" protocol, a small focused library of amphiphilic denpols was quickly generated. Throughout this disclosure, single letter amino acid codes will be used for naming. For example, G2 66H-34W represents a denpol with gen-2 dendrons composed of 66 mol % histidine (H) and 34 mol % tryptophan (W) residues on dendrons.

In an alternate embodiment, the disclosure provides a "combinatorial" approach can be used to produce the vectors of the disclosure. For example, vectors comprising the structure of Formula III can be made by following the generalized "combinatorial" method of Scheme 2:

Scheme 2

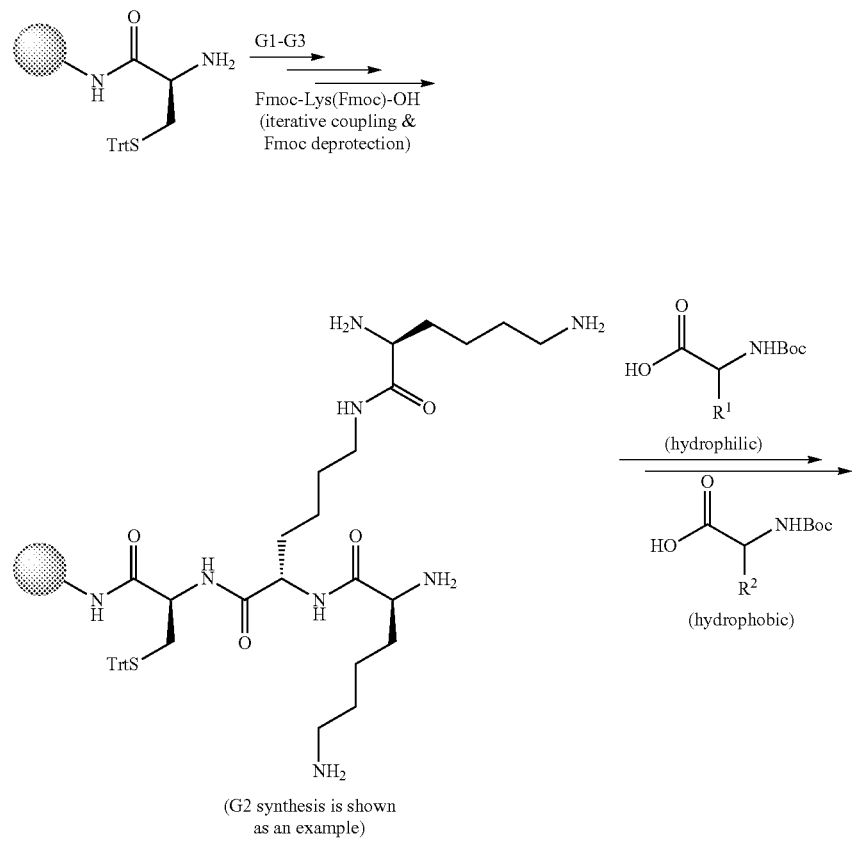

(G2 synthesis is shown as an example)

-continued

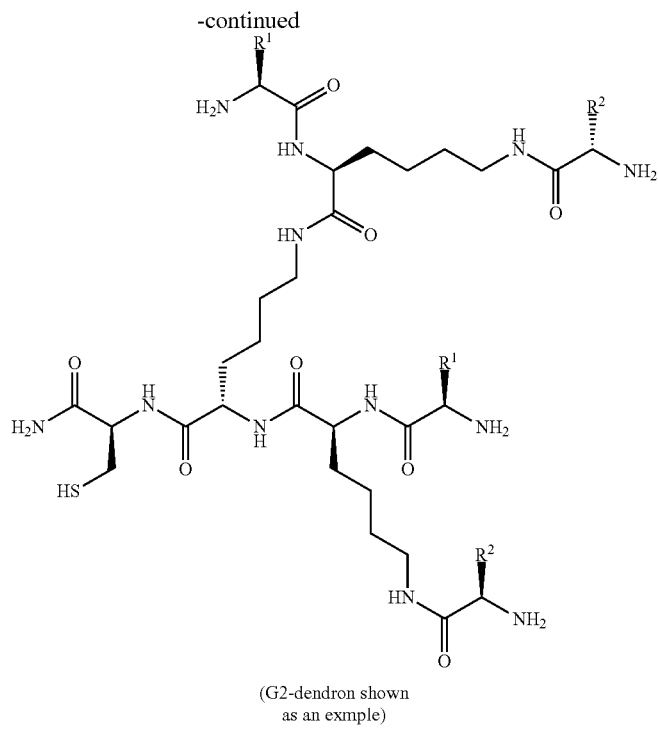

(G2-dendron shown as an exmple)

G1-G3 dendrons:

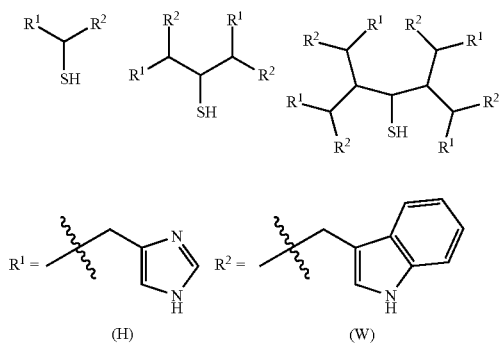

(H)        (W)

Oligolysine can be used to construct the polymer backbone. Oligolysine can easily be made by SPPS. Following procedure of Kantchev et al. (*Org Biomol Chem* 6(8): 1377-85 (2008)), a library of dendrons with controlled size and functionalities are synthesized by automated SPPS(Scheme 2). Briefly, Rink Amide Resin is first coupled with cysteine, which is then used as an anchoring group for grafting to the polymer backbone through a disulfide linkage. Lysine dendron is grown step by step until reaching the desired generation. Finally, the out layer is functionalized with a combination of histidine ($R_1$) and trytophan ($R_2$) amino acids. Each of the outer layer amino acid residues carries one positive charge from the α-amino group, providing the base level of cationic charge density for the vectors. Depending on the coupling protocol, the spatial placement of different functional groups on the dendrons can be precisely controlled. After acid cleavage, each individual dendron is purified and characterized. SPPS is ideally suited because it provides expedient access to a large library of dendrons.

In another embodiment, the disclosure provides a "graft-to" approach can be used to produce the vectors of the disclosure. For example, vectors comprising the structure of Formula IV can be made by following the generalized "graft-to" method of Scheme 3:

Scheme 3

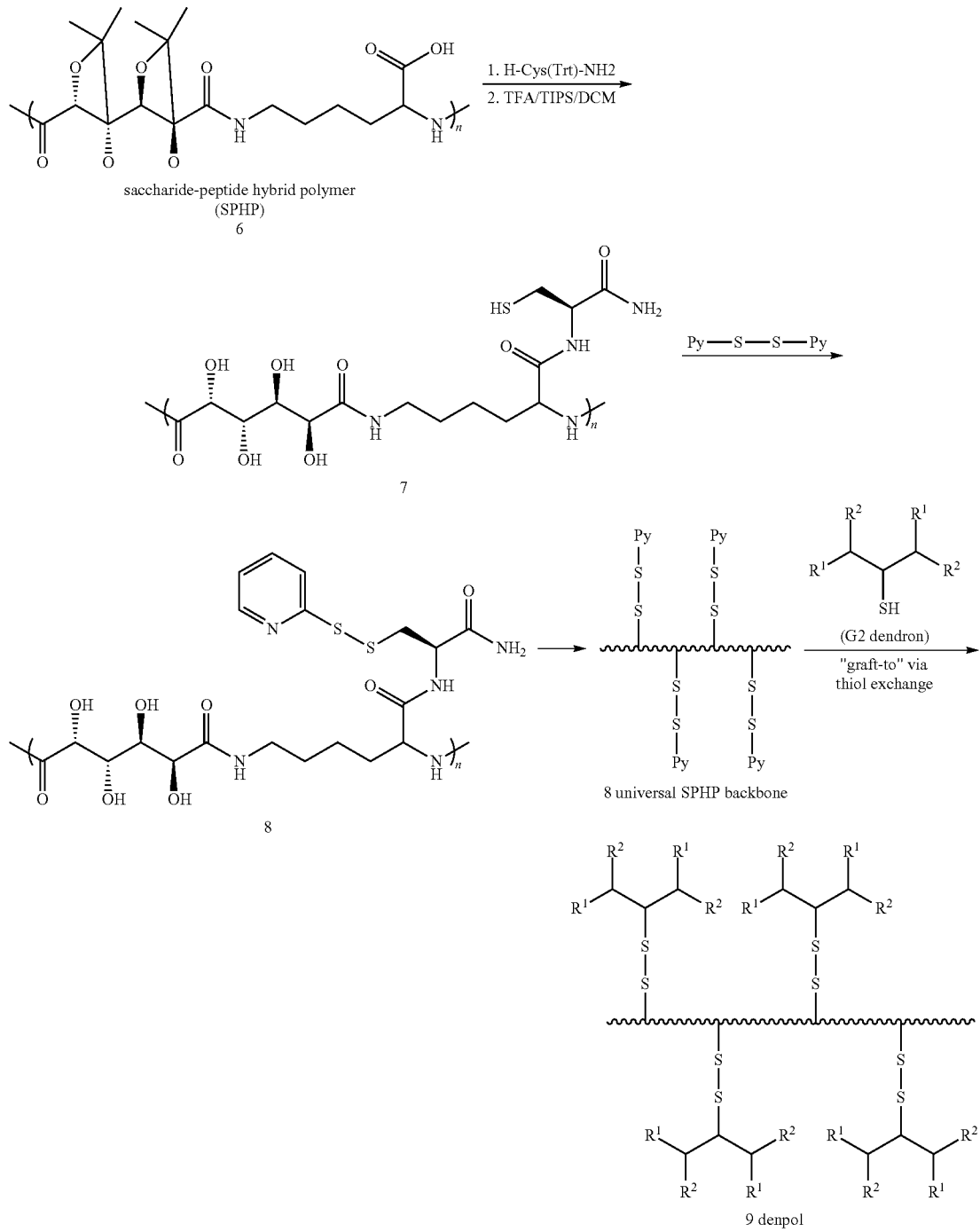

In another embodiment, the disclosure provides for systematic tuning of the spatial arrangement of the functional groups. The spatial placement of ligands can greatly affect the receptor binding and downstream biological response. A comparative study of the following three types of spatial arrangements (Scheme 4A-C) can be performed as follows to optimize the spatial arrangement of the functional groups to meet a specific application. First, a random hybrid dendron is prepared by adding a mixture of two different amino acids at the end of dendron synthesis (Scheme 2) to distribute the functional groups randomly on the outer layer (Scheme 4A). A uniform hybrid dendron is then prepared by using Fmoc-Lys(Cbz)-OH in dendron preparation. Selective deprotection and subsequent coupling allows for the precise placement of different functional group at each position on the outer layer (Scheme 4B). Two mono-functional dendrons are also prepared, which will be co-grafted onto the vector backbone at the desired ratio (Scheme 4C). All three types of vectors are prepared to have the same composition, and their biological properties are then compared in subsequent studies. Second, in conjugating dendrons onto the polymer backbone, the space between dendrons can be controlled by the grafting density, which is modulated by the molar ratio of dendron to polymer backbone. The remaining functional sites are capped by a concurrent reaction with 2-mercapto-ethanol ($HSCH_2CH_2OH$).

Scheme 4A-C

A. Random hybrid dendron

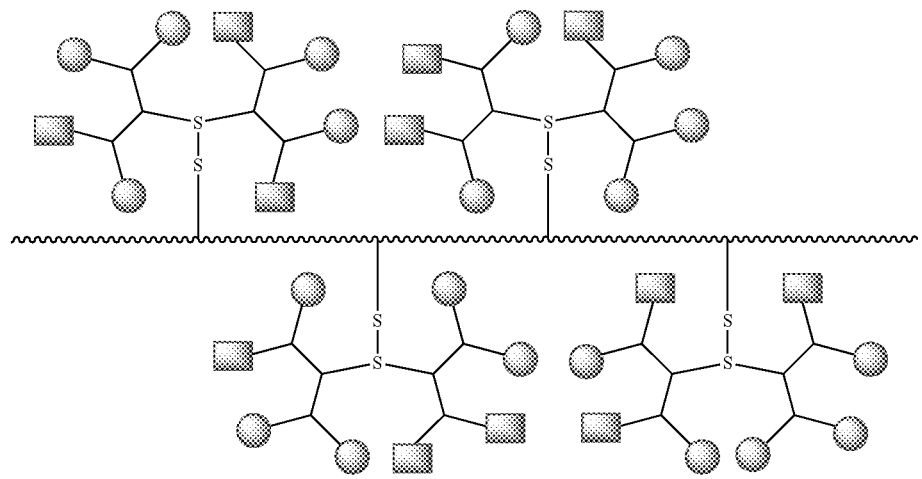

B. Uniform hybrid dendron

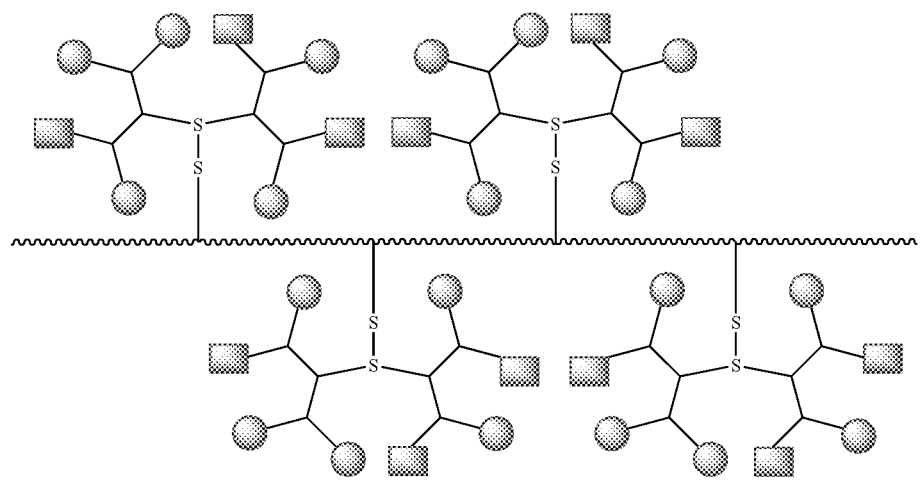

C. Mix of monofunctional dendrons

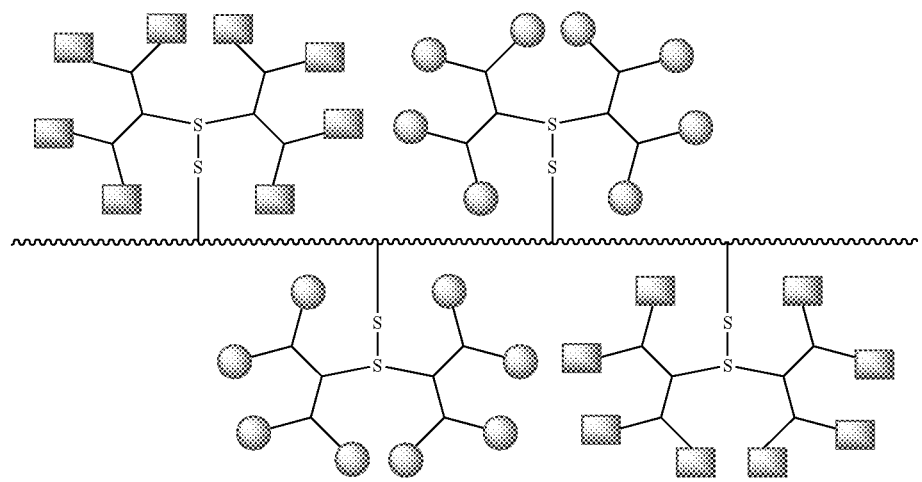

In a further embodiment, a vector disclosed herein further comprises targeting ligands. Examples of targeting ligands, include but are not limited to, antibodies, aptamers, cholesterol and its derivatives, folate compounds or folate conjugates, transferrin, saccharides (e.g., mono-, di-, oligo-saccharides), and cell-penetrating peptides. These targeting ligands can be conjugated to the dendronized polymers by using the techniques presented in Shu et al. (Annual Review of Physical Chemistry 64:631-657 (2013)), Gauthier et al. (Chem. Commun 23:2591-2611 (2008)), Menzel (*Advances in Polymer Science* 253:1-36 (2013)), Mero et al. (*Methods Mol Biol.* 751:95-129 (2011)), Roberts et al. (*Advanced Drug Delivery Reviews* 54:459-476 (2002)), Steenis et al. (*Journal of Controlled Release* 87:167-176 (2003)), which are incorporated herein in-full, including the references cited therein.

In any of embodiment disclosed herein, the vectors of the disclosure further comprise complexed ssRNA and/or mRNA. In a particular embodiment, the disclosure provides methods for delivering ssRNA and/or mRNA to a cell in vitro or in vivo comprising contacting the cell with a dendronized polymer that further comprises complexed ssRNA and/or mRNA.

In the experiments presented herein, the dendronized polymers of the disclosure can form complexes preferentially with ssRNA and/or mRNA, are stable in serum, allow for mRNA diffusion across the plasma membrane, and provide for endosomal escape. Accordingly, the dendronized polymers disclosed herein are particularly suited for delivering ssRNA and/or mRNA to cells. It should be noted that the ability of the vectors to complex with ssRNA and/or mRNA is based upon electrostatic and other forms of chemical interactions (intercalation) and is not based upon specific base pairing between the vector and ssRNA and/or mRNA. Accordingly, the vectors of the disclosure can be used with ssRNA and/or mRNAs in general, and is not limited to ssRNA and/or mRNAs having a specific sequence (e.g., the specific mRNAs used in the examples). Thus, the vectors have general utility as being able to effectively deliver ssRNA and/or mRNAs of any length or sequence into cells. Any number of ssRNAs and/or mRNAs are useful for diagnostics, therapeutics and research can be used in the methods and compositions of the disclosure. Particularly, the ssRNA and/or mRNA can be any length. For example, the vectors disclosed herein can be complexed with ssRNA and/or mRNA having a length of about 100 ribonucleotides, about 200 ribonucleotides, about 300 ribonucleotides, about 400 ribonucleotides, about 500 ribonucleotides, about 600 ribonucleotides, about 700 ribonucleotides, about 800 ribonucleotides, about 900 ribonucleotides, about 1000 ribonucleotides, about 1100 ribonucleotides, about 1200 ribonucleotides, about 1300 ribonucleotides, about 1400 ribonucleotides, about 1500 ribonucleotides, about 1600 ribonucleotides, about 1700 ribonucleotides, about 1800 ribonucleotides, about 1900 ribonucleotides, about 2000 ribonucleotides, about 2100 ribonucleotides, about 2200 ribonucleotides, about 2300 ribonucleotides, about 2400 ribonucleotides, about 2500 ribonucleotides, about 2600 ribonucleotides, about 2700 ribonucleotides, about 2800 ribonucleotides, about 2900 ribonucleotides, about 3000 ribonucleotides, about 4000 ribonucleotides, about 5000 ribonucleotides, about 6000 ribonucleotides, about 7000 ribonucleotides, about 8000 ribonucleotides, about 9000 ribonucleotides, about 10,000 ribonucleotides, about 15,000 ribonucleotides, about 18,000 ribonucleotides, about 20,000 ribonucleotides, about 30,000 ribonucleotides, about 40,000 ribonucleotides, about 50,000 ribonucleotides, about 60,000 ribonucleotides, about 70,000 ribonucleotides, about 80,000 ribonucleotides, about 90,000 ribonucleotides, about 100,000 ribonucleotides or about 120,000 ribonucleotides, or any range of ribonucleotides between or including any two of the foregoing values. Moreover, vectors described herein can be used to deliver multiple ssRNAs and/or mRNAs. For example, the vectors disclosed herein can be complexed with 1, 2, 3, 4, 5, 6, 7, 8, 9, 10, 15, 20, 30, 40, 100 or more different ssRNAs and/or mRNAs, or any range of different ssRNAs and/or mRNAs between or including any two of the foregoing values.

In a certain embodiment, the disclosure provides for a pharmaceutical composition which comprises a vector disclosed herein. Moreover, the pharmaceutical composition can be formulated into a form suitable for administration to a subject including the use of carriers, excipients, additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered at a therapeutically effective amount either locally or systemically. As used herein, "administering a therapeutically effective amount" is intended to include methods of giving or applying a pharmaceutical composition of the disclosure to a subject that allow the composition to perform its intended therapeutic function. The therapeutically effective amounts will vary according to factors, such as the degree of infection in a subject, the age, sex, and weight of the individual. Dosage regime can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (e.g., subcutaneous, intravenous, and the like), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. The composition will typically be sterile and fluid to the extent that easy syringability exists. Typically the composition will be stable under the conditions of manufacture and storage and preserved against the contaminating action of microorganisms, such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols, such as mannitol, sorbitol, or sodium chloride are used in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the subject's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. "Dosage unit form" as used herein, refers to physically discrete units suited as unitary dosages for the subject to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

In further embodiments disclosed herein, the vectors can be used with mRNAs in a variety of mRNA-based therapies, including to induce an immune response and potentiation, to replace or supplement proteins, to generate pluripotent stem cells, to genome engineer by using mRNA-encoded meganucleases, etc. In considering the advantages and disadvantages of mRNA-based therapy, there are several conceptual advantages compared to other nucleic acid-based approaches. Unlike DNA based therapy, mRNA does not have the risk of integration into the chromosomes, which can lead to insertional mutagenesis with potentially disastrous results. mRNA delivered therapeutically only results in transient translation that can be controlled by both changes in the UTRs or coding sequence and is completely degraded through physiologic pathways. This is considered both an advantage and a disadvantage depending on therapeutic needs. In principle, mRNA-based therapies appear to be much safer than DNA or viral and are applicable to a broad spectrum of disorders both acute and chronic. While DNA and RNA are both protein-encoding molecules that utilize cellular systems to produce the protein of interest, there are many differences in the use of mRNA versus DNA. The first involves the site of initial activity, which is the nucleus for plasmid DNA and the cytoplasm for mRNA. This represents a major difference between DNA and RNA, as DNA requires nuclear envelope breakdown during cell division to reach the nucleus and produce encoded protein, while mRNA only needs to reach the cytoplasm for translation. For mRNA to be translated into protein, it must survive in the extracellular space that contains high levels of ubiquitous RNases; it must reach or be targeted to the cells of interest for translation, and finally, it must cross the cell membrane. The cell membrane hinders passive diffusion of large negatively charged mRNA molecules. Although, it has been demonstrated that eukaryotic cells can actively engulf naked mRNA through a receptor mediated mechanism, in most cell types, the rate of uptake with transfer to the cytoplasm is extremely low, and naked mRNA has a very short half-life in tissues and fluids containing high levels of RNase activity. The vectors disclosed herein overcome these obstacles by providing for the effective delivery of mRNA to cells. In particular, the vectors complex with mRNA and protect the mRNA from degradation by extracellular RNases and increase cellular uptake of the mRNA, and further, by use of targeting peptides, the mRNA/vector complexes can be targeted to specific tissues and cell types. Therapeutically, mRNA/vector complexes may be directly conveyed into a subject's cells, ex vivo, to allow for more precise control of mRNA delivery, and then the transfected cells can be administered back to the patient. Alternatively, the mRNA/vector complex may be used in a suitable pharmaceutical composition disclosed herein and be directly administered in vivo to a subject.

The intrinsic immunogenicity of in vitro transcribed mRNA is viewed as advantageous in vaccine therapeutics due to its adjuvant activity that results in potent antigen-specific humoral and cellular immune responses. RNA has a distinctive pattern of immune stimulation, but this can be partially modulated by altering the characteristics (type and size) of the particle used to deliver it. The observation that naturally occurring RNAs differed in their immune activating potential and the level of immune activation correlated with the number of modified ribonucleotides contained in the RNA led to the finding that naturally occurring modified ribonucleotides that are modified to comprise pseudouridine, 5-methyluridine, 2-thiouridine, 5-methylcytidine (m5C), and N6-methyladenosine bases suppressed RNAs immunostimulatory effect by avoiding activation of TLR3, TLR7 and TLR8. The absence of the activation of RNA sensors led to mRNA that was translated at much greater levels (>1000-fold) in vivo without inducing proinflammatory cytokines, Type I interferons or adverse events and led to the current resurgence of nonvaccine mRNA therapeutics. Accordingly, it certain embodiments described herein, the vectors disclosed herein can be used with mRNAs that contain modified ribonucleotides so as to increase the translation of the mRNAs in vivo. For example, mRNAs disclosed herein can comprise any number of ribonucleotides that comprise modified bases such as pseudouridine, 5-methyluridine, 2-thiouridine, 5-methylcytidine (m5C), and/or N6-methyladenosine.

Direct addition of mRNA derived from tumor cells or encoding tumor specific antigens to dendritic cells (DCs) ex vivo followed by administration of DCs back to the host, followed this first demonstration of efficacy and led to extensive development leading to clinical trials. Multiple enhancements to this approach to therapy were attempted, including the addition of mRNAs encoding co-stimulators and cytokines. Some spectacular results have been reported, including the use of dendritic cells electroporated with melanoma-associated antigen fused to a HLA-class II targeting signal (DC-LAMP), adjuvanted with mRNAs encoding CD40 ligand, a constitutively active Toll-like receptor 4., and CD70, in treated melanoma patients where antitumor activity with durable disease control was observed. Tumor-derived mRNA loaded DCs have entered a Phase III clinical trial for patients with advanced renal cell cancer. Accordingly, the vectors disclosed herein can be used to transfect dendritic or other cells ex vivo from a subject with one or more tumor-derived mRNAs or other carcinoembryonic antigen mRNAs so as to induce an immune protective response against cancer cells in the subject. Additionally, the vectors disclosed herein can be used to transfect dendritic or other cells ex vivo from a subject with one or more infectious agent-derived mRNAs (e.g., mRNAs from viruses, bacteria, protozoa, or fungi) so as to induce an immune protective response by the subject against the infectious agent.

Environmental allergic diseases are a hypersensitivity disorder of the immune system mediated by IgE antibodies. Current treatments involve immunization with graded dosing of the allergen to modulate the type of T cell response and induce IgG antibodies that compete and inhibit IgE binding to allergens. New and effective, but very costly, alternatives involve the injection of anti-IgE monoclonal antibody. The molecular identification of the most common antigens leading to hypersensitivity has allowed the development of recombinant vaccine methods. mRNA encoding allergen vaccination prompted long-lasting allergen specific Th1 immune responses that protected mice from allergen exposure-mediated inflammation of the lung. Accordingly, the vectors disclosed herein can be used to transfect dendritic or other cells ex vivo from a subject with mRNAs encoding one or more allergenic antigens (e.g., antigens associated with peanuts, milk, latex, ragweed, shellfish, mold, dust mites, grasses, pollen, etc.) so as to promote long-lasting allergen specific Th1 immune responses in the subject.

In 2010, mRNAs coding for the Yamanaka stem cell factors (Oct3/4, Sox2, Klf4, c-Myc) containing pseudouridine and 5-methylcytydine were used to efficiently reprogram cells to pluripotency (iPS cells) without any integration events. A number of variants using the nucleoside modified mRNA approach have been described that claim a more effective induction of pluripotent stem cells or cell fate conversion. Prior to the use of nucleoside modified mRNA with its lack of innate immune signaling, mRNA was already being used to induce iPS cells, because of its high in vitro transfection efficiency and transient expression with lack of genomic integration. The transient expression of iPS factors makes the use of nucleoside-modified mRNA for creating iPS cells attractive for different fields, including disease modeling and therapy for a variety of diseases with potential application to treatment. Accordingly, the vectors disclosed herein can be used to re-program somatic cells to iPS cells by efficiently delivering mRNAs encoding re-programming factors into the somatic cells. Examples of re-programming factors, include but are not limited to, Oct3/4, Sox1, Sox2, Sox3, Sox15, Sox18, Klf1, Klf2, Klf4, Klf5, n-Myc, 1-Myc, c-Myc, Nanog, LIN28, and Glis 1. The mRNA sequences for all of the foregoing factors are publicly accessible and viewable via GenBank.

mRNA therapeutics can be viewed as a form of transient gene therapy without the potential complications of long-term gene therapy, including insertional mutagenesis, vector immunity and effects of viral replication on cell function. The delivery of therapeutic proteins by mRNA is an obvious therapeutic objective. The delivery of such encoded proteins can be initially divided between extracellular acting and systemic proteins versus intracellular acting proteins and then further divided based on; short-term delivery to treat deficient or non-functional proteins; long-term replacement of deficient or non-functional proteins; delivery of exogenous therapeutic proteins (monoclonal antibodies), and acute site-specific or systemic delivery of a protein during a medical emergency or therapeutic procedure. Accordingly, the vectors described herein can be used to deliver one or more mRNAs that encode therapeutic protein(s) (e.g., insulin, Factor IX) for protein replacement.

Early forms of gene therapy for the repair of inborn errors of a particular gene sought to replace the defective gene by delivering a functional copy containing its own promoter and regulatory regions and inserting it into the chromosomes using a viral vector. Genome editing has emerged as a potential alternative for gene therapy. Zinc finger nucleases and transcription activator-like effector nucleases use meganucleases linked to protein sequences that bind to specific DNA sequences that allows site specific cutting of DNA in chromatin. The CRISPR/cas9 system is derived from the acquired immune system of certain bacteria that uses RNA tags linked to a protein with nuclease activity called cas9. The RNA tags identify the site for cutting. The major adverse event encountered in all forms of gene editing is the risk of nonspecific editing. The amount of off-site effects associates with increasing duration of functional enzyme as mediated by plasmid or viral delivery systems. All three of the gene editing technologies only require the nucleases to be present for a short duration, thus, their transient expression from encoding mRNA would meet this criterion and likely minimize the potential for nonspecific effects. mRNAs encoding cas9, transcription activator-like effector nucleases and zinc finger nucleases and ZFNa have been successfully used to edit genomes ex vivo in embryonic cells from different species and in vivo in rodents and zebrafish. For all three gene editing approaches, the use of mRNA either by direct injection in vivo or ex vivo treatment would allow the fine tuning of dosing that cannot be achieved with plasmid and viral delivery. The additional advantages of high transfection efficiency without cell toxicity would be beneficial for the generation of transgenic animals and the treatment of human genetic diseases with potential application to other types of diseases, including cancer. Accordingly, the vectors disclosed herein can complexed with one or more mRNA that encode engineered nucleases, such as mRNAs that encode cas9 (see FIG. 54), transcription activator-like effector nucleases, zinc finger nucleases and ZFNa. The mRNA sequences for all of the foregoing engineered nucleases are publicly accessible and viewable via GenBank.

It should be further understood, that the vectors described herein can be used in vitro to effectively deliver/transfect cells with ssRNAs and/or mRNAs. Thus, the vectors can be used in any biological or diagnostic assay that may require a step of transfecting a cell with ssRNA and/or mRNA.

For use in the therapeutic or biological applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more vectors described herein, optionally in a composition or in combination with another agent (e.g., mRNA and/or ssRNA) as disclosed herein. The container(s) optionally have a sterile access port (for example the container can be an intravenous solution bag or a vial having a stopper pierceable by a hypodermic injection needle). Such kits optionally comprise an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The following examples are intended to illustrate but not limit the disclosure. While they are typical of those that might be used, other procedures known to those skilled in the art may alternatively be used.

Examples

Materials.

Unless otherwise noted, all reagents were used as received from commercial suppliers without further purification. Protected amino acids were purchased from Advanced ChemTech (Loiusville, Ky.) and Aroz Technologies, LLC. (Cincinnati, Ohio). Coupling reagents were purchased from GL Biochem Ltd. (Shanghai, China). FLuc mRNA (5meC, Ψ), Cyanine 5 FLuc mRNA (5meC, Ψ), and Cyanine 5 EGFP mRNA (5meC, Ψ) were obtained from TriLink Biotechnologies (Sorrento Mesa, Calif.). Lipofectamine MessangerMAX was purchased from Invitrogen (Carlsbad, Calif.). Pierce™ LDH Cytotoxicity Assay Kit was purchased from ThermoFisher (San Jose, Calif.). All reactions were performed using HPLC grade solvents unless otherwise noted. All water used in biological experiments was nanopure water obtained from Barnstead Nanopure Diamond (Waltham, Mass.). Unmodified NIH 3T3 cells were a generous gift from Professor Young Jik Kwon (Department of Chemical Engineering, UC Irvine, Calif.). Unmodified DC 2.4 cells and BMDCs were a generous gift from Professor Aaron Esser-Kahn's lab (Department of Chemistry, UC Irvine, Calif.). The BMDCs were harvested according to the procedure by Ryu et al. (*J. AM. Chem. Soc.* 136:10823 (2014)). Dulbecco's modified Eagle's medium (DMEM), fetal bovine serum (FBS), and OptiMEM were purchased from Invitrogen (Carlsbad, Calif.).

Instruments.

All materials were characterized by NMR. The molecular weight and molecular weight distribution of the Denpol backbone was measured by gel permeation chromatography (GPC). $^1$HNMR spectra were obtained using 500 and 600 MHz Bruker instruments. $^1$HNMR chemical shifts were reported as values in ppm relative to deuterated solvents indicated. GPC was performed on an Agilent 1100 SEC system using an OHpak SB-803 HQ column from Shodex. The molecular weight was determined with respect to poly (ethylene glycol) (PEG) S3 standards purchased from Aldrich. DMF with 0.1% LiBr (wt/v) was used as the eluent at a flow rate of 1.0 mL/min with column temperature at 45° C. The size and zeta potential of denpol/mRNA polyplexes were measured at 633 nm using Zetasizer (NanoZS) dynamic light scattering instrument (Malvern Instruments, Malvern, UK) at 25° C. with detection angle of 173°. Confocal images were obtained using a Ziess LSM 700

(Carl Zeiss AG, Oberkochen, Germany). Flow cytometry was performed on a BD ACCURI $C_6$ flow cytometer (BD Biosciences, San Jose).

Synthesis of the Denpol Backbone, G1 Backbone, and G2 Backbone.

The denpol backbone, G1 backbone, and G2 backbone were synthesized and characterized using the method by Zeng et al. (*J. Am. Chem. Soc.* 135:4962 (2013)).

Typical Procedure for Denpol Functionalization:

In a dram vial equipped with a stir bar, the specified DP (10.0 mg, 1.00 equiv) was dissolved in 1 mL of DMF. After the denpol backbone was completely dissolved, Boc-His(Boc)-OH, and Boc-Trp(Boc)-OH were added in the corresponding ratios. After all reagents had been solubilized, PyBOP (10.00 equiv.) and DIPEA (12.00 equiv.) were added, and the 1 dram vial was sealed with nitrogen and stirred over-night. After 12 h, 3 mL of MeOH was added to the reaction, and the mixture was purified via dialysis (MWCO=6-8 kD) against MeOH for 12 h. After 12 h the mixture was concentrated in vacuo (no heating), yielding a solid film. The Boc groups were removed by suspending the solid in a mixture of TFA (1.5 mL), DCM (0.75 mL), anisole (0.75 mL), and TIPS (0.1 mL) and stirring for 4 h under nitrogen. The mixture was concentrated in vacuo (no heating), re-suspended in methanol, and then precipitated in cold ether. The precipitate was pelleted via centrifugation, and the supernatant was discarded. The precipitate was purified via dialysis (MWCO=6-8 kD) against MeOH for 24 h and then concentrated in vacuo. All denpols were characterized by $^1$H NMR. The final functionalization ratio was calculated using the same methodology as reported in Zeng et al.

The Following Histidine Tryptophan Functionalized G2 Denpols were Synthesized:

G2 3:1 (77.4 H 22.6 W): Boc-His(Boc)-OH (6.00 equiv.) and Boc-Trp(Boc)-OH (2.00 equiv.). Clear colorless solid. 71% isolated yield.

G2 2:1 (66H 34 W): Boc-His(Boc)-OH (4.80 equiv.) and Boc-Trp(Boc)-OH (3.20 equiv.). Clear colorless solid. 62% isolated yield.

G2 1:1 (55 H 45 W): Boc-His(Boc)-OH (4.00 equiv.) and Boc-Trp(Boc)-OH (4.00 equiv.). Clear colorless solid. 89% isolated yield.

G2 1:2 (39 H 61 W): Boc-His(Boc)-OH (3.20 equiv.) and Boc-Trp(Boc)-OH (4.80 equiv.). Clear colorless solid. 78% isolated yield.

G2 1:3 (27H 73 W): Boc-His(Boc)-OH (2.00 equiv.) and Boc-Trp(Boc)-OH (6.00 equiv.). Clear colorless solid. 74% isolated yield Denpol G3 Backbone:

In a 25 mL RB flask equipped with a stir bar, DP G2 (76.3 mg, 1.00 equiv, 0.037 mmol) was dissolved in 4 mL of DMF. After the denpol backbone was completely dissolved, Boc-Lys(Boc)-OH DCHA was added. After all reagents had been solubilized, PyBOP (191.1 mg, 10.00 equiv., 0.37 mmol) and DIPEA (103.4 μL, 12.00 equiv., 0593 mmol) were added, and the flask was sealed with nitrogen and stirred over-night. After 12 h, 8 mL of MeOH was added to the reaction, and the mixture was purified via dialysis (MWCO=6-8 kD) against MeOH for 12 h. After 12 h the mixture was concentrated in vacuo (no heating), yielding a solid film. The Boc groups were removed by suspending the solid in a mixture of TFA (3.0 mL), DCM (1.5 mL), anisole (1.5 mL), and TIPS (0.2 mL) and stirring for 4 h under nitrogen. The mixture was concentrated in vacuo (no heating), suspended in methanol, and then precipitated in cold diethyl ether. The precipitate was pelleted via centrifugation, and the supernatant was discarded. The precipitate was purified via dialysis (MWCO=6-8 kD) against MeOH for 24 h and then concentrated in vacuo. Clear colorless solid. 93% isolated yield.

The Following Histidine Tryptophan Functionalized G3 Denpols were Synthesized:

G3 3:1 (71 H29 W): Boc-His(Boc)-OH (12.00 equiv.) and Boc-Trp(Boc)-OH (4.00 equiv.). Clear colorless solid. 93% isolated yield.

G3 2:1 (66 H 34 W): Boc-His(Boc)-OH (9.60 equiv.) and Boc-Trp(Boc)-OH (6.40 equiv.). Clear colorless solid. 91% isolated yield.

G3 1:1 (53 H 47 W): Boc-His(Boc)-OH (8.00 equiv.) and Boc-Trp(Boc)-OH (8.00 equiv.). Clear colorless solid. 82% isolated yield.

G3 1:2 (33 H 67 W): Boc-His(Boc)-OH (6.40 equiv.) and Boc-Trp(Boc)-OH (9.60 equiv.). Clear colorless solid. 78% isolated yield.

G3 1:3 (28H 72 W): Boc-His(Boc)-OH (4.00 equiv.) and Boc-Trp(Boc)-OH (12.00 equiv.). Clear colorless solid. 86% isolated yield.

Typical Procedure for Functionalization of Denpol G0 Backbone with TEG or PEG:

NHS-TEG-OMe and NHS-PEG2k-OMe was prepared according to Shirasaki et al. (J. Bioorg. Med. Chem. Lett. 18:5174 (2008)). In a 25 mL RB flask equipped with a stir bar, DP backbone (50 mg, 1.00 equiv., 0.083 mmol) was dissolved in 4 mL of DMF and DIPEA (57.6 L, 5.00 equiv., 0.330 mmol) was added. The reaction was cooled to 0° C. and the NHS-TEG-OMe or NHS-PEG-OMe was added in the corresponding amount. The flask was sealed with nitrogen and stirred for 4 h. After stirring, Boc-Lys(Boc)-OH DCHA (86.6 mg, 2.00 equiv., 0.165 mmol) and PyBOP (128.9 mg, 3.00 equiv. 0.248 mmol) are added. After 12 h, 8 mL of MeOH was added to the reaction, and the mixture was purified via dialysis (MWCO=6-8 kD) against MeOH for 12 h. After 12 h the mixture was concentrated in vacuo (no heating), yielding a solid film. The Boc groups were removed by suspending the solid in a mixture of TFA (3.0 mL), DCM (1.5 mL), anisole (1.5 mL), and TIPS (0.2 mL) and stirring for 4 h under nitrogen. The mixture was concentrated in vacuo (no heating), re-suspended in methanol, and then precipitated in cold diethyl ether. The precipitate was pelleted via centrifugation, and the supernatant was discarded. The precipitate was purified via dialysis (MWCO=6-8 kD) against MeOH for 24 h and then concentrated in vacuo. % TEG or PEG functionalization was determined via $^1$H NMR. % functionalization represents % of TEG or PEG per SRU. The compounds are named to represent which polymer (TEG or PEG) is functionalized off the backbone and in what percent.

G1 25 TEG: (23% by NMR) NHS-TEG-OMe (20.6 mg, 0.50 equiv., 0.0415 mmol). Clear colorless solid. 81% isolated yield.

G1 50 TEG: (42% by NMR) NHS-TEG-OMe (41.1 mg, 1.0 equiv., 0.083 mmol). Clear colorless solid. 68% isolated yield.

G1 75 TEG: (62% by NMR) NHS-TEG-OMe (61.7 mg, 1.50 equiv., 0.124 mmol). Clear colorless solid. 83% isolated yield.

Typical Procedure for Synthesis of G2 Lysine Dendrons on the TEGylated (or PEG) DP Backbones:

In a 25 mL RB flask equipped with a stir bar, DPBBTEG G1 (1.00 equiv) was dissolved in DMF. After the DPBBTEG G1 was completely dissolved, Boc-Lys(Boc)-OH DCHA (4.00 equiv) was added. After all reagents had been solubilized, PyBOP (6.00 equiv.) and DIPEA (8.00 equiv.) were added, and the flask was sealed with nitrogen and stirred over-night. After 12 h, 8 mL of MeOH was added to the reaction, and the mixture was purified via dialysis (MWCO=6-8 kD) against MeOH for 12 h. After 12 h the mixture was concentrated in vacuo (no heating), yielding a solid film. The Boc groups were removed by suspending the solid in a mixture of TFA (3.0 mL), DCM (1.5 mL), anisole (1.5 mL), and TIPS (0.2 mL) and stirring for 4 h under nitrogen. The mixture was concentrated in vacuo (no heating), resuspended in methanol, and then precipitated in cold diethyl ether. The precipitate was pelleted via centrifugation, and the supernatant was discarded. The precipitate was purified via dialysis (MWCO=6-8 kD) against MeOH for 24 h and then concentrated in vacuo.

G2 TEG 25: Clear colorless solid. 93% isolated yield.

G2 TEG 50: Clear colorless solid. 91% isolated yield.

G2 TEG 75: Clear colorless solid. 88% isolated yield.

The Following Histidine Tryptophan Functionalized TEG G2 Denpols were Synthesized:

G2 25 TEG 3:1 (74 H 26 W): Boc-His(Boc)-OH (4.62 equiv.) and Boc-Trp(Boc)-OH (1.54 equiv.). Clear colorless solid. 59% isolated yield.

G2 25 TEG 2:1 (63 H 32 W): Boc-His(Boc)-OH (4.01 equiv.) and Boc-Trp(Boc)-OH (2.16 equiv.). Clear colorless solid. 87% isolated yield.

G2 50 TEG 3:1 (73 H 27 W): Boc-His(Boc)-OH (3.48 equiv.) and Boc-Trp(Boc)-OH (1.16 equiv.). Clear colorless solid. 85% isolated yield.

G2 50 TEG 2:1 (64 H 36 W): Boc-His(Boc)-OH (3.02 equiv.) and Boc-Trp(Boc)-OH (1.62 equiv.). Clear colorless solid. 71% isolated yield.

G2 75 TEG 3:1 (71 H 29 W): Boc-His(Boc)-OH (2.28 equiv.) and Boc-Trp(Boc)-OH (0.76 equiv.). Clear colorless solid. 85% isolated yield.

G2 75 TEG 2:1 (61 H 39 W): Boc-His(Boc)-OH (1.98 equiv.) and Boc-Trp(Boc)-OH (1.06 equiv.). Clear colorless solid. 77% isolated yield.

Typical Procedure for Synthesis of G3 Lysine Dendrons on the TEGylated DP Backbones:

In a 25 mL RB flask equipped with a stir bar, DPBBTEG G2 (1.00 equiv.) was dissolved in DMF. After the DPBBTEG G2 was completely dissolved, Boc-Lys(Boc)-OH DCHA (8.00 equiv.) was added. After all reagents had been solubilized, PyBOP (10.00 equiv.) and DIPEA (12.00 equiv.) were added, and the flask was sealed with nitrogen and stirred over-night. After 12 h, 8 mL of MeOH was added to the reaction, and the mixture was purified via dialysis (MWCO=6-8 kD) against MeOH for 12 h. After 12 h the mixture was concentrated in vacuo (no heating), yielding a solid film. The Boc groups were removed by suspending the solid in a mixture of TFA (3.0 mL), DCM (1.5 mL), anisole (1.5 mL), and TIPS (0.2 mL) and stirring for 4 h under nitrogen. The mixture was concentrated in vacuo (no heating), resuspended in methanol, and then precipitated in cold diethyl ether. The precipitate was pelleted via centrifugation, and the supernatant was discarded. The precipitate was purified via dialysis (MWCO=6-8 kD) against MeOH for 24 h and then concentrated in vacuo.

G3 25 TEG Backbone: Clear colorless solid. 91% isolated yield.

G3 50 TEG Backbone: Clear colorless solid. 90% isolated yield.

G3 75 TEG Backbone: Clear colorless solid. 93% isolated yield.

The Following Histidine Tryptophan Functionalized TEG G3 Denpols were Synthesized:

G3 25 TEG 3:1 (73 H 27 W): Boc-His(Boc)-OH (9.24 equiv.) and Boc-Trp(Boc)-OH (3.08 equiv.). Clear colorless solid. 80% isolated yield.

G3 25 TEG 2:1 (64 H 36 W): Boc-His(Boc)-OH (8.01 equiv.) and Boc-Trp(Boc)-OH (4.31 equiv.). Clear colorless solid. 81% isolated yield.

G3 50 TEG 3:1 (74 H 26 W): Boc-His(Boc)-OH (6.96 equiv.) and Boc-Trp(Boc)-OH (2.32 equiv.). Clear colorless solid. 78% isolated yield.

G3 50 TEG 2:1 (64 H 36 W): Boc-His(Boc)-OH (6.03 equiv.) and Boc-Trp(Boc)-OH (3.24 equiv.). Clear colorless solid. 84% isolated yield.

G3 75 TEG 3:1 (73 H 27 W): Boc-His(Boc)-OH (4.56 equiv.) and Boc-Trp(Boc)-OH (1.52 equiv.). Clear colorless solid. 70% isolated yield.

G3 75 TEG 2:1 (62 H 38 W): Boc-His(Boc)-OH (3.95 equiv.) and Boc-Trp(Boc)-OH (2.13 equiv.). Clear colorless solid. 73% isolated yield.

G1 PEG 2k Backbones: See typical procedure for functionalization of denpol G0 backbone with TEG or PEG G1 1.0 PEG2k Backbone: NHS-PEG2k-OMe (0.01 equiv.). Clear colorless solid. 68% isolated yield.

G1 1.5 PEG2k Backbone: NHS-PEG2k-OMe (0.02 equiv.). Clear colorless solid. 59% isolated yield.

G1 3.0 PEG2k Backbone: NHS-PEG2k-OMe (0.05 equiv.). Clear colorless solid. 69% isolated yield.

The Following Histidine Tryptophan Functionalized PEG 2k G2 Denpols were Synthesized:

G1 1.0 PEG2k 2:1 (64 H 36 W): Boc-His(Boc)-OH (5.20 equiv.) and Boc-Trp(Boc)-OH (2.80 equiv.). Clear colorless solid. 67% isolated yield.

G1 1.5 PEG2k 2:1 (67H33 W): Boc-His(Boc)-OH (5.20 equiv.) and Boc-Trp(Boc)-OH (2.80 equiv.). Clear colorless solid. 74% isolated yield.

G1 3.0 PEG2k 2:1 (65 H 35 W): Boc-His(Boc)-OH (5.20 equiv.) and Boc-Trp(Boc)-OH (2.80 equiv.). Clear colorless solid. 68% isolated yield.

Denpol mRNA Transfection Protocol:

Before performing the mRNA transfections, the area was sterilized with bleach and RNAase ZAP™ (Ambion), and special care was take to use RNAase free products when handling the mRNA. Transfections were performed in triplicate in a cell culture treated clear-bottom 96-well plate (Corning). Lipofectamine messengerMAX™ was used as a positive control, and was prepared as instructed in the manual. After synthesis, characterization, and purification of DP, a 10 mg/mL solution was prepared using RNAase free water. DP and mRNA are mixed using the indicated N:P (Protonated primary amines on Denpol:Deprotonated phosphate groups on RNA) ratio. The mRNA was thawed and diluted to a concentration of 0.05 µg/µL with OptiMEM™. DP was added to a 200 µL vial. Next, the mRNA solution was added and mixed by pipetting up and down 10 times. Finally, the mixture is diluted with OptiMEM™ such that 20 µL will contain 200 ng of mRNA. The mixture was then incubated at room temperature for 5 minutes. During this time the culture media of the cells to be transfected was changed to 80 µL of 10% FBS in OptiMEM™. 20 µL of the mixture was then added to each well, and then the plate was returned to the incubator.

Imaging of FLuc mRNA Transfected Cells:

After the specified time of incubation with the transfection mixture, enough D-Luciferin was added to reach a concentration of 150 µg/mL. After addition, the cells were incubated for 5 minutes and then imaged using a IVIS camera to determine luminescence. After imagining the cells were discarded or the culture media was changed back to 10% FBS in DMEM if further experimentation was required.

Preparation of Samples for DLS:

The FLuc mRNA was thawed and diluted to a concentration of 0.05 μg/μL with low salt PBS buffer. DP was added to a 200 μL vial. Next, the mRNA solution was added and mixed by pipetting up and down 10 times. The mixture was diluted to 100 μL with low salt PBS The mixture was incubated at room temperature for 5 minutes. During the incubation, 80 μL of the selected media is added to a 100 μL cuvette. After 5 minutes 20 μL of the mRNA DP mixture is added to the cuvette and mixed via pipetting up and down 10 times. The cuvette is then placed in the instrument and the measurements are made.

Procedure for Confocal Microscopy:

Confocal laser microscopy was used to track cyanine-5 labeled mRNA in the transfected cells. Unmodified NIH 3T3 fibroblast cells were seeded at a density of 15000 cells/well on an 8-well chamber slide (Lab-Tek, Rochester, N.Y.) 24h before transfection. Cy-5 labeled mRNA was complexed with different denpols at an N:P of 10 and transfected to the cells under the aforementioned conditions. Confocal fluorescence spectroscopy was performed at 4 h and 24 h post transfection. The nucleus was counter-stained with 0.5 μg/mL solution of Hoechst 33342. All confocal images were acquired using a Zeiss LSM 700 inverted laser-scanning confocal microscope. A 63× plan apochromatic numerical aperture of 1.4 oil immersion DIC III objective or 20× plan apochromatic numerical aperture of 0.8 DIC II objective was used for all experiments. A 639 nm laser and a 606-700 nm band-pass filter were used to obtain the images of Cy-5 labeled mRNA. A 405 nm laser and a 400-498 nm band-pass filter were used to obtain the images of the Hoechst 33342 counter-stained nuclei. The fluorescent images were scanned separately and overlaid together with the differential interference contrast image (DIC). The cells were scanned as a z-stack of two-dimensional images (1024×1024 pixels) and an image cutting approximately through the middle of the cellular height was selected to present the intracellular mRNA localization.

Gel Shift Assay to Survey mRNA Binding:

The binding of mRNA to denpol was studied by agarose gel electrophoresis. Both mRNA and denpol were diluted with 10 mM pH 7.4 phosphate buffer. Different amount of denpol solutions (10 mg/mL) were added to 5 μL of a 0.04 μg/μL mRNA solution to achieve the specified N:P ratios. The same buffer was added to adjust the final volume to 10.0 μL, followed by 5 min incubation at room temperature. 2.5 μL 6× gel loading dye was added to each sample and 10 μL of the mixture was loaded to each well in 1% agarose gel with 1× GelRed™ dye. The electrophoresis was run in TAE buffer (pH 7.9) at 60 V for 45 min and the gel was visualized under a UV trans illuminator.

Flow Cytometry:

Before flow cytometry, the cells are harvested from the 96 well plate via trypsin for the 3T3 and DC 2.4 cells and pipetting for the BMDC cells followed by centrifugation. The cells are washed with PBS and spun down 3 additional times to remove excess Cy-5 labeled mRNA. 10000 events were recorded per sample. Each value reported is the average of 3 samples.

LDH:

NIH 3t3 cells seeded in a 96 well plate were treated with denpol mRNA nanoparticles at an N:P ratio of 30, formulated as specified above. After 24 h incubation with the nano particles, 50 μL of the supernatant was taken and cytotoxicity was measured using a Pierce™ LDH Cytotoxicity Assay Kit (ThermoFisher) as directed in the manual.

Characterization of Denpols:

$^1$HNMR of the polymer samples used a 10 second relaxation time to ensure chain relaxation and to help with resolution. Methanol and water were unable to be completely removed from the polymer samples. The actual percentage functionalization of the Denpols as determined by integration is listed after the name of the denpols. As the polymer samples become more functionalized, the spectra become complex and peak resolution becomes difficult. Unless fully resolved, ranges of peaks are listed.

Synthesis and Characterization of Denpols.

Figure 1:
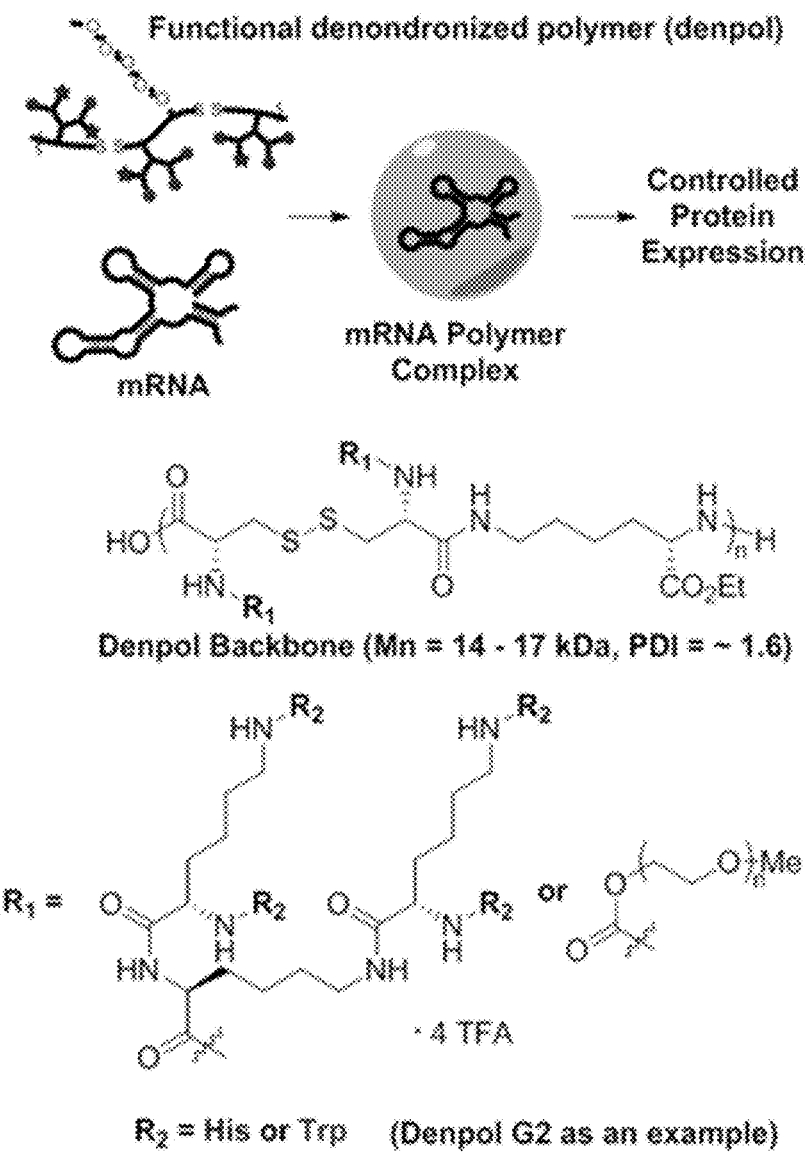
FIG. 1 provides an embodiment of the general structure of a dendronized polymer (denpol) and mRNA Polymer complexes.
Figure 2:
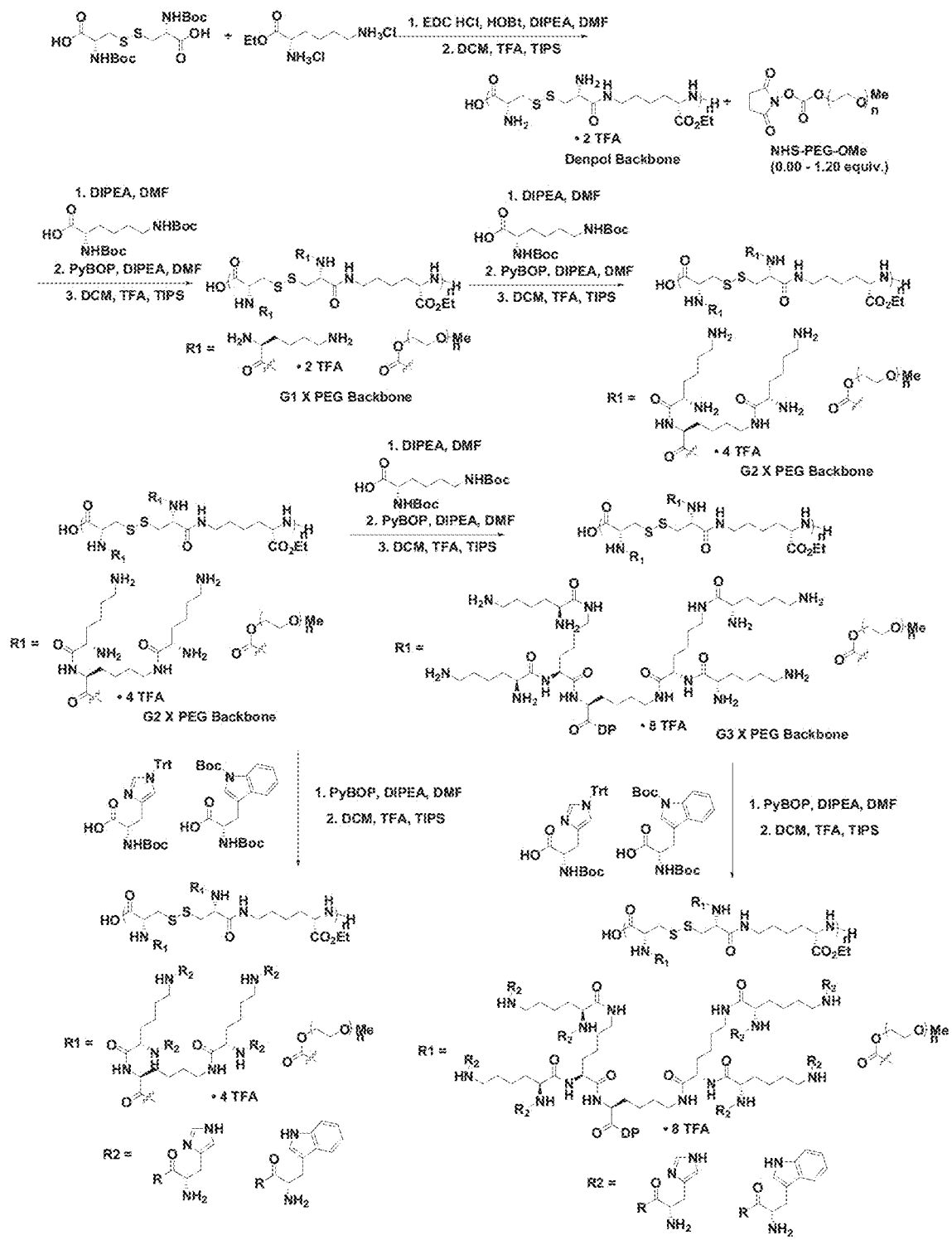
FIG. 2 presents a general synthetic scheme for Denpol production. Amounts of NHS-PEG-OMe and dendron on the surface of the denpol backbone are specified in the procedures.
Figure 3:
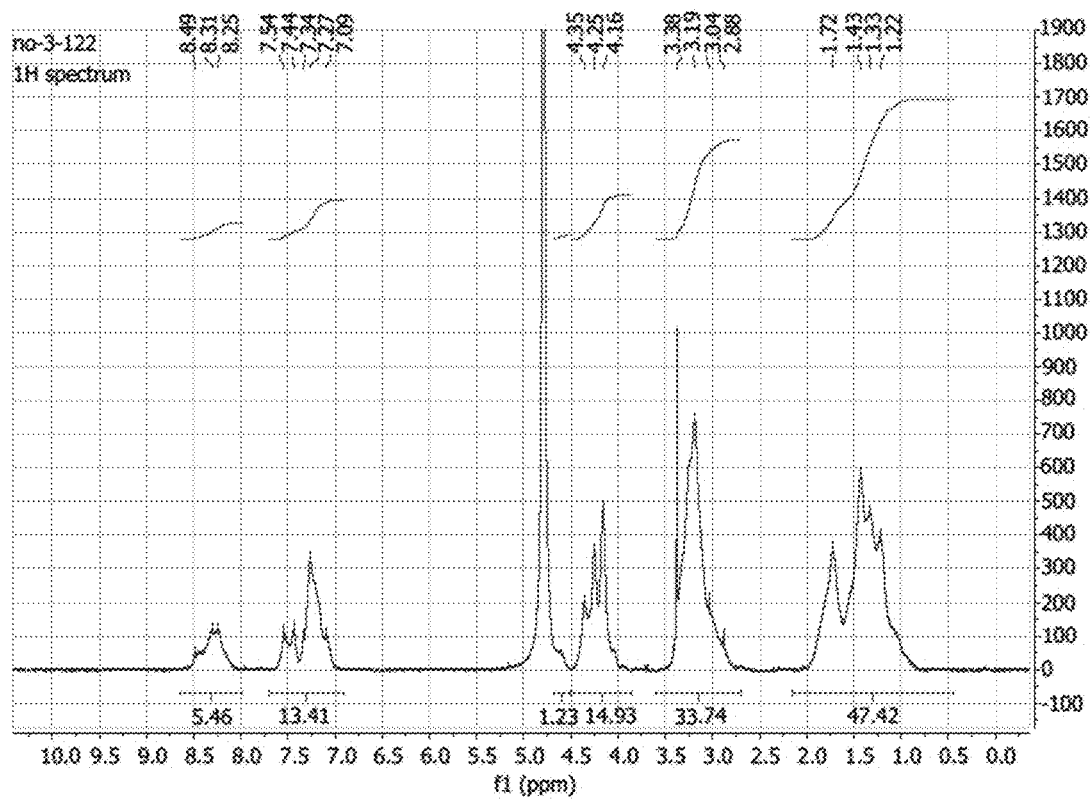
FIG. 3 provides a $^1$HNMR spectra of a denpol comprising a G2 3:1 (77 H 23 W). $^1$H NMR (600 MHz, D$_2$O) δ 8.61-7.97 (m, 5H), 7.70-6.95 (m, 13H), 4.67-4.52 (m, 1H), 4.52-3.87 (m, 15H), 3.53-2.62 (m, 34H), 2.07-0.71 (m, 48H).
Figure 4:
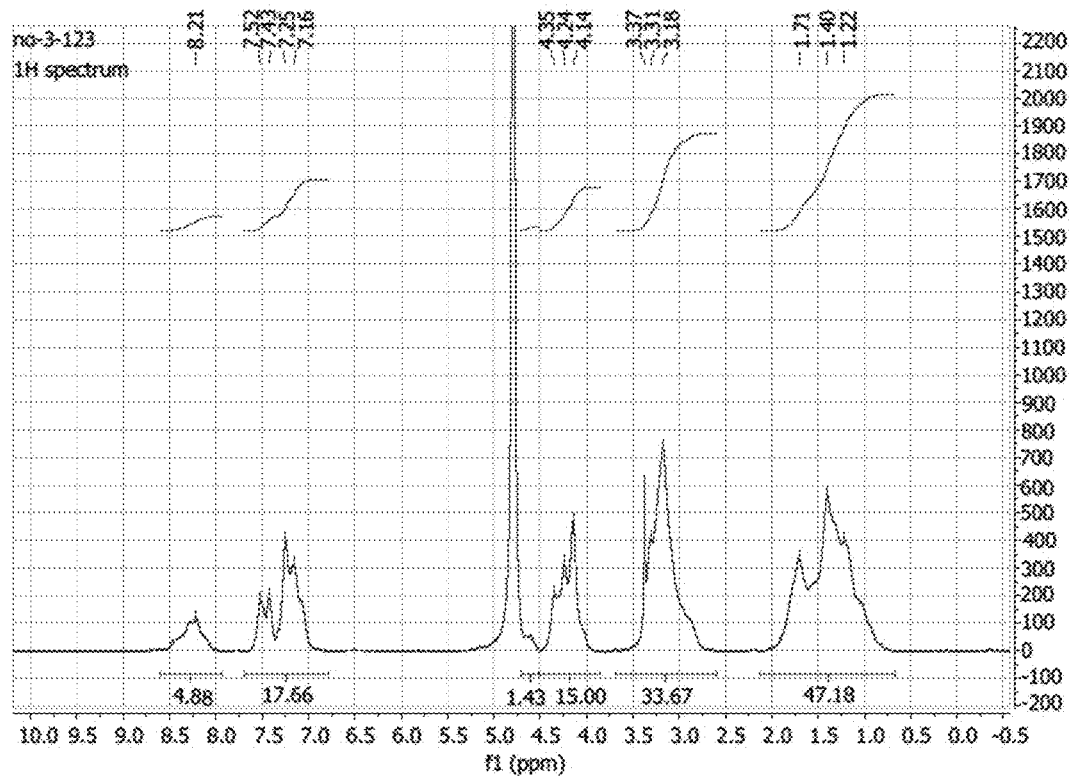
FIG. 4 provides a $^1$HNMR spectra of a denpol comprising a G2 2:1 (66 H 34 W). $^1$H NMR (600 MHz, D$_2$O) δ 8.58-8.01 (m, 5H), 7.70-6.88 (m, 18H), 4.67-4.49 (m, 1H), 4.49-3.86 (m, 15H), 3.64-2.69 (m, 34H), 2.09-0.67 (m, 47H).
Figure 5:
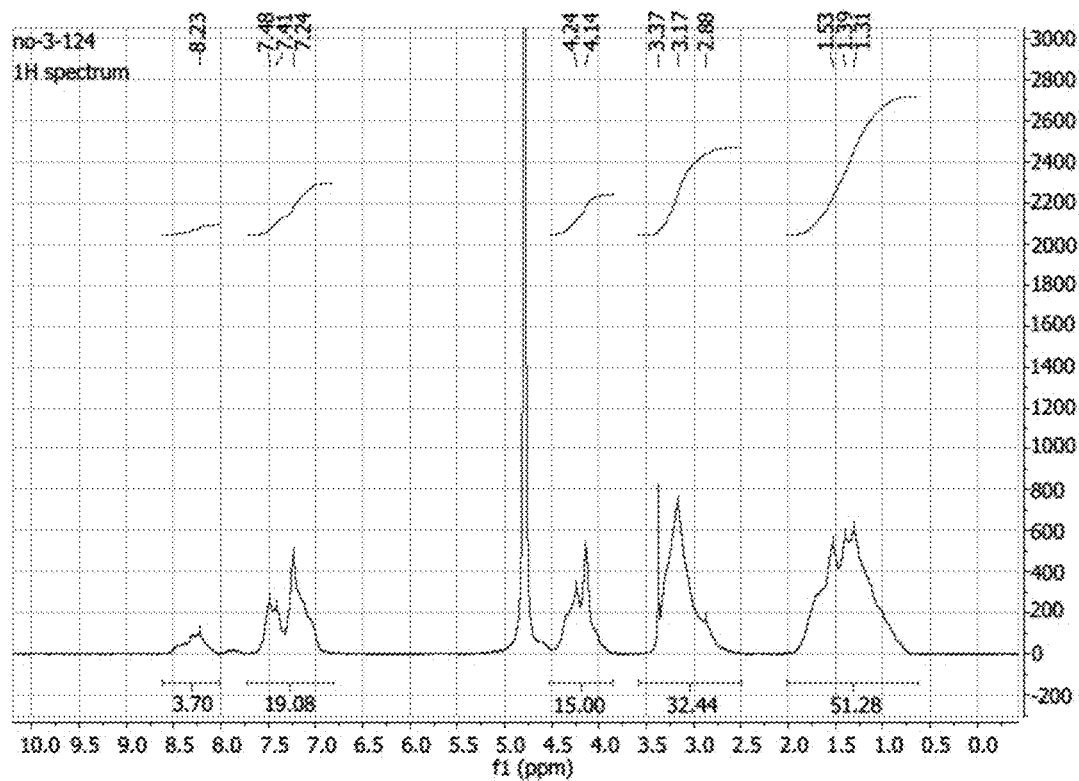
FIG. 5 provides a $^1$HNMR spectra of a denpol comprising a G2 1:1 (55 H 45 W). $^1$H NMR (600 MHz, D$_2$O) δ 8.66-8.02 (m, 4H), 7.69-6.82 (m, 19H), 4.66-4.52 (m, 1H), 4.49-3.87 (m, 15H), 3.47-2.54 (m, 33H), 2.02-0.63 (m, 52H).
Figure 6:
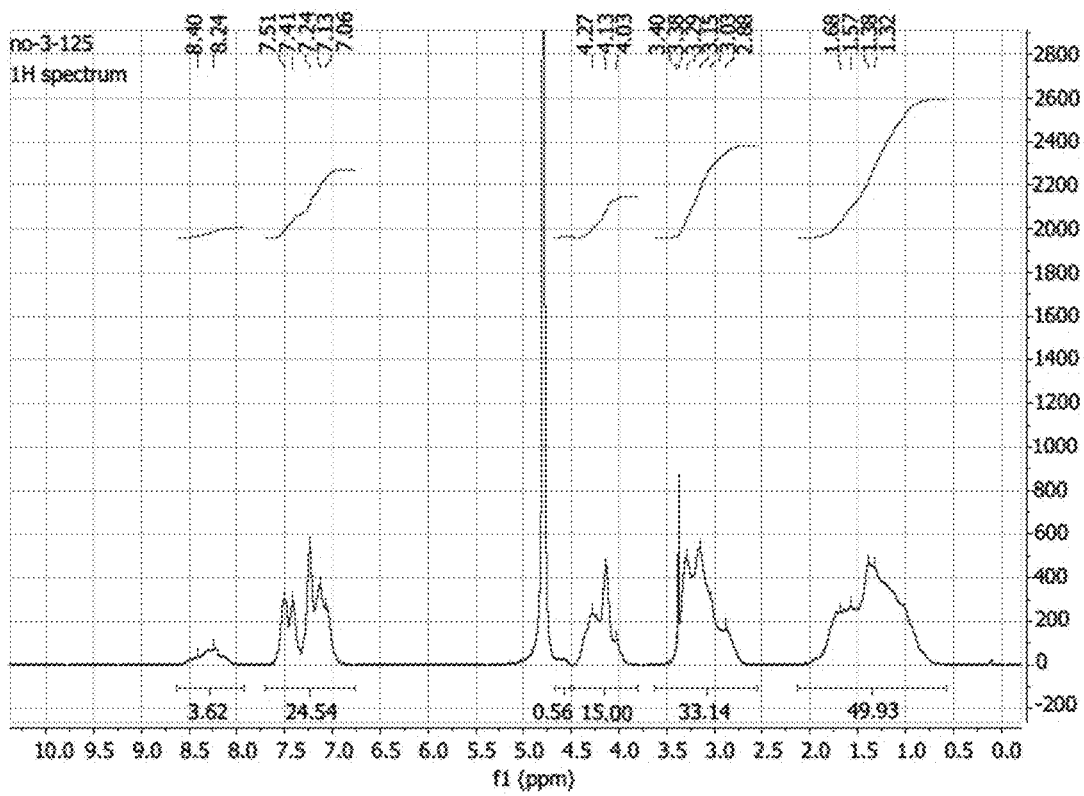
FIG. 6 provides a $^1$HNMR spectra of a denpol comprising a G2 1:2 (39 H 61 W). $^1$H NMR (600 MHz, D$_2$O) δ 8.62-7.95 (m, 4H), 7.67-6.80 (m, 25H), 4.64-4.49 (m, 1H), 4.50-3.82 (m, 15H), 3.59-2.60 (m, 33H), 2.09-0.60 (m, 50H).
Figure 7:
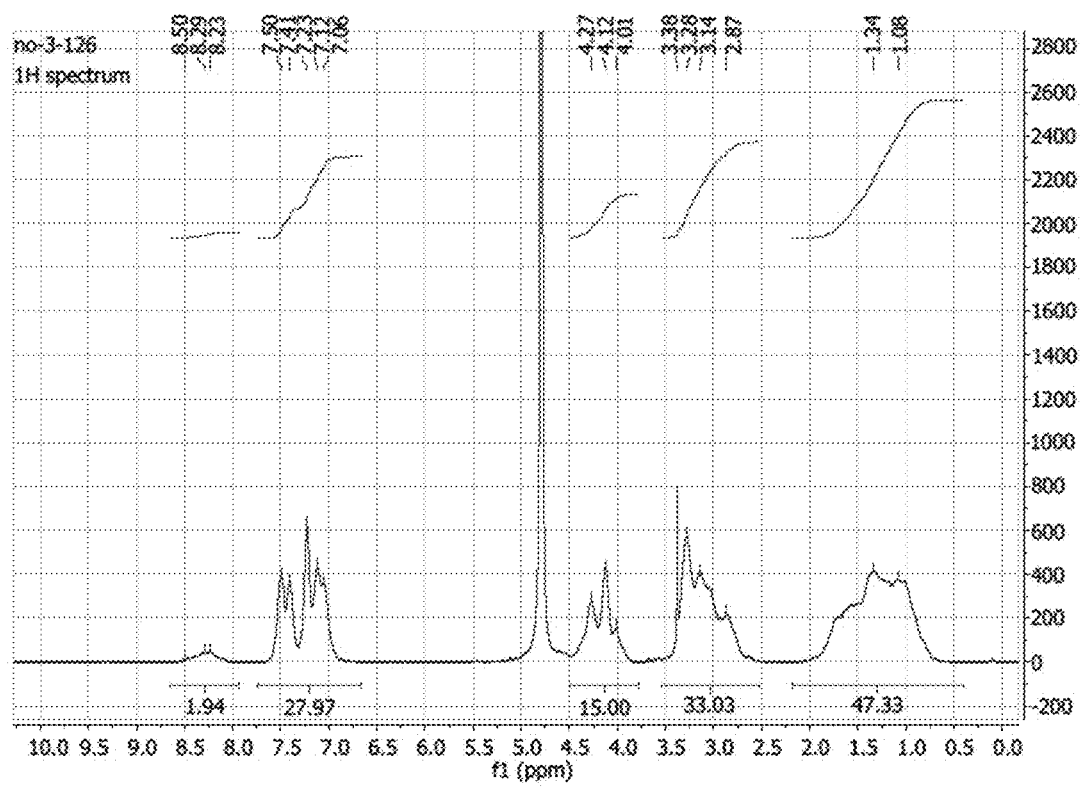
FIG. 7 provides a $^1$HNMR spectra of a denpol comprising a G2 1:3 (27 H 73 W). $^1$H NMR (600 MHz, D$_2$O) δ 8.61-7.95 (m, 2H), 7.70-6.75 (m, 28H), 4.67-4.49 (m, 1H), 4.51-3.79 (m, 15H), 3.71-2.50 (m, 33H), 2.05-0.54 (m, 47H).
Figure 8:
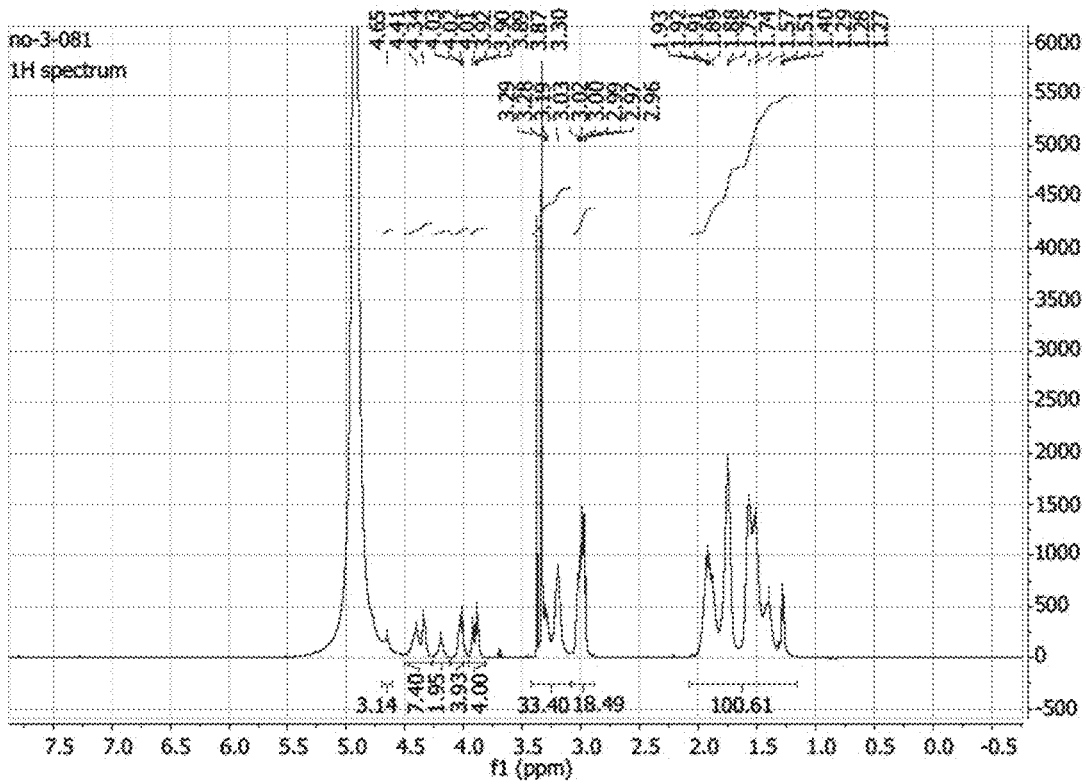
FIG. 8 provides a $^1$HNMR spectra of a denpol comprising a G3 Backbone. $^1$H NMR (600 MHz, CD$_3$OD) δ 4.74-4.56 (m, 5H), 4.57-4.28 (m, 8H), 4.27-4.08 (m, 2H), 4.13-3.96 (m, 4H), 3.96-3.81 (m, 4H), 3.45-3.09 (m, 34H), 3.09-2.85 (m, 19H), 2.16-1.07 (m, 101H).
Figure 9:
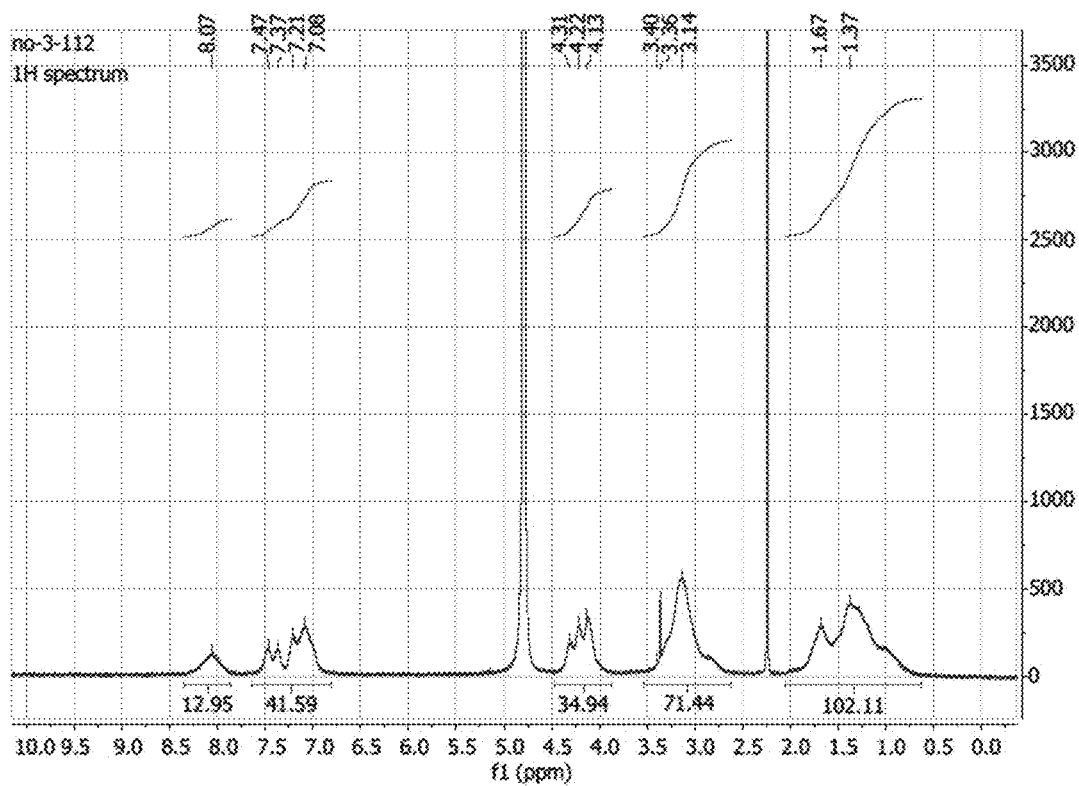
FIG. 9 provides a $^1$HNMR spectra of a denpol comprising a G3 3:1 (71 H 29 W). $^1$H NMR (600 MHz, D$_2$O) δ 8.44-7.77 (m, 14H), 7.66-6.81 (m, 43H), 4.66-4.52 (m, 2H), 4.43-3.89 (m, 35H), 3.52-2.61 (m, 73H), 2.08-0.55 (m, 105H).
Figure 10:
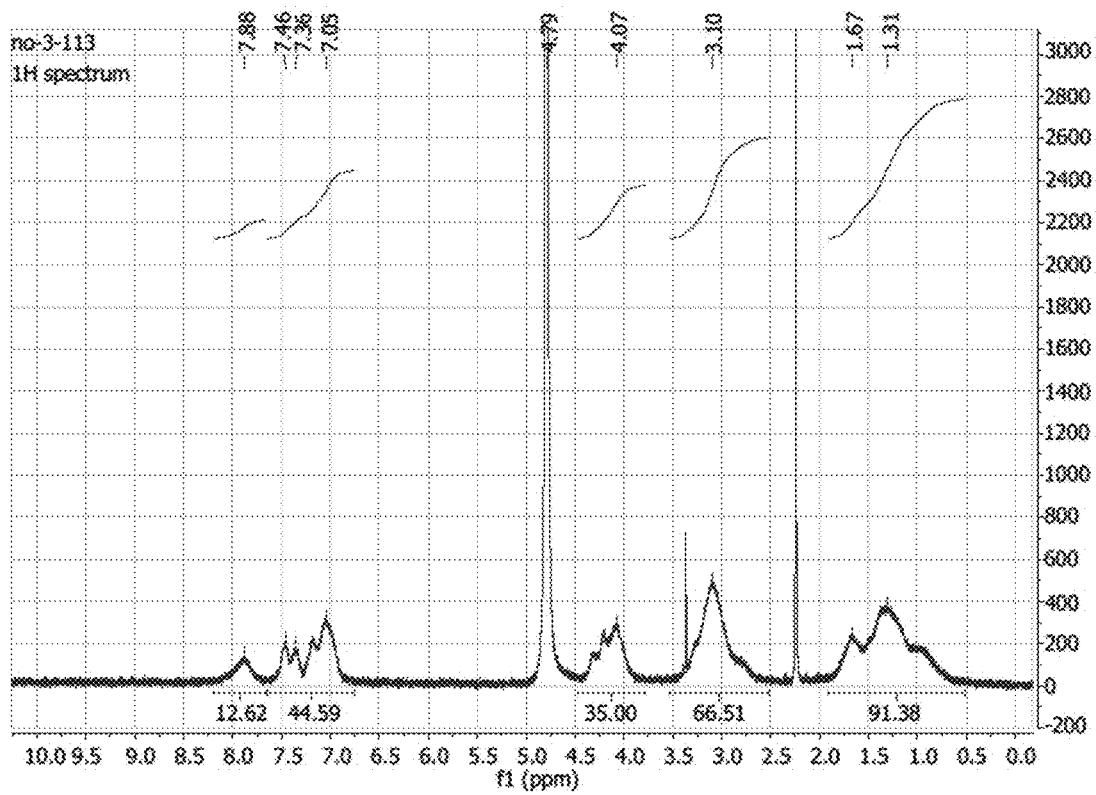
FIG. 10 provides a $^1$HNMR spectra of a denpol comprising a G3 2:1 (66 H 34 W). $^1$H NMR (600 MHz, D$_2$O) δ 8.21-7.69 (m, 12H), 7.69-6.71 (m, 45H), 4.52-3.80 (m, 35H), 3.52-2.61 (m, 64H), 2.10-0.38 (m, 93H).
Figure 11:
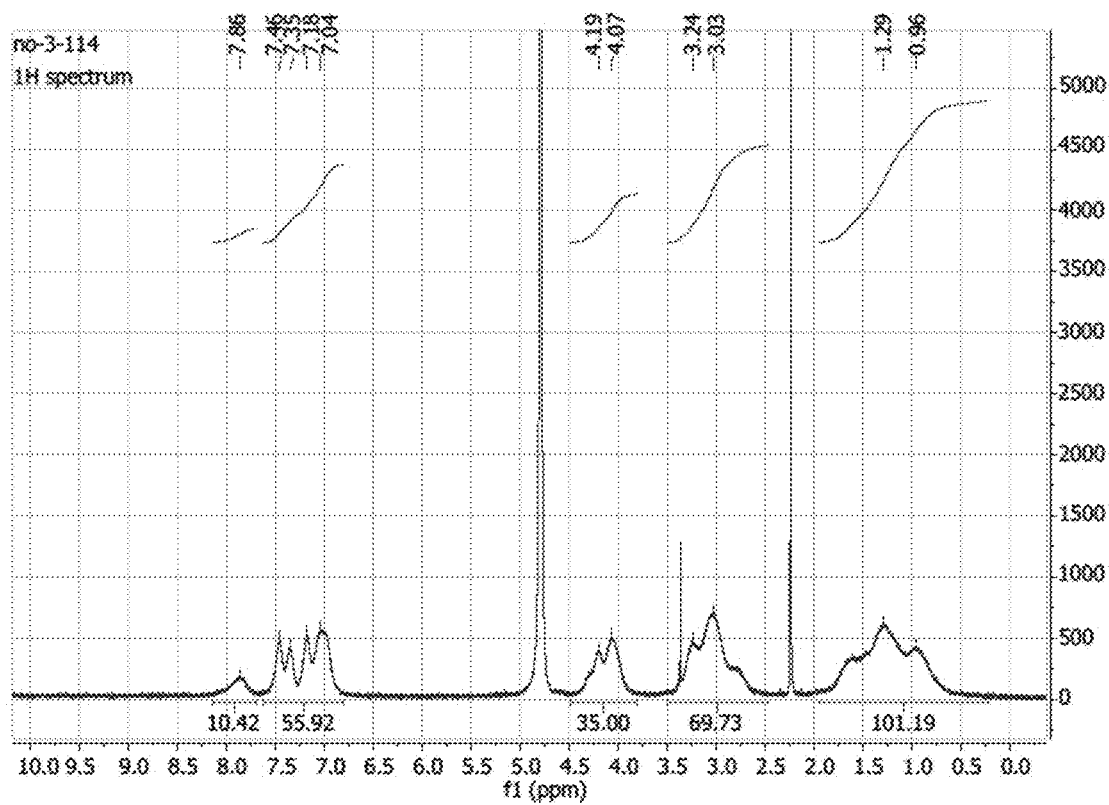
FIG. 11 provides a $^1$HNMR spectra of a denpol comprising a G3 1:1 (53 H 47 W). $^1$H NMR (600 MHz, D$_2$O) δ 8.17-7.67 (m, 11H), 7.63-6.68 (m, 57H), 4.48-3.79 (m, 35H), 3.49-2.51 (m, 69H), 2.00-0.43 (m, 100H).
Figure 12:
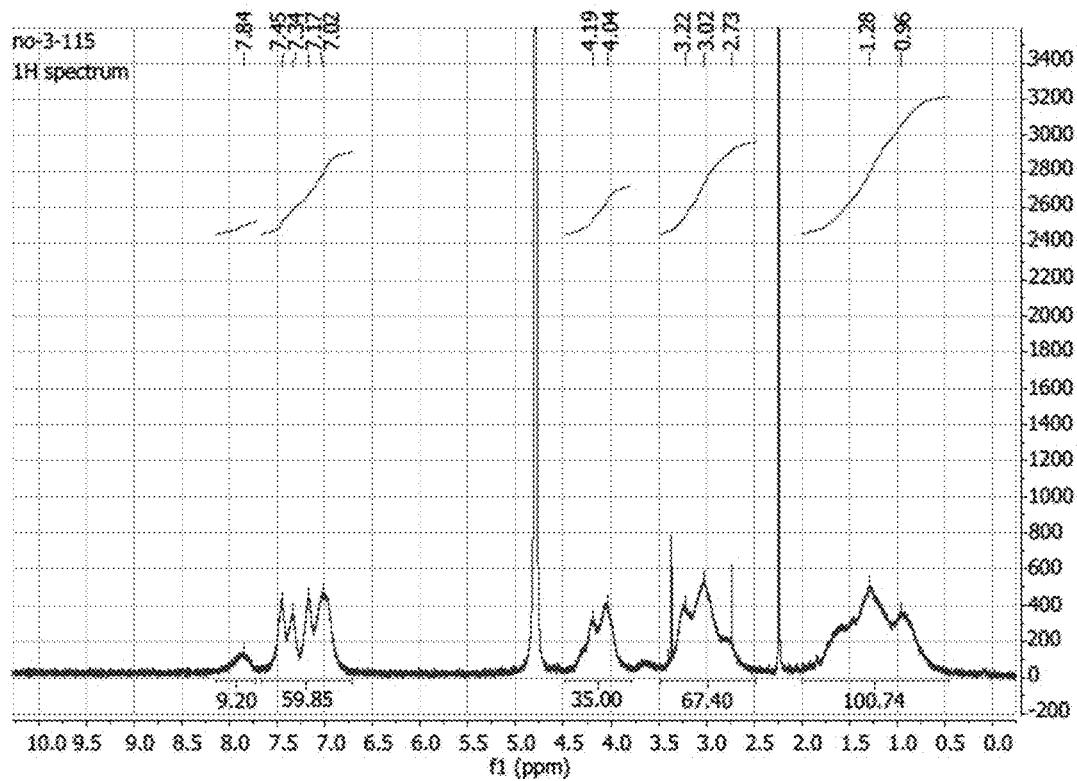
FIG. 12 provides a $^1$HNMR spectra of a denpol comprising a G3 1:2 (33 H 67 W). $^1$H NMR (600 MHz, D$_2$O) δ 8.22-7.69 (m, 11H), 7.67-6.70 (m, 61H), 4.44-3.79 (m, 35H), 3.47-2.47 (m, 68H), 1.96-0.42 (m, 102H).
Figure 13:
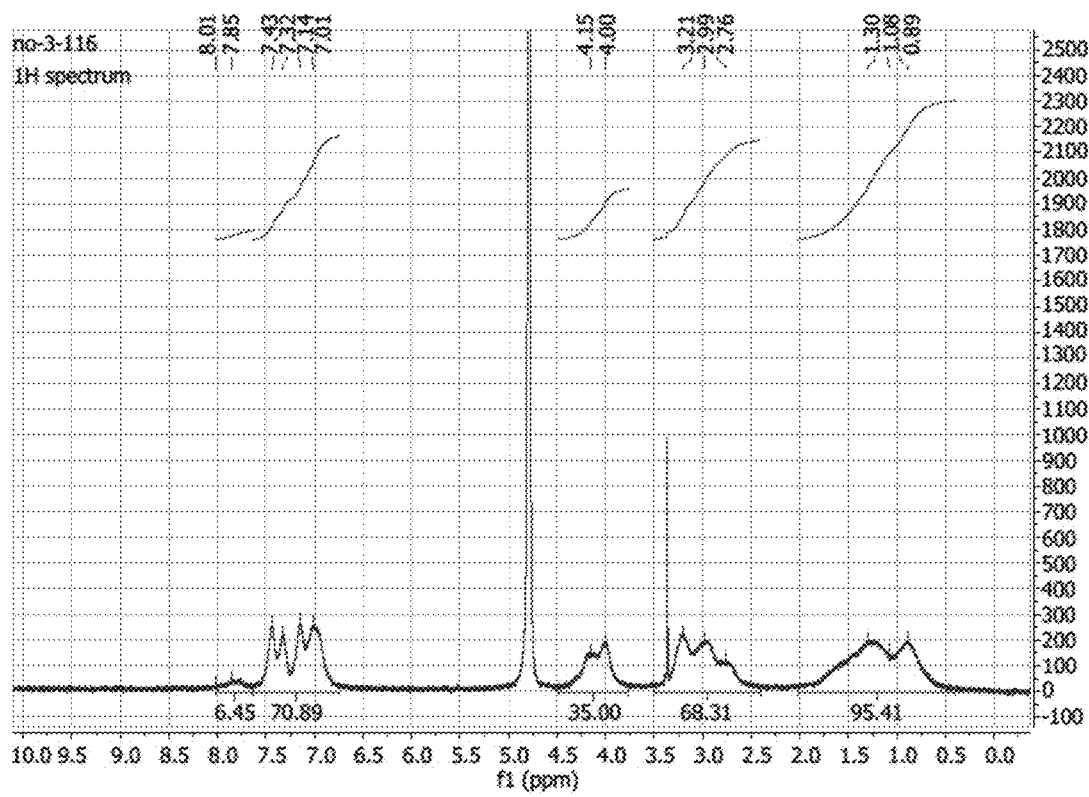
FIG. 13 provides a $^1$HNMR spectra of a denpol comprising a G3 1:3 (28 H 72 W). $^1$H NMR (600 MHz, D$_2$O) δ 8.04-7.66 (m, 6H), 7.63-6.70 (m, 70H), 4.49-3.73 (m, 35H), 3.47-2.39 (m, 67H), 1.95-0.45 (m, 93H).
Figure 14:
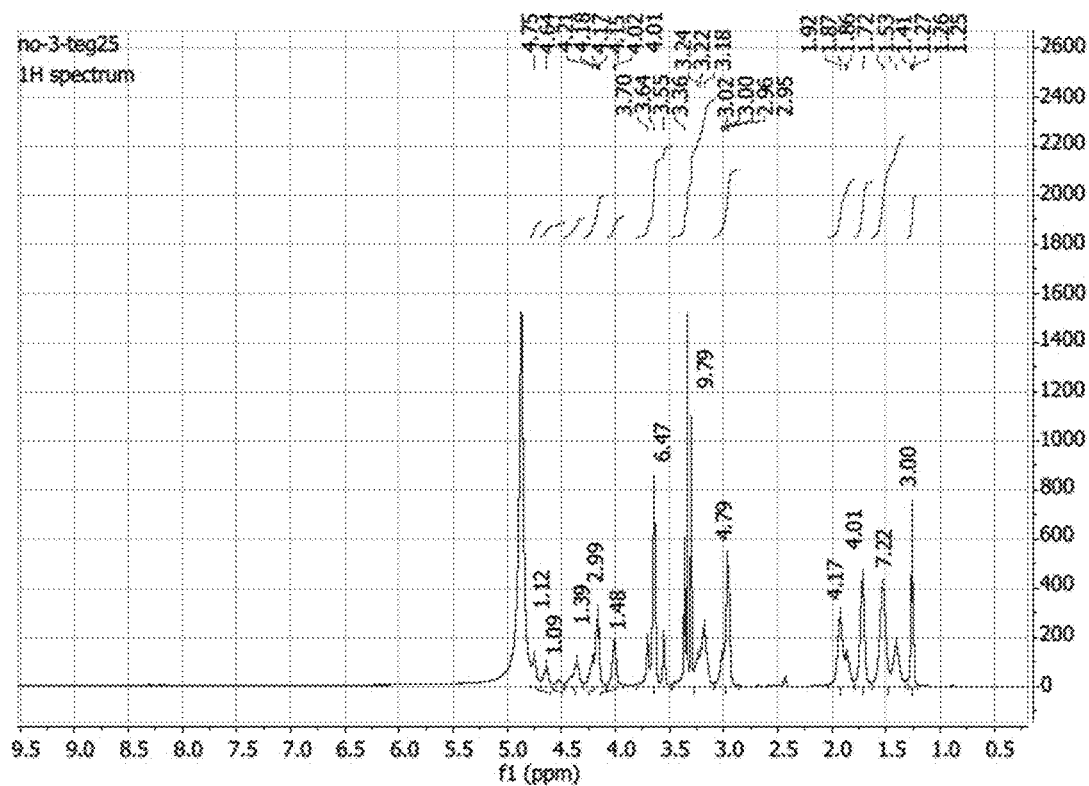
FIG. 14 provides a $^1$HNMR spectra of a denpol comprising a G1 25 TEG. $^1$H NMR (600 MHz, CD$_3$OD) δ 4.80-4.71 (m, 2H), 4.71-4.59 (m, 1H), 4.60-4.47 (m, 0.5 H), 4.47-4.30 (m, 1.39H), 4.29-4.10 (m, 3H), 4.12-3.90 (m, 1.5H), 3.80-3.50 (m, 6.47H), 3.36 (s, 0.7H), 3.28-3.11 (m, 7H), 3.10-2.87 (m, 4.8H), 2.04-1.81 (m, 4H), 1.79-1.63 (m, 4H), 1.64-1.32 (m, 7.2H), 1.26 (t, J=6.9 Hz, 3H).
Figure 15:
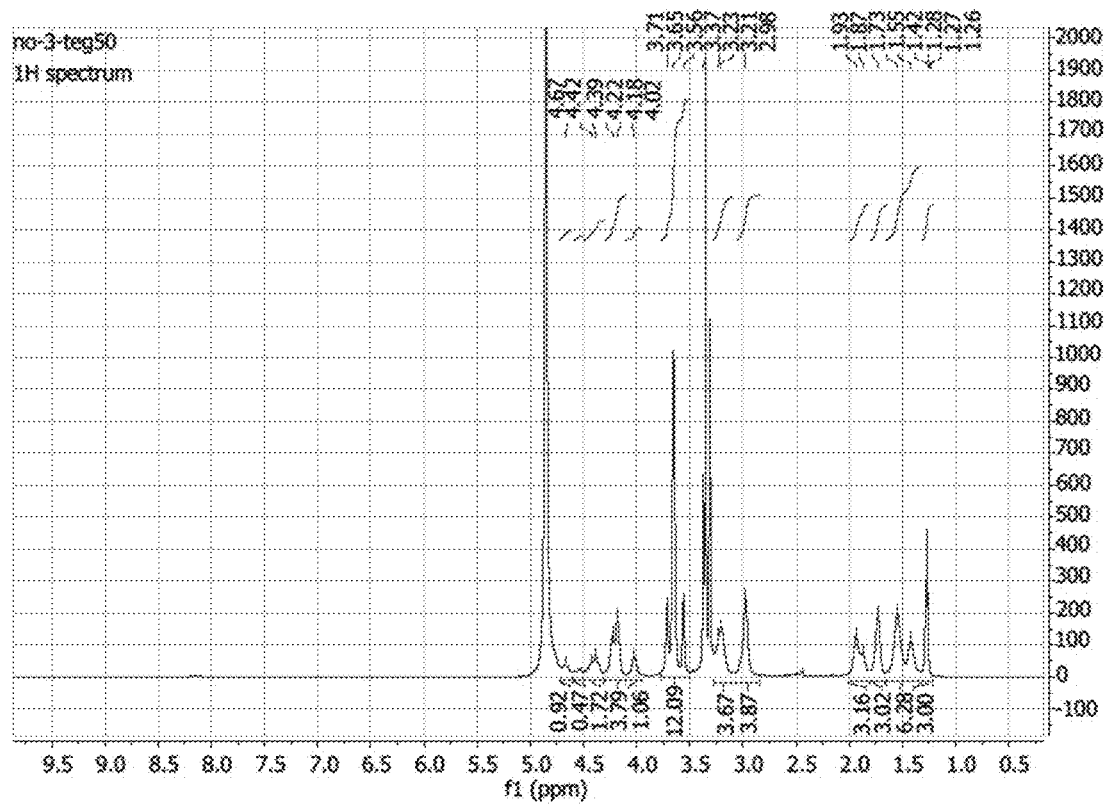
FIG. 15 provides a $^1$HNMR spectra of a denpol comprising a G1 50 TEG.
$^1$H NMR (600 MHz, CD$_3$OD) δ 4.72-4.61 (m, 1H), 4.60-4.49 (m, 0.47H), 4.48-4.32 (m, 1.72H), 4.30-4.10 (m, 4H), 4.11-3.96 (m, 1H), 3.79-3.51 (m, 12.1H), 3.37 (s, 1.2H), 3.29-3.08 (m, 3.67H), 3.08-2.86 (m, 3.9H), 2.03-1.81 (m, 3.16H), 1.81-1.65 (m, 3.02H), 1.66-1.34 (m, 6.28H), 1.27 (t, J=6.7 Hz, 3H).
Figure 16:
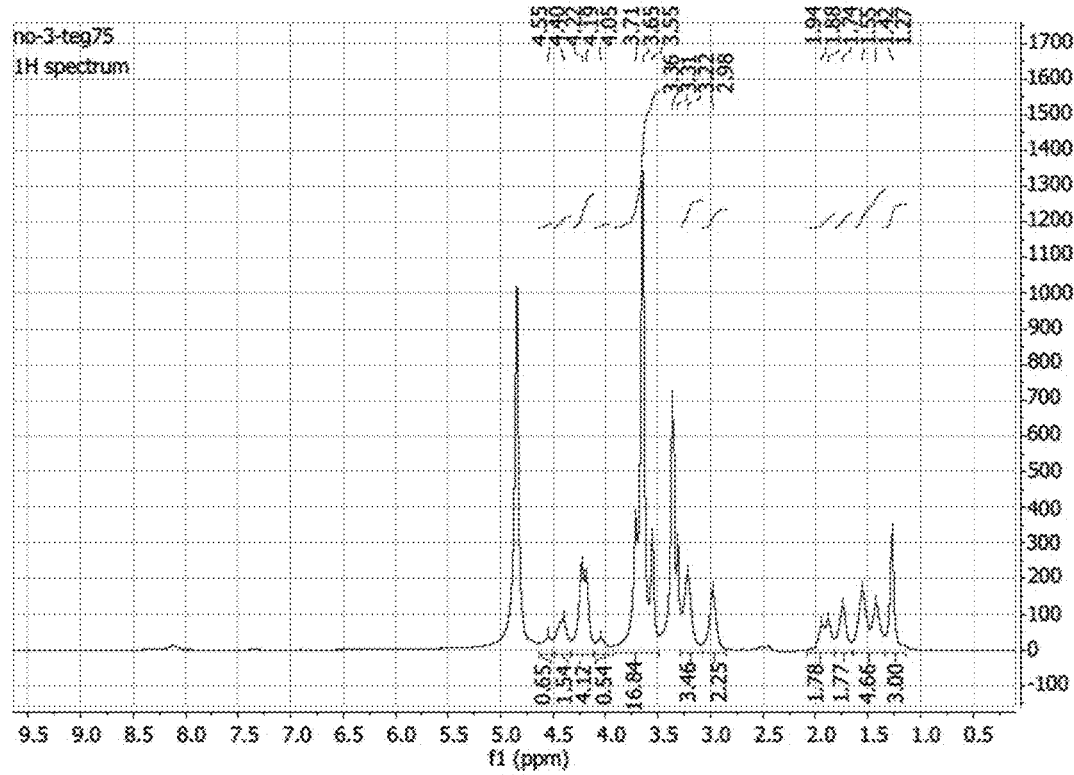
FIG. 16 provides a $^1$HNMR spectra of a denpol comprising a G1 75 TEG.

The synthesis of the denpols was completed in the same manner as previously reported using conventional peptide coupling chemistry and a "graft-from" approach as disclosed in Zeng et al. FIG. 1A shows a generalized G2 denpol structure, where the $R_1$ group can either be a lysine dendrimer or a PEG group, and the $R_2$ group can either be a His or Trp. For example, G2 25 TEG 3:1 represents a denpol that has 75% G2 lysine dendrons 25% tetraethylene glycol (TEG) on the backbone, and 75% his 25% trp (3:1 ratio of his:trp) functionalized off the surface of the lysine dendron (as determined by $^1$HNMR). FIG. 1B represents the library of denpols made and used in the study. His:Trp ratios of 3:1, 2:1, 1:1, 1:2 and 1:3 were targeted for functionalization to the G2 and G3 lysine dendrons. Results from the initial transfections (vida infra) were used to reduce the number of PEGylated vectors needed to complete the study. The non-PEGylated G2 and G3 denpols were tested first to determine if a higher generation or more trp had a positive effect on transfection ability. To assay mRNA delivery, NIH 3T3 cells were treated with a firefly luciferase (FLuc, 5-methylcytidine, pseudouridine modified) mRNA denpol nanoparticle. 15 hours post transfection, D-Luciferin was added, and luminescence was measured with an IVIS camera.

Transfection Studies with the Denpols and mRNA.

Lipofectamine MessengerMax™ (LF MM) was used as a positive control. Naked mRNA with no delivery vector and untreated cells were used as negative controls. The initial transfection conditions used were based off those optimized for siRNA transfections. The vector was used at an N:P ratio of 45 (molar ratio of protonated amines of the vector: phosphates of the mRNA). To form the nanoparticles, 200 ng of mRNA solution was added directly to a 10 mg/mL solution of the vector and mixed via pipette. The mixture was then diluted to a final volume with OptiMEM™ and mixed again with a pipette before incubation with the cells. The G2 denpols produced luminescence comparable to the positive control, whereas the G3 denpols were largely ineffective (see FIG. 45A). Interestingly, higher luminescence was observed when decreasing the His:Trp ratio from 3:1 to 2:1, but quickly drops off in efficiency when approaching 1:1, suggesting an optimal ratio of 2:1. When the ratio is decreased to 1:2 or 1:3, the vectors become cytotoxic and ineffective (see FIG. 44), therefore only ratios of 3:1, 2:1, or 1:1 were used for the PEGylated vectors. It was postulated that delivery efficiency decreases and toxicity increases as tryptophan increases past 1:1 because the dendron becomes too hydrophobic to bind siRNA and can also disrupt the cell membrane.

When denpol and mRNA were complexed and then added to complete media (10% fetal bovine serum (FBS) in OptiMEM™) instead of buffer alone, a universal increase in transfection efficiency was observed (see FIG. 46). Seeing this, the rest of the study was completed using at least 10% FBS. Increasing the amount of FBS to 80% in the transfection media had little or no effect on the transfection ability of the PEGylated denpols, but drastically diminished the efficacy of the non-PEGylated denpols (see FIG. 47). Presumably, PEGylation reduces nonspecific interactions with serum components and enhances the colloidal stability for the mRNA complexes. Next, differing N:P ratios for the PEGylated and non-PEGylated denpols were tested via transfection to find the optimal N:P ratio for mRNA delivery. Luminescence was greatest for the denpols surveyed between 5-15 N:P, drastically reducing the amount of vector needed for mRNA transfections vs. siRNA transfections (see FIG. 48). This was further confirmed using gel shift assays, which showed that all denpols bound mRNA by an N:P of 5 (see FIG. 49). Luminescence of non-PEGylated denpols plateaued after an N:P of 10 and did not increase at higher N:P ratios. Luminescence of PEGylated denpols peaked between an N:P of 10-15 and then decreased when more than the optimal amount of denpol was used (see FIG. 49). After optimized conditions had been identified (10% FBS, N:P 10) the denpols were all tested against each other to find the best vectors (see FIG. 45B, and FIG. 51 shows all vectors screened). In general, the vectors containing a His:Trp ratio of 2:1 and G2 lysine dendron gave the highest expression. G2 50 TEG 2:1 had the highest luminescence of the vectors measured. No cytotoxicity was observed via lactate dehydrogenase (LDH) assay, besides the vectors with a His:Trp ratio below 1:2 as mentioned above (see FIG. 44).

Further transfection studies were performed using cyanine 5 (cy-5) mRNA in conjunction with flow cytometry to examine cellular uptake and the percentage of cells transfected. Ideally, a synthetic mRNA vector would induce high amounts of protein expression in 100% of the cells intended for delivery. Indeed, the most effective vectors were able to transfect a majority of the cells (>70% contained cy-5 labeled mRNA, see FIG. 45B) with the best vectors transfecting over 90% of cells.

Dynamic Light Scattering Studies.

Dynamic light scattering (DLS) was used to examine the size and zeta potential of the denpol nanoparticles. DLS in PBS showed that the active non-PEGylated nanoparticles (G2 2:1 and G2 3:1) initially formed nanoparticles in the 100-200 nm range but aggregated over time (see FIG. 50A). The PEGylated denpols formed stable nanoparticles between 100-200 nm and did not aggregate. G3 denpols tended to aggregate quickly and form cloudy precipitates which could not be measured via DLS. Atomic force microscopy (AFM) was used to confirm nanoparticle size (see FIG. 52). Zeta potential measurements in PBS revealed negatively charged particles. The DLS data and transfection data agrees with the knowledge that nanoparticles in the 50-200 nm size range are generally optimal for cellular uptake. The DLS measurements in combination the transfection results agree that mRNA induces aggregation, (G2 3:1 does not aggregate when formulated with siRNA) and decreases transfection efficiency. Accordingly, when TEG was functionalized to the backbone, colloidal stability was regained, and transfection efficiency increased. Additional DLS studies were performed to probe why transfection efficacies increased in the presence of serum (10% FBS). Stable nano-particles in the same size range were obtained, but interestingly the non-PEGylated vectors did not aggregate. Previous studies in other groups have shown that albumin and other serum components can beneficially incorporate into nanoparticles and liposomes.

Confocal Microscope Studies.

Confocal microscopy using cy-5 labeled FLuc mRNA was used to look at internalization of the denpol mRNA nanoparticles (see FIG. 50B). Images of the G3 denpols shows large clusters of nanoparticles on the sides and surface of the cells and aggregates on the floor of the well, but shows little internalization (see FIG. 50B). TEG and PEGylated G2 denpols, showed more monodisperse particles, and were visualized to have internalized the mRNA denpol nanoparticles. There were no obvious differences between the 3:1 and 2:1 denpols when examined. The confocal images corroborates the DLS results, as one can visually see the large aggregates from the G3 denpols are not able to enter the cellular endosome or cytoplasm, and thus inefficiently deliver mRNA.

Studies Using Dendritic Cells.

As mentioned above, the delivery of antigen coding mRNA to dendritic cells can excite T cell activity against tumors. Moreover, nucleic acid delivery to dendritic cells is notorious for being inefficient. To demonstrate applicability, the denpol system was tested in DC 2.4 (immortalized murine dendritic cells) cells to see if transfection would be operative in an immune cell line. Using the transfection conditions optimized in 3T3 cells, it was observed that the same denpols that were active in 3T3 cells were also active in DC 2.4 (see FIG. 53A). Flow cytometry using cy-5 labeled GFP mRNA showed that a majority of cells (>50%) contained cy-5 mRNA and were GFP positive. After seeing that denpol was operative in DC 2.4 cells, further transfections using primary murine bone marrow derived dendritic cells (BMDCs) ex vivo were attempted. The best denpols tested transfected>70% of the BMDCs (contained cy-5 labeled mRNA) and provided significant production of GFP (see FIG. 53B). Additionally, the successful delivery of both GFP (996 ribonucleotides) and FLuc (1929 ribonucleotides) mRNA shows that denpol can efficiently accommodate different length mRNA. The high efficiency of delivery to both DC 2.4 and BMDC cells exhibits that denpols can be used in applications that require high transfection efficiencies with mRNA, including mRNA based vaccinations.

One-Pot Co-Delivery of sgRNA and mRNA for CRISPR/Cas9 Genome Editing.

To test if the denpol could be useful for gene editing applications, 250 ng of Cas9 mRNA (4509 ribonucleotides) and 25-150 ng of anti-eGFP sgRNA were co-delivered to transgenic eGFP expressing DB-7 cells (murine fibroblasts) using 3 different concentrations (10, 15, and 20 N:P) of denpol G2 50 TEG 2:1 in a 96 well plate. eGFP activity was monitored with time using flow cytometry. Gene editing via Cas9 systems can take between 24-72 h depending on the delivery method, and eGFP half-life is around 1 day, so analysis should take place after a sufficient waiting period. Successful gene editing (~35% of cells) using the denpol materials was observed via the knock out of the eGFP protein over 8 days (FIG. 54A). At 250 ng of mRNA, LF MM was significantly cytotoxic (>90%) so the study for the positive control was repeated at 150 ng of mRNA. In contrast, the denpol did not show any cytotoxicity at 250 ng mRNA level, highlighting the advantage of using denpol vectors for this application (FIG. 54B). The result clearly demonstrates that the denpols exhibit better efficiency for gene editing than the positive control.

A number of embodiments have been described herein. Nevertheless, it will be understood that various modifications may be made without departing from the spirit and scope of this disclosure. Accordingly, other embodiments are within the scope of the following claims.

What is claimed is:

1. A complex comprising:
   (a) one or more mRNAs and/or ssRNAs that comprise at least 100 ribonucleotides, and
   (b) a vector comprising a structure of Formula I:

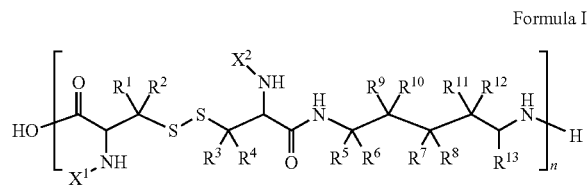

Formula I wherein,
   n is an integer greater than 5;
   $R^1$-$R^{12}$ are independently selected from the group consisting of H, optionally substituted ($C_1$-$C_6$)-alkyl, optionally substituted ($C_1$-$C_6$)-heteroalkyl, optionally substituted ($C_1$-$C_6$)-alkenyl, optionally substituted ($C_1$-$C_6$)-heteroalkenyl, optionally substituted ($C_1$-$C_6$)-alkynyl, optionally substituted ($C_1$-$C_6$)-heteroalkynyl, optionally substituted ($C_3$-$C_{12}$)cycloalkyl, optionally substituted ($C_4$-$C_{12}$)cycloalkenyl, optionally substituted aryl, optionally substituted heterocycle, halide, hydroxyl, carbonyl, aldehyde, carboxyl, ester, alkoxy, carboxamide, amine, imine, azide, cyano, nitro, nitroso, thiol, sulfide, sulfoxide, sulfone, and phosphate;
   $R^{13}$ is an ester;
   $X^1$-$X^2$ are independently selected from a polyoxyalkylene polymer and an optionally substituted L-lysine based dendron that is functionalized on the outer layer by comprising histidine and tryptophan moieties; and
   wherein at least one of $X^1$-$X^2$ is an optionally substituted L-lysine based dendron and wherein at least one of $X^1$-$X^2$ is a polyoxyalkylene polymer, and wherein for the $X^1$-$X^2$ groups, the polyoxyalkylene polymer represents by percent moles from 25% to 75% of the $X^1$-$X^2$ groups of the vector, and
   wherein the ratio of histidine to tryptophan moieties is 2.5:1 to 1:1,
   wherein the molar ratio of protonated amines of the dendronized polymer:
   phosphates of the mRNAs and/or ssRNAs (N:P) is from 5 to 20.

2. The complex of claim 1, wherein the vector comprises a structure of Formula I(a):

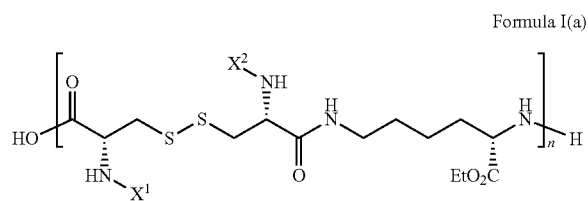

Formula I(a)

wherein,
   n is an integer greater than 50;
   $X^1$-$X^2$ are independently selected from the group consisting of:

(i) a structure of Formula II:

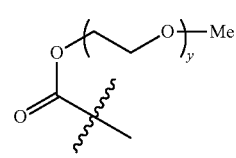

Formula II wherein y is an integer of 3 or greater, and
(ii) a structure of Formula III:

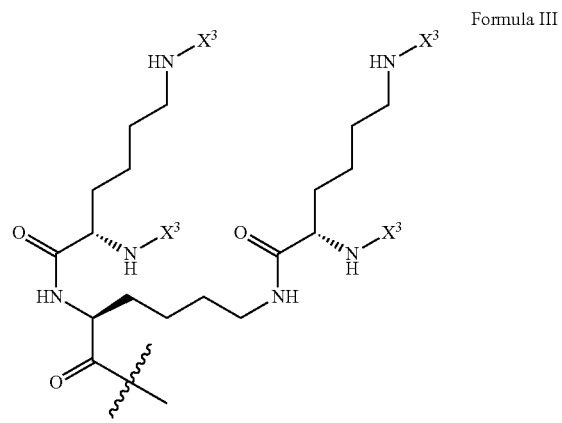

Formula III where $X^3$ is a histidine moiety or a tryptophan moiety; and wherein at least one of $X^1$-$X^2$ has the structure of Formula II and wherein at least one of $X^1$-$X^2$ has the structure of Formula III, and wherein the ratio of histidine to tryptophan moieties is 2.5:1 to 1:1.

3. The complex of claim 2, wherein y is 3.
4. The complex of claim 2, wherein y is >3.
5. The complex of claim 1, wherein the ratio of histidine to tryptophan moieties is 2:1.
6. The complex of claim 1, wherein the N:P ratio is from 10 to 15.
7. The complex of claim 6, wherein the N:P ratio is about 10.
8. The complex of claim 1, wherein the one or more mRNAs and/or ssRNAs consists of 100 to 20,000 ribonucleotides.
9. The complex of claim 1, wherein the dendronized polymer further comprises a targeting ligand.
10. The complex of claim 1, wherein the targeting ligand is selected from the group consisting of (a) antibodies, (b) aptamers, (c) cholesterol and its derivatives, (d) folate compounds or folate conjugates, (e) transferrin, (f) saccharides and (g) cell-penetrating peptides.
11. The complex of claim 1, wherein the one or more mRNAs and/or ssRNAs encode a peptide or protein antigen isolated from a tumor.
12. The complex of claim 1, wherein at least a portion of the one or more mRNAs and/or ssRNAs comprises modified ribonucleotides in the place of naturally occurring ribonucleotides, wherein the modified ribonucleotides have a nucleobase selected from the group consisting of pseudouridine, 5-methyluridine, 2-thiouridine, 5-methylcytidine (m5C), and N6-methyladenosine.
13. A method for delivering one or more mRNA and/or ssRNAs into a cell comprising:
   contacting a cell with a complex of claim 1.

14. The method of claim 13, wherein the cell is contacted in vitro.

15. The method of claim 13, wherein the cell is contacted in vivo.

16. The method of claim 13, wherein the cell is a cancer cell.

17. A method of promoting prophylactic or therapeutic antitumor immunity in a subject comprising administering the complex of claim 11 to a subject, wherein the complex is delivered to the subject in vivo, or to cells ex vivo prior to administration of said cells to said subject.

18. A method of editing a genome of a cell comprising contacting the cell with the complex of claim 1, wherein the one or more mRNAs and/or ssRNAs comprise cas9 mRNA and an sgRNA.

* * * * *